(12) United States Patent
Watanabe et al.

(10) Patent No.: US 10,283,718 B2
(45) Date of Patent: May 7, 2019

(54) CHARGE TRANSPORTING MATERIAL, ORGANIC ELECTROLUMINESCENT ELEMENT, LIGHT EMITTING DEVICE, DISPLAY DEVICE AND ILLUMINATION DEVICE

(71) Applicant: UDC Ireland Limited, Dublin (IE)

(72) Inventors: Kousuke Watanabe, Kanagawa (JP); Yosuke Yamamoto, Kanagawa (JP); Wataru Sotoyama, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 1013 days.

(21) Appl. No.: 13/897,760

(22) Filed: May 20, 2013

(65) Prior Publication Data

US 2013/0313532 A1 Nov. 28, 2013

(30) Foreign Application Priority Data

May 22, 2012 (JP) .................. 2012-116659

(51) Int. Cl.
*H01L 51/54* (2006.01)
*C07D 498/06* (2006.01)
(Continued)

(52) U.S. Cl.
CPC ........ *H01L 51/0071* (2013.01); *C07D 471/06* (2013.01); *C07D 498/06* (2013.01);
(Continued)

(58) Field of Classification Search
USPC ..................................... 544/99, 31
See application file for complete search history.

(56) References Cited

U.S. PATENT DOCUMENTS

| | | | | |
|---|---|---|---|---|
| 2009/0295275 | A1* | 12/2009 | Parham et al. ...... | C07D 471/16 313/504 |
| 2012/0202997 | A1* | 8/2012 | Parham et al. ...... | C07D 471/04 544/180 |
| 2013/0026422 | A1* | 1/2013 | Parham et al. ...... | C07D 471/06 252/500 |

FOREIGN PATENT DOCUMENTS

| | | |
|---|---|---|
| JP | 2010050778 | 3/2010 |
| JP | 2012-248663 | 12/2012 |

(Continued)

*Primary Examiner* — Marie R. Yamnitzky
(74) *Attorney, Agent, or Firm* — Riverside Law LLP

(57) ABSTRACT

A charge transporting material comprising a compound represented by any one of the following general formula (1-1) to general formula (1-3):

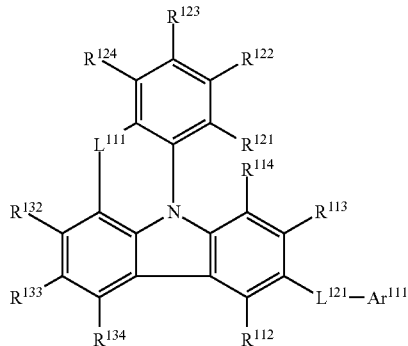

General Formula (1-1)

General Formula (1-2)

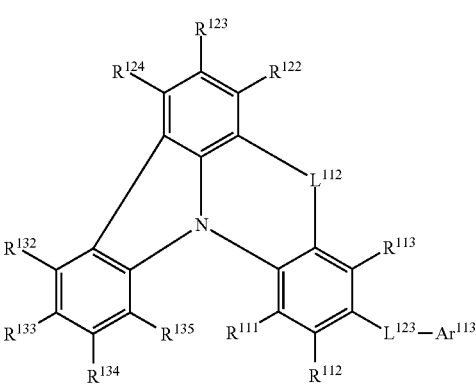

General Formula (1-3)

wherein $R^{111}$ to $R^{114}$, $R^{121}$ to $R^{125}$ and $R^{131}$ to $R^{135}$ each independently represent a hydrogen atom or a substituent, and may be bound together to form a ring; $L^{111}$ to $L^{113}$ each independently represent O or S; $L^{121}$ to $L^{123}$ each independently represent a single bond or a divalent linking group; and $Ar^{111}$ to $Ar^{113}$ each independently represent an aryl group or a heteroaryl group.

13 Claims, 1 Drawing Sheet

(51) Int. Cl.
 *C07D 513/06* (2006.01)
 *H01L 51/00* (2006.01)
 *C07D 471/06* (2006.01)
 *H01L 51/50* (2006.01)

(52) U.S. Cl.
 CPC ........ *C07D 513/06* (2013.01); *H01L 51/0067* (2013.01); *H01L 51/0085* (2013.01); *H01L 51/5016* (2013.01); *H01L 51/5056* (2013.01)

(56) References Cited

FOREIGN PATENT DOCUMENTS

WO     2011042107        4/2011
WO   WO 2011/128017 A1 * 10/2011
WO   WO 2012/077582 A1 *  6/2012

\* cited by examiner

[Fig. 1]
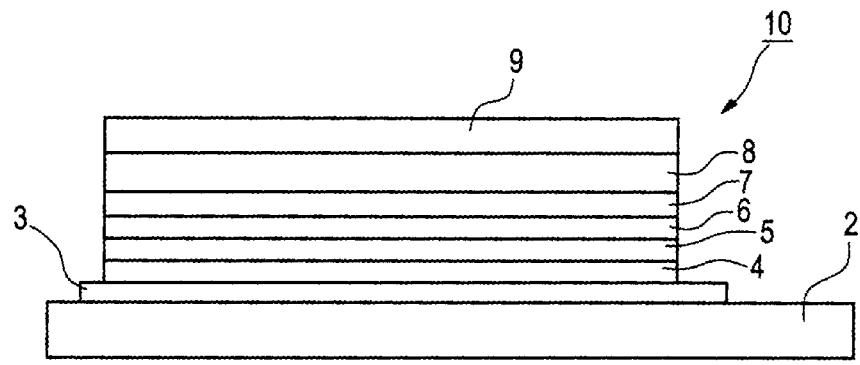
[Fig. 2]
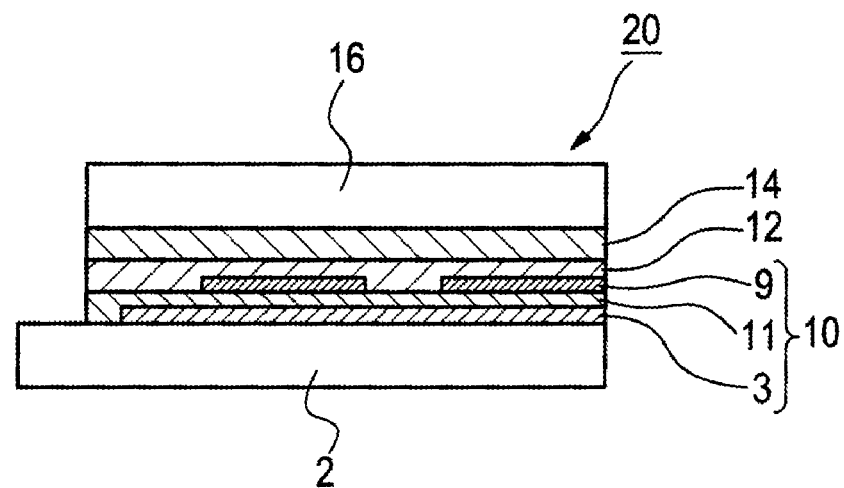
[Fig. 3]
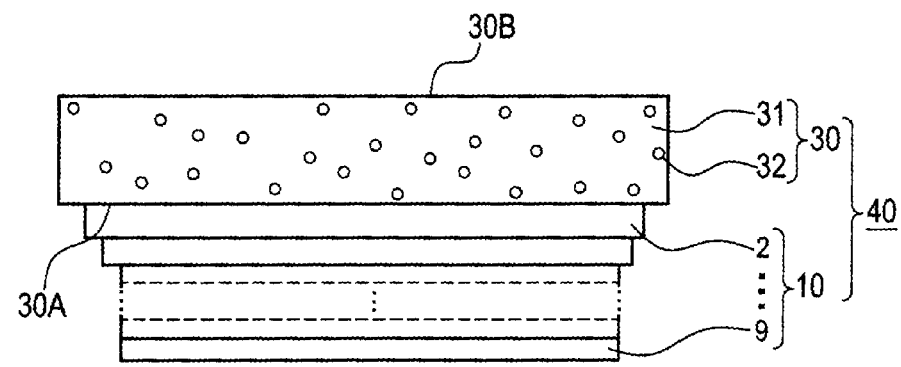

CHARGE TRANSPORTING MATERIAL, ORGANIC ELECTROLUMINESCENT ELEMENT, LIGHT EMITTING DEVICE, DISPLAY DEVICE AND ILLUMINATION DEVICE

CROSS-REFERENCE TO RELATED APPLICATIONS

The present U.S. patent application claims priority benefit from Japanese Patent Appl. No. 2012-116659, filed 22 May 2012, which is incorporated by reference herein in its entirety.

FIELD OF THE INVENTION the present invention relates to a charge transporting material, an organic electroluminescent element, a light emitting device, a display device and an illumination device.

BACKGROUND OF THE INVENTION

Since organic electroluminescent elements (which may hereinafter also be referred to as "elements" or "organic EL elements") are capable of high-luminance light emitting using low voltage driving, they have been actively researched and developed. The organic electroluminescent elements have a pair of electrodes and an organic layer between the pair of electrodes, and utilize, for light emitting, energy of the exciton generated as a result of recombination of the electron injected from the cathode and the hole injected from the anode in the organic layer.

In recent years, by using phosphorescence emitting materials, elements are being enhanced in efficiency. Patent Document 1 discloses a charge transporting material having a site of a fused ring structure derived from triarylamine, for decreasing driving voltage and enhancing efficiency and durability. Patent Document 2 discloses a charge transporting material having a site of a fused ring structure derived from triarylamine, for decreasing driving voltage and enhancing efficiency.

RELATED ART DOCUMENT

Patent Document

[Patent Document 1] WO 2011/042107
[Patent Document 2] JP-A-2010-050778

SUMMARY OF THE INVENTION

Problem that the Invention is to Solve

On the other hand, development of an organic electroluminescent element emitting green phosphorescence, among organic electroluminescent elements using phosphorescence emitting materials, has recently been important in application to a full-color display or the like.

The present inventors used a compound disclosed in Patent Documents 1 and 2 as a host material of a light emitting layer in an organic electroluminescent element emitting green phosphorescence to evaluate the element performance thereof, and as a result, it was revealed that the compound disclosed in Patent Document 1 is inferior in the luminous efficiency when it is used for an organic electroluminescent element emitting green phosphorescence and also has a problem in durability. It was also revealed that the element using a compound disclosed in Patent Document 2 exhibited too high driving voltage or was inferior in durability. That is, the elements obtained using previously reported compounds all have had problems of too high driving voltage, low luminous efficiency, or low durability.

Accordingly, an object of the present invention is to provide an charge transporting material which allows for a low driving voltage and is superior in luminous efficiency and durability.

Means for Solving the Problem

As a result of the study of the present inventors, it was found that a charge transporting material can be provided, from which an organic electroluminescent element that can be driven with a low driving voltage and is superior in luminous efficiency and durability can be manufactured, by a compound having a structure obtained by allowing a triarylamine to fuse with an —O— or —S— linking group and having a substituent containing an aryl group or a heteroaryl group at a para-position of at least one of the aryl groups of the triarylamine.

The present invention, which is a specific means for solving the above problem, has the following constitution.

[1] A charge transporting material comprising a compound represented by any one of the following general formula (1-1) to general formula (1-3):

General Formula (1-1)

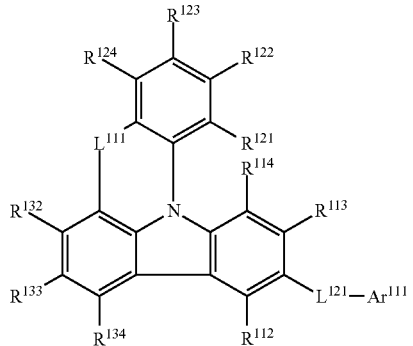

General Formula (1-2)

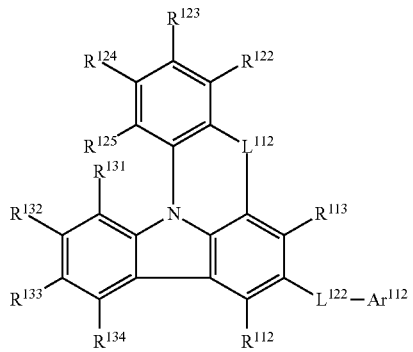

General Formula (1-3)

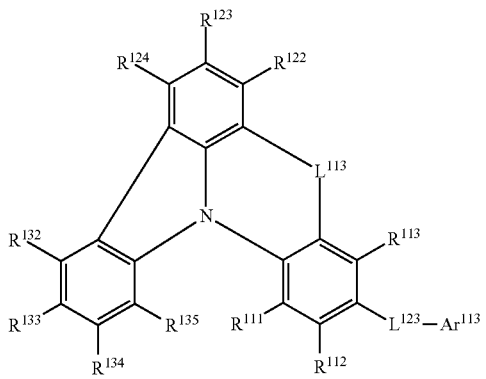

[wherein in the general formulae (1-1) to (1-3), $R^{111}$ to $R^{114}$, $R^{121}$ to $R^{125}$ and $R^{131}$ to $R^{135}$ each independently represent a hydrogen atom or a substituent, and may be bound together to form a ring; $L^{111}$ to $L^{113}$ each independently represent O or S; $L^{121}$ to $L^{123}$ each independently represent a single bond or a divalent linking group; and $Ar^{111}$ to $Ar^{123}$ each independently represent an aryl group or a heteroaryl group].

[2] The charge transporting material described in [1] preferably comprises a compound represented by the general formula (1-1) or the general formula (1-2).

[3] In the charge transporting material described in [1] or [2], it is preferred that $Ar^{111}$ to $Ar^{113}$ in the general formulae (1-1) to (1-3) are each independently a substituent represented by any one of the following general formula (2-1) to general formula (2-10):

General Formula (2-1)

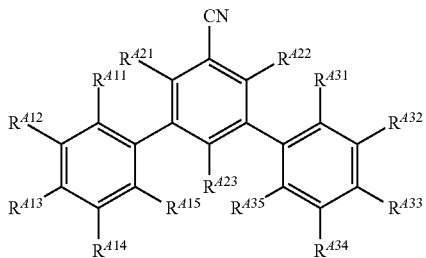

General Formula (2-2)

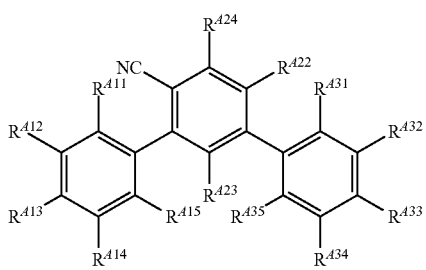

General Formula (2-3)

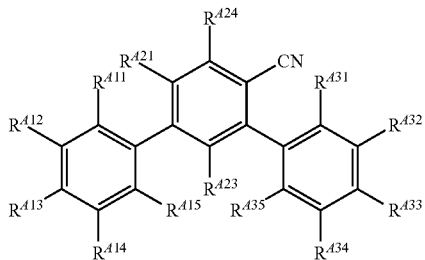

General Formula (2-4)

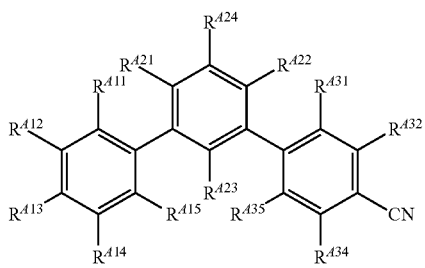

General Formula (2-5)

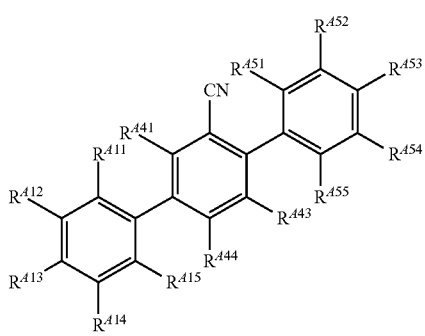

General Formula (2-6)

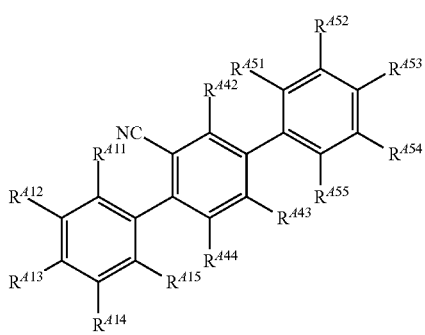

General Formula (2-7)

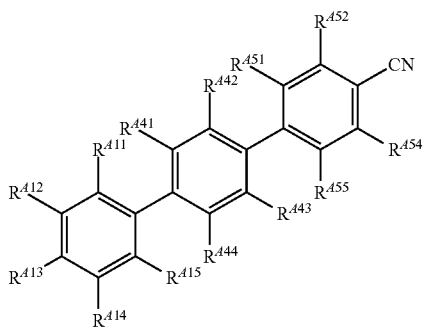

General Formula (2-8)

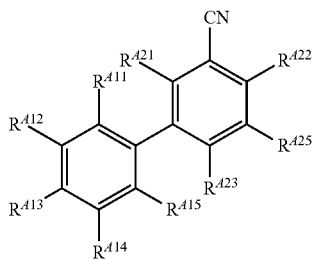

General Formula (2-9)

General Formula (2-10)

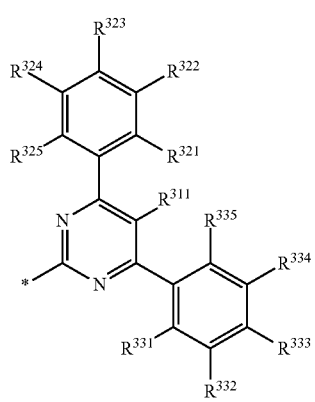

[wherein in the general formula (2-1) to the general formula (2-10), it is preferred that one of $R^{411}$ to $R^{415}$ represents a biding position to $L^{121}$ to $L^{123}$ in the general formulae (1-1) to (1-3) and the others of $R^{411}$ to $R^{415}$ each independently represent a hydrogen atom or a substituent; and $R^{421}$ to $R^{425}$, $R^{431}$ to $R^{435}$, $R^{441}$ to $R^{445}$ and $R^{451}$ to $R^{455}$ each independently represent a hydrogen atom or a substituent].

[4] In the charge transporting material described in [1] or [2], it is preferred that $Ar^{111}$ to $Ar^{113}$ in the general formulae (1-1) to (1-3) are each independently a substituent represented by any one of the following general formula (3-1) to general formula (3-3):

General Formula (3-1)

General Formula (3-2)

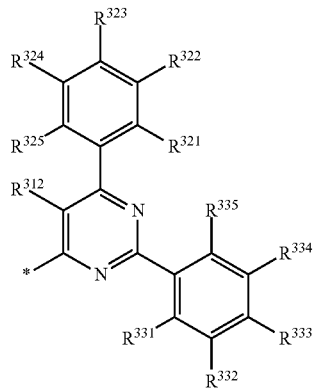

General Formula (3-3)

[wherein in the general formulae (3-1) to (3-3), * represents a binding position to $L^{121}$ to $L^{123}$ in the general formulae (1-1) to (1-3); and $R^{311}$, $R^{312}$, $R^{321}$ to $R^{325}$ and $R^{331}$ to $R^{335}$ each independently represent a hydrogen atom or a substituent].

[5] In the charge transporting material described in [1] or [2], it is preferred that $Ar^{111}$ in the general formula (1-1) is a substituent represented by the following general formula (4-1):

General Formula (4-1)

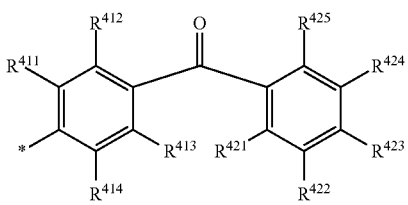

[wherein in the general formula (4-1), * represents a binding position to $L^{121}$ in the general formula (1-1); and $R^{411}$ to $R^{414}$ and $R^{421}$ to $R^{425}$ each independently represent a hydrogen atom or a substituent].

[6] In the charge transporting material described in any one of [1] to [5], it is preferred that at least one of $L^{121}$ to $L^{123}$ and $Ar^{123}$ to $Ar^{113}$ in the general formulae (1-1) to (1-3) contains an m-phenylene group.

[7] An organic electroluminescent element comprising a substrate; a pair of electrodes including an anode and a cathode, disposed on the substrate; and an organic layer disposed between the electrodes, characterized in that the organic layer contains the charge transporting material described in any one of [1] to [6].

[8] In the organic electroluminescent element described in [7], it is preferred that the organic layer includes a light emitting layer containing a phosphorescence emitting material.

[9] In the organic electroluminescent element described in [8], it is preferred that the light emitting layer contains the compound represented by any one of the general formula (1-1) to the general formula (1-3).

[10] In the organic electroluminescent element described in [8] or [9], it is preferred that an Ir complex represented by the following general formula (E-1) is used in the light emitting layer as the phosphorescence emitting material:

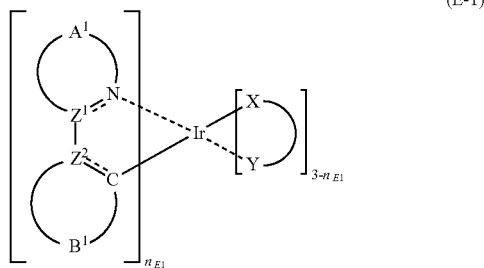

(E-1)

[wherein in the general formula (E-1), $Z^1$ and $Z^2$ each represent a carbon atom or a nitrogen atom; $A^1$ represents an atomic group which together with $Z^1$ and a nitrogen atom forms a 5- or 6-membered hetero ring; $B^1$ represents an atomic group which together with $Z^2$ and a carbon atom forms a 5- or 6-membered ring; $Z^1$ and $Z^2$ each independently represent a carbon atom or a nitrogen atom; (X—Y) represents a mono-anionic bidentate ligand; and $n_{E1}$ represents an integer of 1 to 3].

[11] In the organic electroluminescent element described in [10], the Ir complex represented by the general formula (E-1) is preferably represented by the following general formula (E-2):

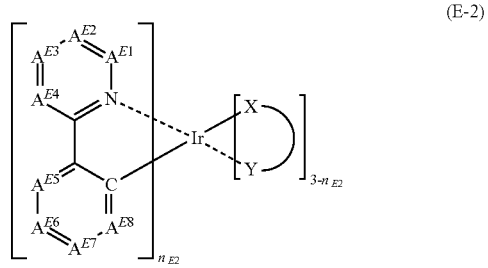

(E-2)

[wherein in the general formula (E-2), $A^{E1}$ to $A^{E8}$ each independently represent a nitrogen atom or C—$R^E$; $R^E$ represents a hydrogen atom or a substituent; (X—Y) represents a mono-anionic bidentate ligand; and $n_{E2}$ represents an integer of 1 to 3].

[12] A light emitting device characterized by comprising the organic electroluminescent element described in any one of [1] to [11].

[13] A display device characterized by comprising the organic electroluminescent element described in any one of [1] to [11].

[14] An illumination device characterized by comprising the organic electroluminescent element described in any one of [1] to [11].

Advantage of the Invention

According to the present invention, a charge transporting material can be provided which allows for a low driving voltage, and is superior in luminous efficiency and durability. In addition, by the charge transporting material according to the present invention, an organic electroluminescent element can be provided which can be driven with a low driving voltage, and is superior in luminous efficiency and durability.

BRIEF DESCRIPTION OF THE DRAWINGS

FIG. 1 It is a schematic view showing one example of a configuration of the organic electroluminescent element according to the present invention.

FIG. 2 It is a schematic view showing one example of the light emitting device according to the present invention.

FIG. 3 It is a schematic view showing one example of the illumination device according to the present invention.

MODE FOR CARRYING OUT THE INVENTION

Details of the present invention are hereunder described. The description of the configuration requirements below may be based on representative embodiments of the present invention, but the present invention is not limited to these embodiments. Incidentally, in the present specification, the range expressed with "to" means a range including the numerical values before and after "to" as the lower limit and the upper limit, respectively.

[Charge Transporting Material]

The charge transporting material according to the present invention is characterized by comprising a compound represented by any one of the following general formula (1-1) to general formula (1-3):

General Formula (1-1)

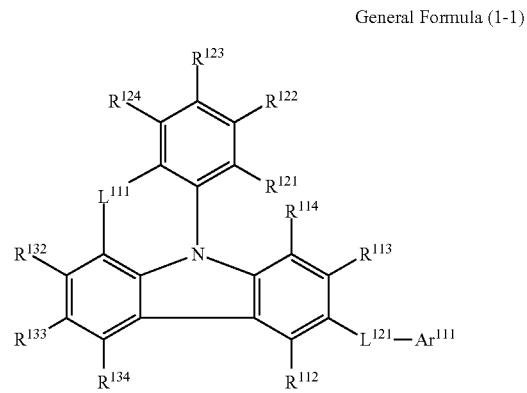

-continued

General Formula (1-2)

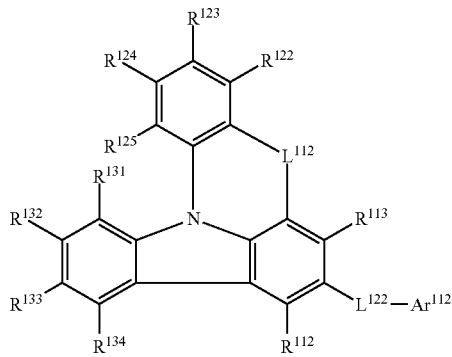

General Formula (1-3)

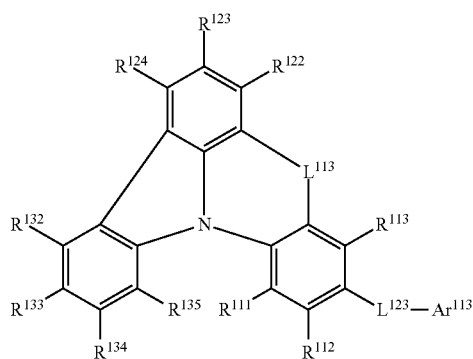

[wherein in the general formulae (1-1) to (1-3), $R^{111}$ to $R^{114}$, $R^{121}$ to $R^{125}$ and $R^{131}$ to $R^{135}$ each independently represent a hydrogen atom or a substituent, and may be bound together to form a ring; $L^{111}$ to $L^{113}$ each independently represent O or S; $L^{121}$ to $L^{123}$ each independently represent a single bond or a divalent linking group; and $Ar^{111}$ to $Ar^{113}$ each independently represent an aryl group or a heteroaryl group].

Although not wishing to be bound by any theory, such a constitution of the compound of the present invention makes it possible to provide a high luminous efficiency as well as a low voltage and enhanced durability when the compound is used as a material for an organic electroluminescent element. The durability can be enhanced by introducing a structure obtained by allowing triphenylamine to fuse with an oxygen atom or a sulfur atom, and in addition, by making the highly electron-accepting group represented by $Ar^{111}$ to $Ar^{113}$ have a specific structure. This is believed to be due to stabilization of HOMO, suppression of cleavage of N-phenyl bonds in the triarylamine where the HOMO distributes, and protection of the reactive point of the site where the LUMO distributes. The lower voltage is assumed to be caused by decrease of the ionization potential (and increase of the electron affinity).

The charge transporting material represented by any one of the general formula (1-1) to the general formula (1-3) can be preferably used for organic electronic elements such as an electrophotography, an organic transistor, an organic photoelectric transducer (for energy conversion, a sensor, or other applications), and an organic electroluminescent element, and especially preferably used for an organic electroluminescent element.

The charge transporting material according to the present invention can be used for a thin film containing the compound represented any one of the general formula (1-1) to the general formula (1-3). The thin film can be formed by a dry film forming method such as a vapor deposition method, a sputtering method, etc. or a wet film forming method such as a transfer method, a printing method, etc. by using the composition. The thin film may have any film thickness depending on the use thereof, and the thickness is preferably 0.1 nm to 1 mm, more preferably 0.5 nm to 1 μm, still more preferably 1 nm to 200 nm, and especially preferably 1 nm to 100 nm.

A preferred range of the charge transporting material including the compound represented by any of the general formula (1-1) to the general formula (1-3) is hereinunder described.

In the present invention, hydrogen atoms in the description of the general formula (1-1) to the general formula (1-3) or the other general formulae indicate to include isotopes (deuterium or the like), and atoms which constitute a further substituent indicate to include isotopes thereof.

In the present invention, a "substituent" means that the substituent may be further substituted. For example, when an "alkyl group" is mentioned in the present invention, the alkyl group includes an alkyl group substituted with fluorine atoms (such as a trifluoromethyl group), an alkyl group substituted with aryl groups (such as a triphenylmethyl group), or the like. When an "alkyl group having 1 to 6 carbon atoms" is mentioned, however, the phrase means that the carbon number of the whole group including all substituents is 1 to 6.

General Formula (1-1)

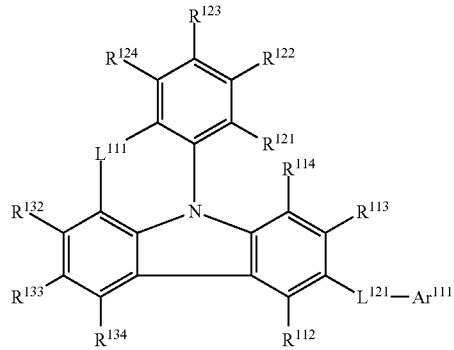

General Formula (1-2)

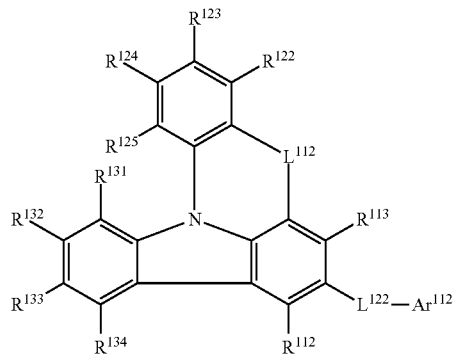

General Formula (1-3)

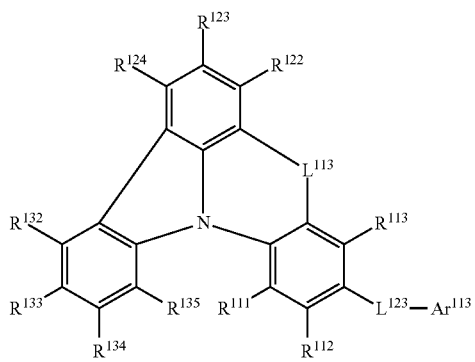

In the general formula (1-1) to the general formula (1-3), $R^{111}$ to $R^{114}$, $R^{121}$ to $R^{125}$ and $R^{131}$ to $R^{135}$ each independently represent a hydrogen atom or a substituent, and may be bound together to form a ring.

In the general formula (1-1) to the general formula (1-3), the substituent represented by $R^{111}$ to $R^{114}$ include, but is not particularly limited to, groups represented by the following Substituent Group A.

<<Substituent Group A>>

An alkyl group (having preferably from 1 to 30 carbon atoms, more preferably from 1 to 20 carbon atoms, and especially preferably from 1 to 10 carbon atoms; for example, methyl, ethyl, n-propyl, isopropyl, t-butyl, n-hexyl, n-octyl, n-decyl, n-hexadecyl, cyclopropyl, cyclopentyl, cyclohexyl, and a trifluoromethyl group), an alkenyl group (having preferably from 2 to 30 carbon atoms, more preferably from 2 to 20 carbon atoms, and especially preferably from 2 to 10 carbon atoms; for example, vinyl, allyl, 2-butenyl, and 3-pentenyl), an alkynyl group (having preferably from 2 to 30 carbon atoms, more preferably from 2 to 20 carbon atoms, and especially preferably from 2 to 10 carbon atoms; for example, propargyl, and 3-pentynyl), an aryl group (having preferably from 6 to 30 carbon atoms, more preferably from 6 to 20 carbon atoms, and especially preferably from 6 to 14 carbon atoms; for example, phenyl, p-methylphenyl, a 2-fluorophenyl group, a 3-fluorophenyl group, a 4-fluorophenyl group, naphthyl, anthranyl, and triphenylenyl), an amino group (having preferably from 0 to 30 carbon atoms, more preferably from 0 to 20 carbon atoms, and especially preferably from 0 to 10 carbon atoms; for example, amino, methylamino, dimethylamino, diethylamino, dibenzylamino, phenylamino, diphenylamino, and ditolylamino), an alkoxy group (having preferably from 1 to 30 carbon atoms, more preferably from 1 to 20 carbon atoms, and especially preferably from 1 to 10 carbon atoms; for example, methoxy, ethoxy, butoxy, and 2-ethylhexyloxy), an aryloxy group (having preferably from 6 to 30 carbon atoms, more preferably from 6 to 20 carbon atoms, and especially preferably from 6 to 12 carbon atoms; for example, phenyloxy, 1-naphthyloxy, and 2-naphthyloxy), a heterocyclic oxy group (having preferably from 1 to 30 carbon atoms, more preferably from 1 to 20 carbon atoms, and especially preferably from 1 to 12 carbon atoms; for example, pyridyloxy, pyrazyloxy, pyrimidyloxy, and quinolyloxy), an acyl group (having preferably from 2 to 30 carbon atoms, more preferably from 2 to 20 carbon atoms, and especially preferably from 2 to 12 carbon atoms; for example, acetyl, benzoyl, formyl, and pivaloyl), an alkoxycarbonyl group (having preferably from 2 to 30 carbon atoms, more preferably from 2 to 20 carbon atoms, and especially preferably from 2 to carbon atoms; for example, methoxycarbonyl, and ethoxycarbonyl), an aryloxycarbonyl group (having preferably from 7 to 30 carbon atoms, more preferably from 7 to 20 carbon atoms, and especially preferably from 7 to 12 carbon atoms; for example, phenyloxycarbonyl), an acyloxy group (having preferably from 2 to 30 carbon atoms, more preferably from 2 to 20 carbon atoms, and especially preferably from 2 to 10 carbon atoms; for example, acetoxy and benzoyloxy), an acylamino group (having preferably from 2 to 30 carbon atoms, more preferably from 2 to 20 carbon atoms, and especially preferably from 2 to 10 carbon atoms; for example, acetylamino and benzoylamino), an alkoxycarbonylamino group (having preferably from 2 to 30 carbon atoms, more preferably from 2 to 20 carbon atoms, and especially preferably from 2 to 12 carbon atoms; for example, methoxycarbonylamino), an aryloxycarbonylamino group (having preferably from 7 to 30 carbon atoms, more preferably from 7 to 20 carbon atoms, and especially preferably from 7 to 12 carbon atoms; for example, phenyloxycarbonylamino), a sulfonylamino group (having preferably from 1 to 30 carbon atoms, more preferably from 1 to 20 carbon atoms, and especially preferably from 1 to 12 carbon atoms; for example, methanesulfonylamino and benzenesulfonylamino), a sulfamoyl group (having preferably from 0 to 30 carbon atoms, more preferably from 0 to 20 carbon atoms, and especially preferably from 0 to 12 carbon atoms; for example, sulfamoyl, methylsulfamoyl, dimethylsulfamoyl, and phenylsulfamoyl), a carbamoyl group (having preferably from 1 to 30 carbon atoms, more preferably from 1 to 20 carbon atoms, and especially preferably from 1 to 12 carbon atoms; for example, carbamoyl, methylcarbamoyl, diethylcarbamoyl, and phenylcarbamoyl), an alkylthio group (having preferably from 1 to 30 carbon atoms, more preferably from 1 to 20 carbon atoms, and especially preferably from 1 to 12 carbon atoms; for example, methylthio and ethylthio), an arylthio group (having preferably from 6 to 30 carbon atoms, more preferably from 6 to 20 carbon atoms, and especially preferably from 6 to 12 carbon atoms; for example, phenylthio), a heterocyclic thio group (having preferably from 1 to 30 carbon atoms, more preferably from 1 to 20 carbon atoms, and especially preferably from 1 to 12 carbon atoms; for example, pyridylthio, 2-benzimizolylthio, 2-benzoxazolylthio, and 2-benzthiazolylthio), a sulfonyl group (having preferably from 1 to 30 carbon atoms, more preferably from 1 to 20 carbon atoms, and especially preferably from 1 to 12 carbon atoms; for example, mesyl and tosyl), a sulfinyl group (having preferably from 1 to 30 carbon atoms, more preferably from 1 to 20 carbon atoms, and especially preferably from 1 to 12 carbon atoms; for example, methane sulfinyl and benzene sulfinyl), a ureido group (having preferably from 1 to 30 carbon atoms, more preferably from 1 to 20 carbon atoms, and especially preferably from 1 to 12 carbon atoms; for example, ureido, methylureido, and phenylureido), a phosphoric amide group (having preferably from 1 to 30 carbon atoms, more preferably from 1 to 20 carbon atoms, and especially preferably from 1 to 12 carbon atoms; for example, diethylphosphoric amide and phenylphosphoric amide), a hydroxyl group, a mercapto group, a halogen atom (for example, a fluorine atom, a chlorine atom, a bromine atom, and an iodine atom), a sulfo group, a carboxyl group, a nitro group, a hydroxamic acid group, a sulfino group, a hydrazino group, an imino group, a heterocyclic group (inclusive of an aromatic heterocyclic group, which has preferably from 1 to 30 carbon atoms, and more preferably from 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, a silolyl group, a dibenzothiophenyl group and a dibenzofuranyl group), a silyl group (having preferably from 3 to 40 carbon atoms, more preferably from 3 to 30 carbon atoms, and especially preferably from 3 to 24 carbon atoms; for example, trimethylsilyl, and triphenylsilyl), a silyloxy group (having preferably from 3 to 40 carbon atoms, more preferably from 3 to 30 carbon atoms, and especially preferably from 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the further substituent include groups selected from the Substituent Group A as described above.

The substituent on a carbon atom is preferably an alkyl group, a perfluoroalkyl group, an aryl group, a heteroaryl group, a dialkylamino group, a diarylamino group, an alkoxy group, a cyano group, or a fluorine atom, more preferably an alkyl group or an aryl group, and especially preferably a methyl group or a phenyl group.

Preferably, $R^{111}$ and $R^{135}$ are each independently a hydrogen atom or bound to each other to form a ring, and more preferably a hydrogen atom.

$R^{112}$ and $R^{113}$ are preferably each independently a hydrogen atom or an alkyl group, and more preferably are both hydrogen atoms.

Preferably, $R^{114}$ and $R^{121}$ are each independently a hydrogen atom or bound to each other to form a ring, and more preferably a hydrogen atom.

$R^{122}$ to $R^{124}$ are preferably each independently a hydrogen atom, an alkyl group or an aryl group, more preferably a hydrogen atom or an aryl group, and especially preferably are all hydrogen atoms.

Preferably, $R^{125}$ and $R^{131}$ are each independently a hydrogen atom or bound to each other to form a ring, and more preferably a hydrogen atom.

$R^{132}$ to $R^{134}$ are preferably each independently a hydrogen atom, an alkyl group or an aryl group, more preferably a hydrogen atom or an aryl group, and especially preferably are all hydrogen atoms.

Preferred ranges of the substituents represented by $R^{111}$ to $R^{114}$, $R^{121}$ to $R^{125}$ and $R^{131}$ to $R^{135}$ are the same as the preferred ranges of the respective substituents in the Substituent Group A.

When two of $R^{111}$ to $R^{114}$, $R^{121}$ to $R^{125}$ and $R^{131}$ to $R^{135}$ are bound to each other to form a ring, the carbon atoms on which the respective substituents are substituted are preferably connected to each other via a single bond, O, S, $CR^{511}R^{512}$, $NR^{513}$, or $SiR^{514}R^{515}$ ($R^{511}$ to $R^{515}$ each independently represent a hydrogen atom or a substituent), more preferably connected via a single bond, O or S, especially preferably connected via O or S, and further especially preferably connected via O.

Examples of the substituents represented by $R^{511}$ and $R^{512}$, which are substituents on a carbon atom, include the Substituent Group A mentioned above.

Examples of the substituent represented by $R^{513}$, which is a substituent on a nitrogen atom, include the following Substituent Group B.

<<Substituent Group B>>

An alkyl group (having preferably from 1 to 30 carbon atoms, more preferably from 1 to 20 carbon atoms, and especially preferably from 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (having preferably from 2 to 30 carbon atoms, more preferably from 2 to 20 carbon atoms, and especially preferably from 2 to 10 carbon atoms; for example, vinyl, allyl, 2-butenyl, and 3-pentenyl), an alkynyl group (having preferably from 2 to 30 carbon atoms, more preferably from 2 to 20 carbon atoms, and especially preferably from 2 to 10 carbon atoms; for example, propargyl and 3-pentynyl), an aryl group (having preferably from 6 to 30 carbon atoms, more preferably from 6 to 20 carbon atoms, and especially preferably from 6 to 12 carbon atoms; for example, phenyl, p-methylphenyl, naphthyl, and anthranyl), a cyano group, and a heterocyclic group (inclusive of an aromatic heterocyclic group, which has preferably from 1 to 30 carbon atoms, and more preferably from 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, and a silolyl group). These substituents may be further substituted, and examples of the further substituent include groups selected from the Substituent Group B as described above.

The substituent on a nitrogen atom represented by $R^{513}$ is preferably an alkyl group, an aryl group, and an aromatic heterocyclic group, more preferably an aryl group, and especially preferably a phenyl group or a phenyl group substituted with a phenyl group (biphenyl group).

Preferred ranges of the substituents represented by $R^{514}$ and $R^{515}$, which are substituents on a silicon atom, are the same as the preferred ranges of the substituents represented by $R^{511}$ and $R^{512}$, which are substituents on a carbon atom.

In the general formula (1-1) to the general formula (1-3), $L^{111}$ to $L^{113}$ each independently represent O or S, and preferably O.

In the general formula (1-1) to the general formula (1-3), $L^{121}$ to $L^{123}$ each independently represent a single bond or a divalent linking group. $L^{121}$ to $L^{123}$ preferably each independently represent a single bond, phenylene group, a biphenylene group, an m-terphenylene group, a p-terphenylene group, —N(Ar')— (wherein, Ar' represents an aryl group, and a preferred range thereof is the same as the preferred range of the aryl group represented by $Ar^{111}$ to $Ar^{113}$), more preferably represent a single bond, a phenylene group, a biphenylene group, an m-terphenylene group or a p-terphenylene group, still more preferably a single bond, a phenylene group or biphenylene group, and especially preferably a single bond or phenylene group. When $L^{121}$ to $L^{123}$ each are a phenylene group, the phenylene group may be substituted with an amino group to form a phenyleneamino group, and $Ar^{123}$ to $Ar^{113}$ may be bound to this amino group. Such a material is preferred as a hole transporting material.

In addition, it is preferred to introduce a meta-linking phenylene group, biphenylene group or terphenylene group as at least one of $L^{121}$ to $L^{123}$ and after-mentioned $Ar^{123}$ to $Ar^{113}$, from the viewpoint of capability of reducing the overlapping of HOMO and LUMO, and thereby suppressing deterioration of the excited triplet state, resulting in making it possible for a green phosphorescence emitting material to emit light efficiently. It is more preferred that at least one of $L^{121}$ to $L^{123}$ and $Ar^{111}$ to $Ar^{113}$ contains an m-phenylene group.

In the general formula (1-1) to the general formula (1-3), $Ar^{111}$ to $Ar^{113}$ each independently represent an aryl group or a heteroaryl group, and from the viewpoint of durability, an aryl group is preferred.

An aryl group represented by each of $Ar^{111}$ to $Ar^{113}$ is preferably an aryl group having 6 to 30 carbon atoms, more preferably an aryl group having 6 to 20 carbon atoms, and especially preferably a phenyl group.

A heteroaryl group represented by each of $Ar^{111}$ to $Ar^{113}$ is preferably a heteroaryl group having 5 to 6 ring members, more preferably a heteroaryl group having 6 ring members, and especially preferably a triazyl group having 6 ring members. The hetero atoms constituting the heteroaryl group represented by $Ar^{111}$ to $Ar^{113}$ have no particular limitation, but it is preferred that a nitrogen atom is contained therein. Among them, the heteroaryl group represented by $Ar^{111}$ to $Ar^{113}$ is especially preferably a pyridyl group, a pyrimidyl group, or a triazyl group, and more especially preferably a triazyl group.

$Ar^{111}$ to $Ar^{113}$ may have a further substituent, and examples of the substituent include groups represented by the Substituent Group A mentioned above, and the substituent is preferably an alkyl group, an aryl group, a cyano group, or —$SiR^{461}R^{462}R^{463}$ ($R^{461}$, $R^{462}$, and $R^{463}$ each independently represent a hydrogen atom or a substituent, and examples of the substituent include groups represented by the Substituent Group A mentioned below. The substituent is preferably a hydrogen atom, an alkyl group, a cyano group or an aryl group, and more preferably a hydrogen atom, a cyano group or an aryl group, and especially preferably a hydrogen atom, a cyano group or an aryl group), and more preferably an aryl group or a cyano group, and especially preferably the substituent has at least one cyano group.

The further substituent on $Ar^{111}$ to $Ar^{113}$ may have a further substituent, and examples of the substituent include the same group as the further substituent on $Ar^{111}$ to $Ar^{113}$ or groups obtained by removing $Ar^{111}$ to $Ar^{113}$ respectively from the compounds represented by the general formula (1-1) to the general formula (1-3).

In the charge transporting material according to the present invention, it is preferred that $Ar^{111}$ to $Ar^{113}$ in the general formulae (1-1) to (1-3) are each independently a substituent represented by any one of the general formula (2-1) to the general formula (2-10).

General Formula (2-1)

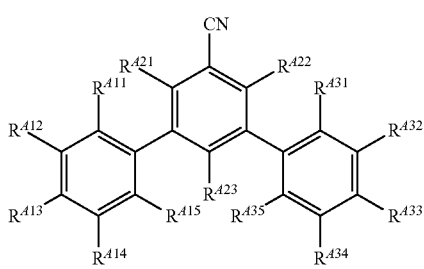

General Formula (2-2)

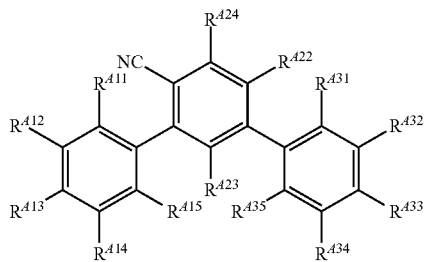

General Formula (2-3)

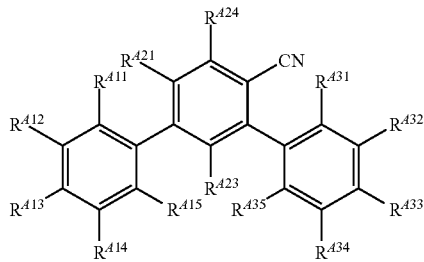

General Formula (2-4)

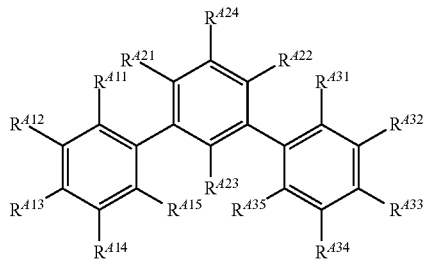

General Formula (2-5)

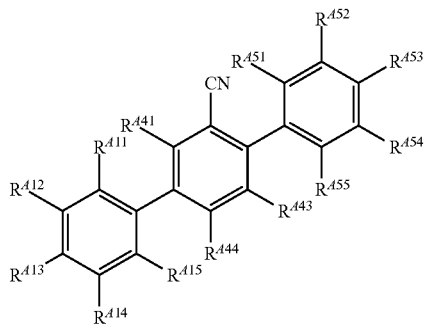

General Formula (2-6)

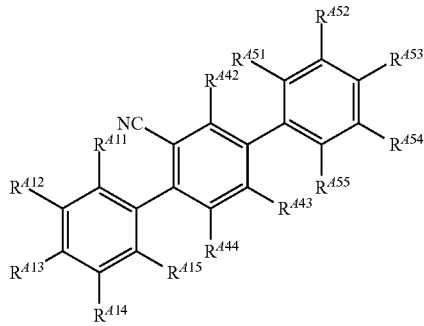

-continued

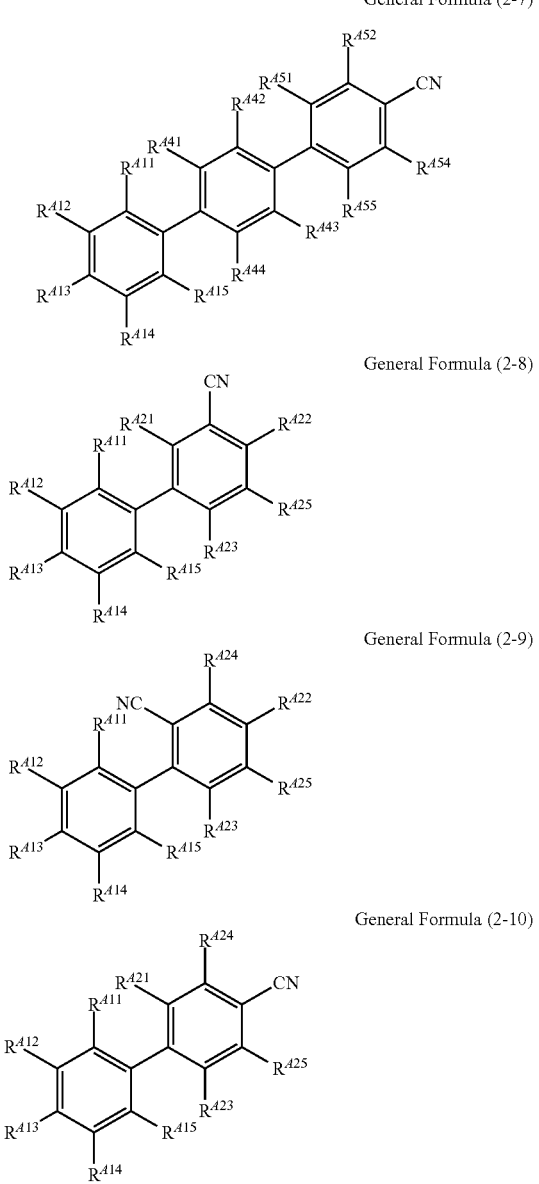

General Formula (2-7)

General Formula (2-8)

General Formula (2-9)

General Formula (2-10)

In the general formula (2-1) to the general formula (2-10), one of $R^{A11}$ to $R^{A15}$ represents a binding position to $L^{121}$ to $L^{123}$ in the general formulae (1-1) to (1-3), and the others thereof each independently represent a hydrogen atom or a substituent.

Among $R^{A11}$ to $R^{A15}$, the position of the group representing the binding position to $L^{121}$ to $L^{123}$ in the general formulae (1-1) to (1-3) is not particularly limited, but is preferably at $R^{A12}$ or $R^{A14}$ from the viewpoint of introducing a meta-linking phenylene group, biphenylene group or terphenylene group (preferably a m-phenylene group) into $Ar^{111}$ to $Ar^{113}$ to thereby allowing the green phosphorescence emitting material to emit light efficiently as described before. The binding position is more preferably at $R^{A12}$.

In the general formula (2-1) to the general formula (2-10), among $R^{A11}$ to $R^{A15}$, the groups other than the binding position to $L^{121}$ to $L^{123}$ in the general formulae (1-1) to (1-3) each independently represent a hydrogen atom or a substituent, more preferably a hydrogen atom or a group represented by the Substituent Group A, more preferably a hydrogen atom, an alkyl group, an aryl group or a cyano group, especially preferably a hydrogen atom, an alkyl group or a cyano group, and more especially preferably a hydrogen atom.

In the general formula (2-1) to the general formula (2-10), $R^{A21}$ to $R^{A25}$, $R^{A31}$ to $R^{A35}$, $R^{A41}$ to $R^{A45}$ and $R^{A51}$ to $R^{A55}$ each independently represent a hydrogen atom or a substituent, and examples of the substituent include groups represented by the Substituent Group A described above. Among them, the substituent is preferably a hydrogen atom, an alkyl group, a cyano group or an aryl group, more preferably a hydrogen atom, a cyano group or an aryl group, especially preferably a hydrogen atom or an aryl group, and especially preferably a hydrogen atom.

Among $R^{A21}$ to $R^{A25}$, $R^{A31}$ to $R^{A35}$, $R^{A41}$ to $R^{A45}$ and $R^{A51}$ to $R^{A55}$, it is also preferred that $R^{A33}$ has an aryl group from the viewpoint of forming a p-terphenylene structure to be preferably combined with the green phosphorescence emitting material. From the viewpoint of the driving voltage and durability, it is also preferred that $R^{A32}$ has a group obtained by removing $Ar^{111}$ to $Ar^{113}$ respectively from the compounds represented by the general formula (1-1) to the general formula (1-3).

In the general formula (2-1) to the general formula (2-10), however, the number of cyano group that is substituted on one benzene ring is preferably 0 to 2, and more preferably 0 or 1, and still more preferably, the number of benzene ring substituted with a cyano group is one.

In the general formula (2-1) to the general formula (2-10), preferred ranges of the substituents represented by $R^{A11}$ to $R^{A15}$, $R^{A21}$ to $R^{A25}$, $R^{A31}$ to $R^{A35}$, $R^{A41}$ to $R^{A45}$ and $R^{A51}$ to $R^{A55}$ are the same as the preferred ranges of the respective substituents in the description of the Substituent Group A.

Among them, in the charge transporting material according to the present invention, the substituents represented by the general formula (2-1) to the general formula (2-3) and the general formula (2-5) to the general formula (2-7) are preferred among the substituents represented by the general formula (2-1) to the general formula (2-10), from the viewpoint of the driving voltage and durability, and the substituents represented by the general formula (2-1), the general formula (2-2), the general formula (2-5) and the general formula (2-6) are more especially preferred from the viewpoint of the durability.

In the charge transporting material according to the present invention, $Ar^{111}$ to $Ar^{113}$ in the general formulae (1-1) to (1-3) are each independently a substituent represented by any one of the general formula (3-1) to the general formula (3-3).

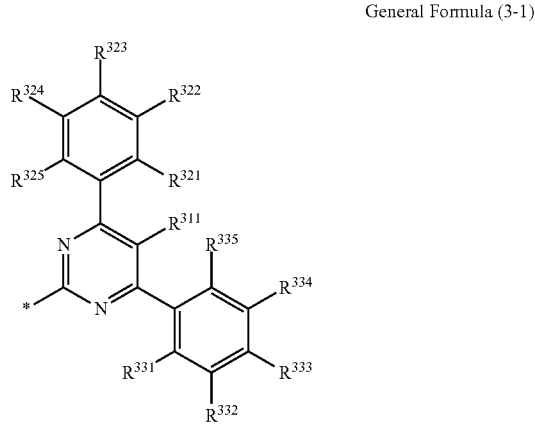

General Formula (3-1)

-continued

General Formula (3-2)

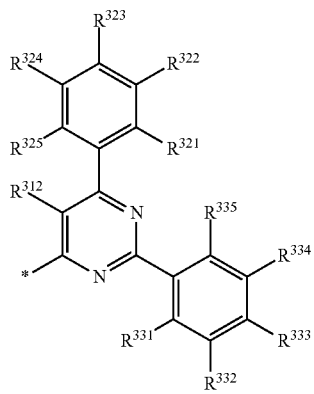

General Formula (4-1)

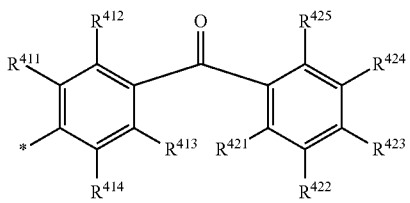

In the general formula (4-1), * represents a binding position to $L^{121}$ in the general formula (1-1).

In the general formula (4-1), $R^{411}$ to $R^{414}$ and $R^{421}$ to $R^{425}$ each independently represent a hydrogen atom or a substituent (examples of the substituent include the above-mentioned Substituent Group A), and more preferably a hydrogen atom or an aryl group. It is more preferred that $R^{423}$ is an aryl group and the others are hydrogen atoms.

In the general formula (4-1), preferred ranges of the substituents represented by $R^{411}$ to $R^{414}$ and $R^{421}$ to $R^{425}$ are the same as the preferred ranges of the respective substituents in the description of the Substituent Group A.

In the charge transporting material according to the present invention, $Ar^{111}$ to $Ar^{113}$ in the general formulae (1-1) to (1-3) are preferably the substituents represented by the general formulae (2-1) to (2-10) and the general formula (3-3) among the substituents represented by the general formula (2-1) to the general formula (2-10), the general formula (3-1) to the general formula (3-3) and the general formula (4-1), and more preferably the substituents represented by the general formula (2-1) to the general formula (2-3), and the general formula (2-5) to the general formula (2-7) from the viewpoint of the driving voltage, especially preferably the substituents represented by the general formula (2-1) to the general formula (2-3) and the general formula (2-5) to the general formula (2-7) from the viewpoint of the durability, and more especially preferably the substituents represented by the general formula (2-1), the general formula (2-2), the general formula (2-5) and the general formula (2-6) from the viewpoint of the durability.

General Formula (3-3)

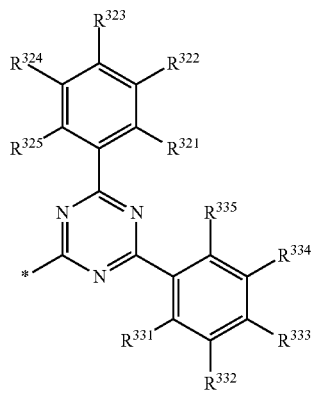

In the general formulae (3-1) to (3-3), * represents a binding position to $L^{121}$ to $L^{123}$ in the general formulae (1-1) to (1-3).

In the general formulae (3-1) to (3-3), $R^{311}$, $R^{312}$, $R^{321}$ to $R^{325}$ and $R^{331}$ to $R^{335}$ each independently represent a hydrogen atom or a substituent (examples of the substituent include the above-mentioned Substituent Group A), and more preferably a hydrogen atom or an aryl group. It is more preferred that at least one of $R^{323}$ and $R^{333}$ is an aryl group and the others are hydrogen atoms.

In the general formulae (3-1) to (3-3), preferred ranges of the substituents represented by $R^{311}$, $R^{312}$, $R^{321}$ to $R^{325}$ and $R^{331}$ to $R^{335}$ are the same as the preferred ranges of the respective substituents in the description of the Substituent Group A.

In the charge transporting material according to the present invention, the substituent represented by the general formula (3-3) is preferred among the substituents represented by the general formula (3-1) to the general formula (3-3) from the viewpoint of the driving voltage.

In the charge transporting material according to the present invention, it is also preferred that $Ar^{111}$ in the general formula (1-1) is a substituent represented by the following general formula (4-1).

The charge transporting material according to the present invention preferably includes a compound represented by the general formula (1-1) or the general formula (1-2) among the compounds represented by any of the general formula (1-1) to the general formula (1-3) from the viewpoint of the durability.

When the light emitting material is a phosphorescent material emitting green light, in the compounds represented by any of the general formula (1-1) to the general formula (1-3), the number of the single-ring aromatic ring having 6 ring members constituted of carbon atoms or nitrogen atoms that is connected at para-position is preferably not more than three. For example, when a further single-ring aromatic ring having 6 ring members constituted of carbon atoms or nitrogen atoms (such as a benzene ring) is connected to an end of a p-terphenylene group structure, the ring is preferably connected at the mete-position. When the light emitting material is a phosphorescence material emitting red light, the number of the single ring aromatic rings having 6 ring members constituted of carbon atoms or nitrogen atoms that is connected at para-position is preferably not more than 5, and more preferably not more than 4.

In the case where the compound represented by any one of the general formula (1-1) to the general formula (1-3) is used further in an organic layer of an organic electroluminescent element, a more preferred structure thereof is different depending on which function layer the compound is used in, among the organic layers. A more preferred structure of the compound represented by any one of the general formula (1-1) to the general formula (1-3) will be described later in the description of the organic electroluminescent element according to the present invention.

When the light emitting material is a phosphorescent material emitting green light, the $T_1$ energy in the film state of the compound represented by any one of the general formula (1-1) to the general formula (1-3) is preferably 56 kcal/mol to 80 kcal/mol, more preferably 57 kcal/mol to 70 kcal/mol, and still more preferably 58 kcal/mol to 66 kcal/mol. When the light emitting material is a phosphorescent material emitting red light, the $T_1$ energy in the film state of the compound represented by any one of the general formula (1-1) to the general formula (1-3) is preferably 47 kcal/mol to 80 kcal/mol, more preferably 48 kcal/mol to 70 kcal/mol, and still more preferably 49 kcal/mol to 66 kcal/mol. In particular, when a phosphorescence emitting material is used as the light emitting material, the $T_1$ energy is preferably within the above range.

By measuring a phosphorescence emission spectrum of a thin film of the material, the $T_1$ energy can be obtained from the end on the shorter wavelength side. For example, a film of the material is formed on a cleaned quarts glass substrate in a thickness of about 50 nm by a vacuum vapor deposition method, and a phosphorescence emission spectrum of the thin film is measured using Hitachi spectrofluorometer F-7000 (Hitachi High-Technologies Corporation) under a temperature of liquid nitrogen. The wavelength at the rising point of the obtained emission spectrum on the shorter wavelength side is converted to a value of an energy unit, thereby obtaining the $T_1$ energy.

In the charge transporting material according to the present invention, a molecular weight of the compound represented by any one of the general formula (1-1) to the general formula (1-3) is preferably 1000 or less, more preferably 500 to 1000, and especially preferably 600 to 900. This range of the molecular weight can provide a material which provides a good film quality and is excellent in suitability to sublimation purification and vapor deposition. In particular, it is preferred that the compound represented by any one of the general formula (1-1) to the general formula (1-3) has a molecular weight of 600 to 1000 from the viewpoint of the suitability to vapor deposition.

From the viewpoint of operating the organic electroluminescent element stably during driving at a high temperature or stably against the heat generation during driving the element, the compound represented by any one of the general formula (1-1) to the general formula (1-3) preferably has a glass transition temperature (Tg) of 80° C. to 400° C., more preferably 100° C. to 400° C., still more preferably 120° C. to 400° C.

When the purity of the compound represented by any one of the general formula (1-1) to the general formula (1-3) is low, since the impurities may act as a trap in a charge transport or promote deterioration of the element, it is preferred that the purity of the compound represented by any one of the general formula (1-1) to the general formula (1-3) is as high as possible. The purity can be measured, for example, with a high performance liquid chromatography (HPLC), and the area ratio of the compound represented by any one of the general formula (1-1) to the general formula (1-3) when detected at an optical absorption intensity of 254 nm is preferably 99.00% or more, more preferably 99.50% or more, especially preferably 99.90% or more, and most preferably 99.9% or more.

As known in a carbazole-based material disclosed in WO 2008/117889, a material of a compound obtained by substituting a part or all of hydrogen atoms in the compound represented by any one of the general formula (1-1) to the general formula (1-3) with deuterium atoms can also be preferably used as a charge transporting material.

Specific examples of the compound represented by any one of the general formula (1-1) to the general formula (1-3) are shown below, but the present invention is not limited thereto.

Compound (1-1-1)

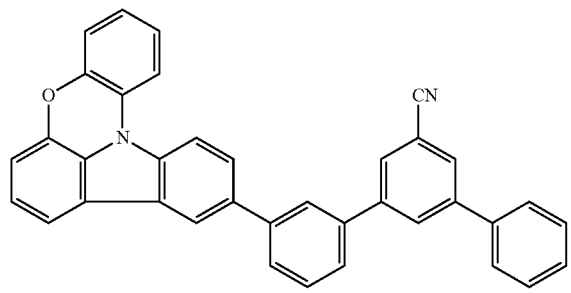

Compound (1-1-2)

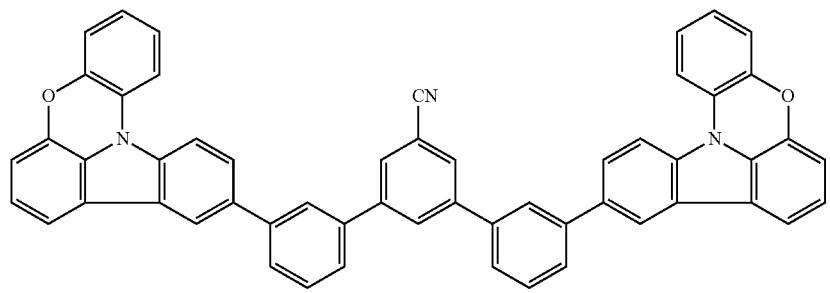

-continued
Compound (1-1-3)
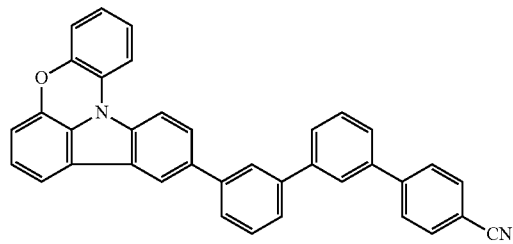
Compound (1-1-4)
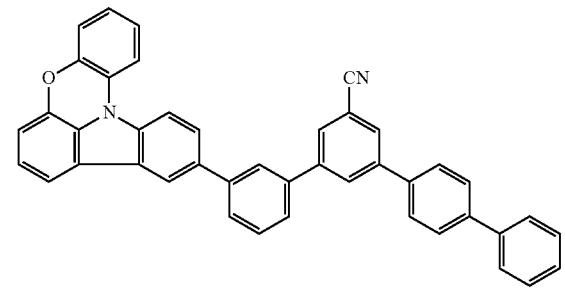
Compound (1-1-5)
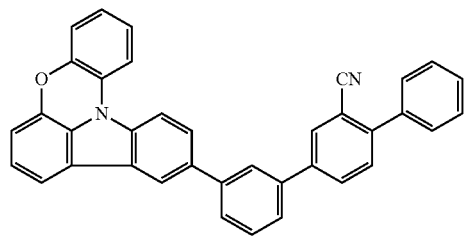
Compound (1-1-6)
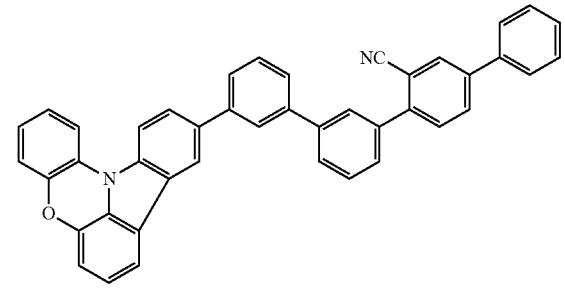
Compound (1-1-7)
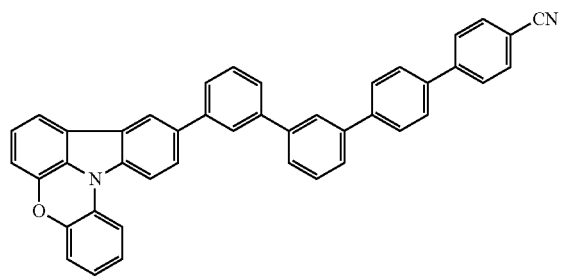
Compound (1-1-8)
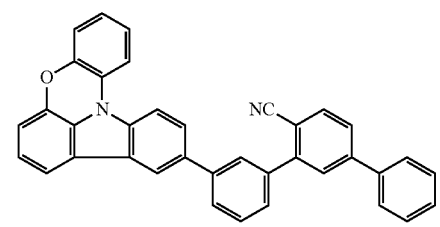
Compound (1-1-9)
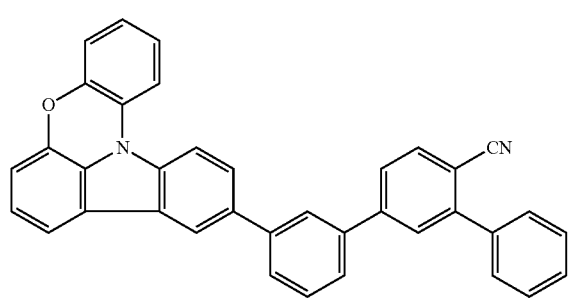
Compound (1-1-10)
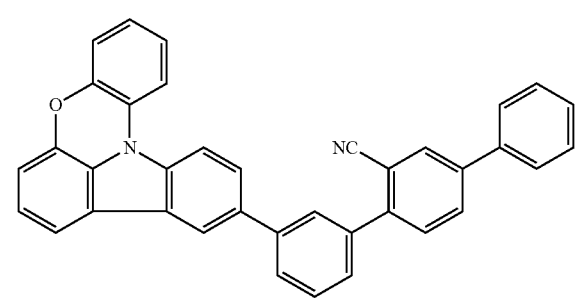
Compound (1-1-11)
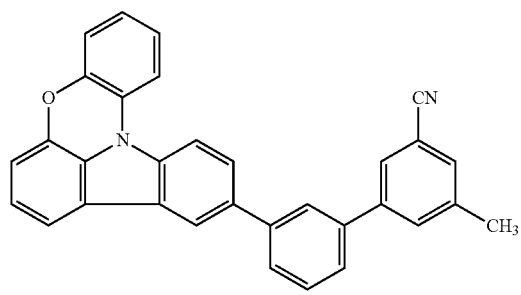
Compound (1-1-12)
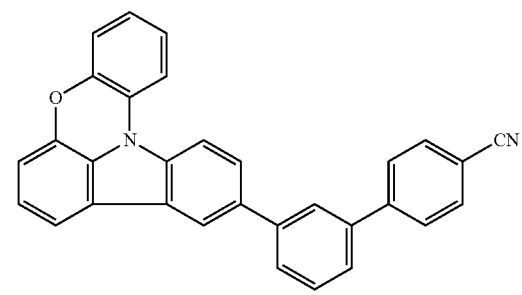

-continued
Compound (1-1-13)
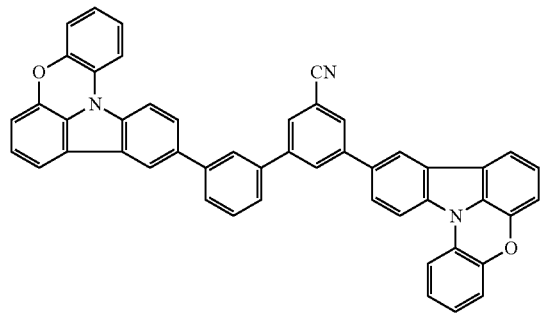
Compound (1-1-14)
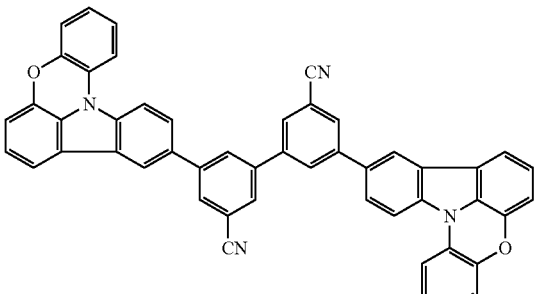
Compound (1-1-15)
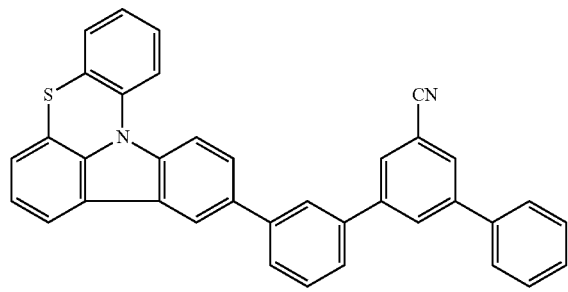
Compound (1-1-16)
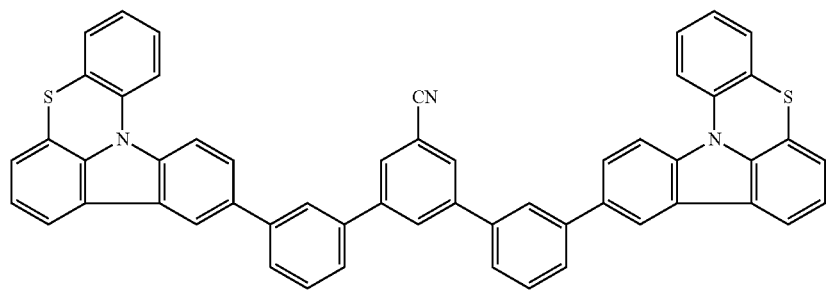
Compound (1-1-17)
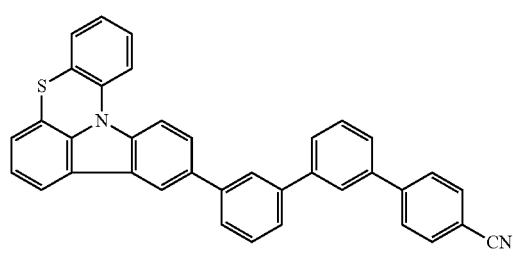
Compound (1-1-18)
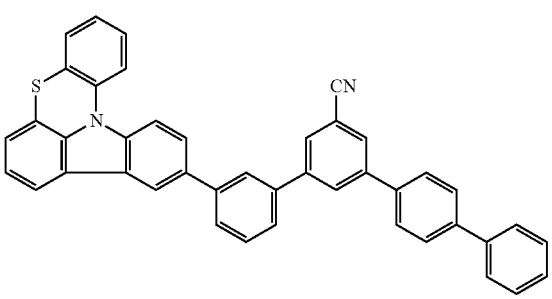
Compound (1-1-19)
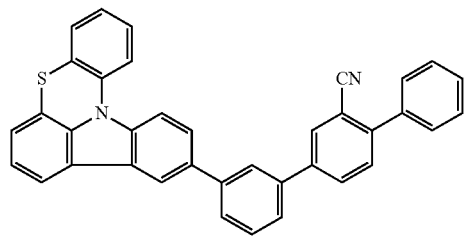
Compound (1-1-20)
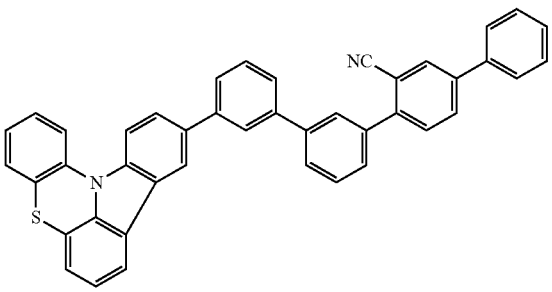

-continued
Compound (1-1-21)
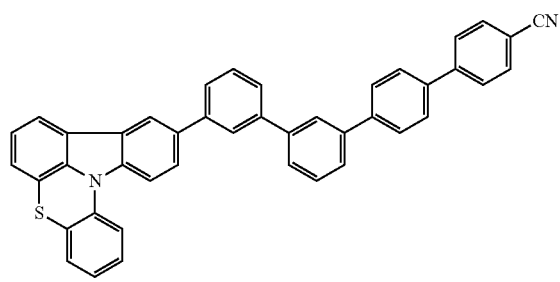
Compound (1-1-22)
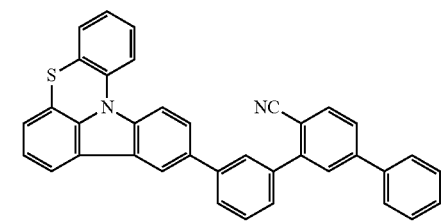
Compound (1-1-23)
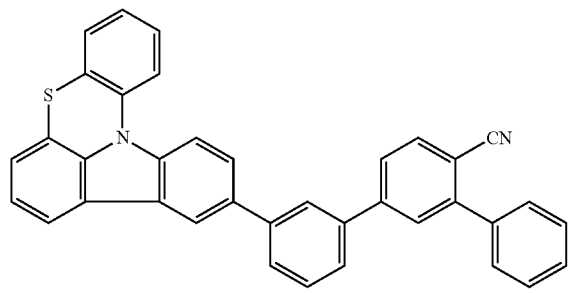
Compound (1-1-24)
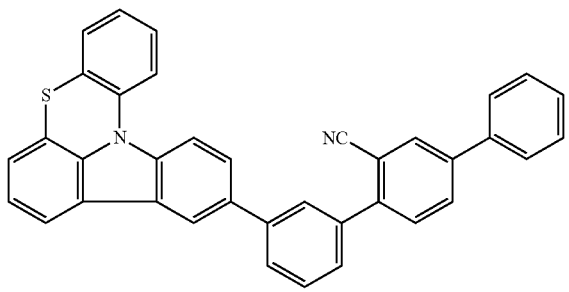
Compound (1-1-25)
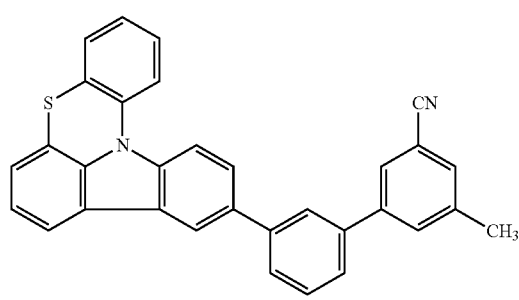
Compound (1-1-26)
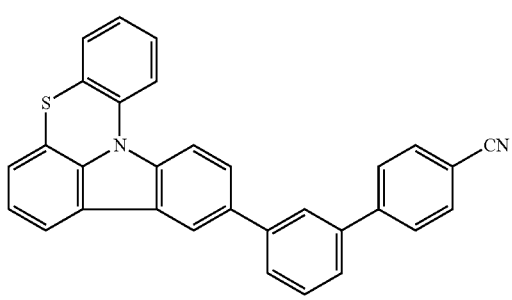
Compound (1-1-27)
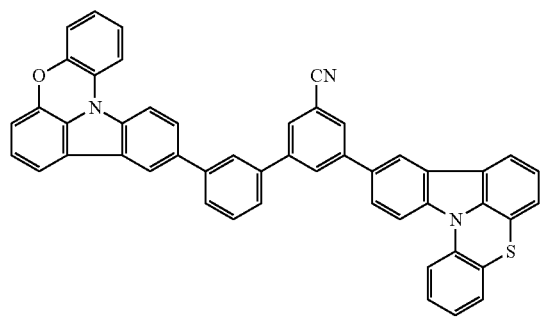
Compound (1-1-28)
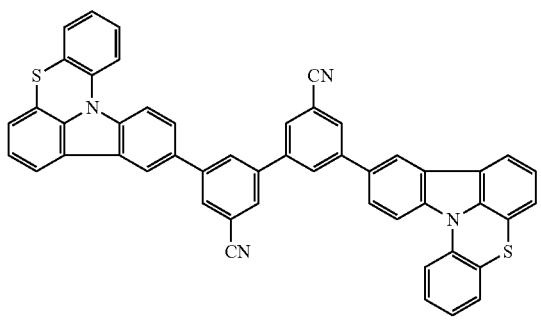
Compound (1-2-1)
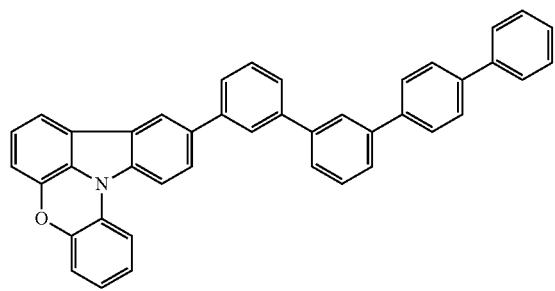
Compound (1-2-2)
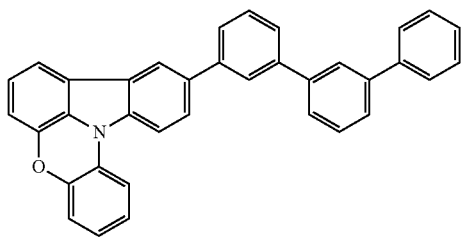

-continued
Compound (1-2-3)
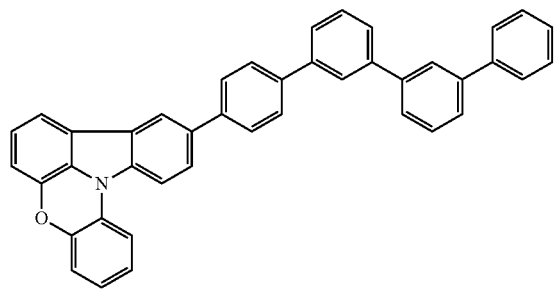
Compound (1-2-4)
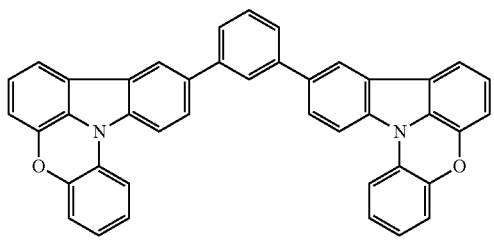
Compound (1-2-5)
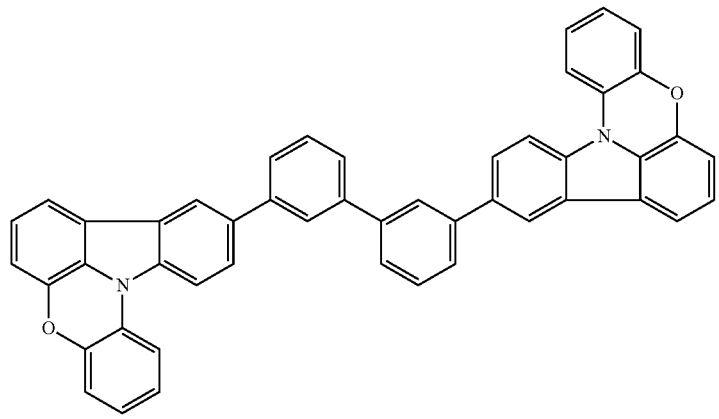
Compound (1-2-6)
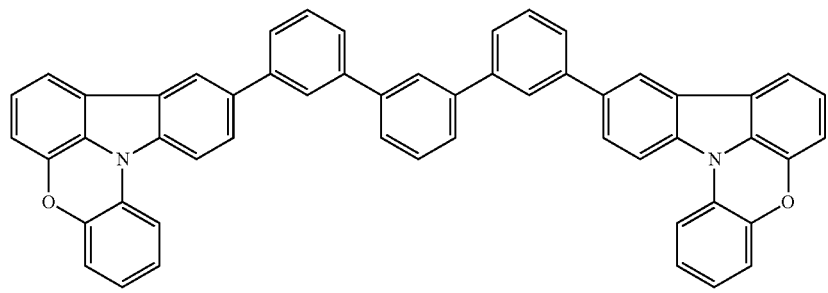
Compound (1-2-7)
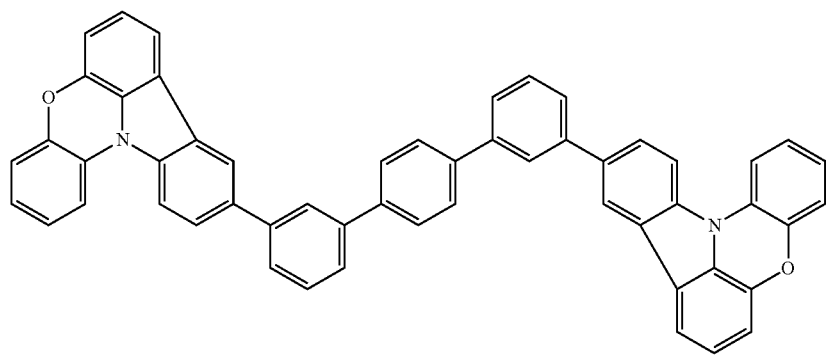
Compound (1-2-8)
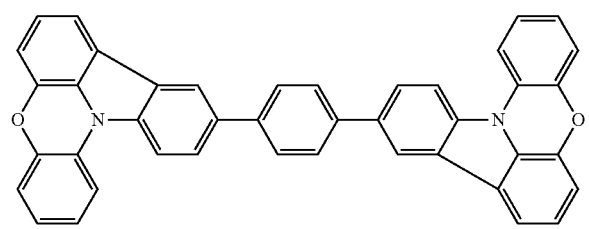
Compound (1-2-9)
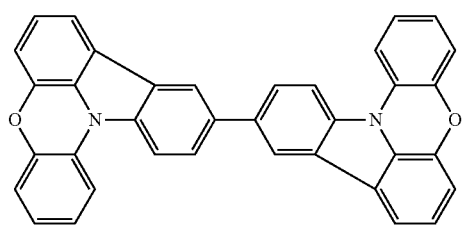

-continued
Compound (1-2-10)
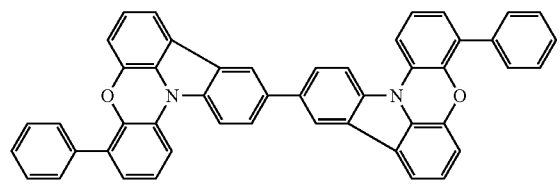
Compound (1-2-11)
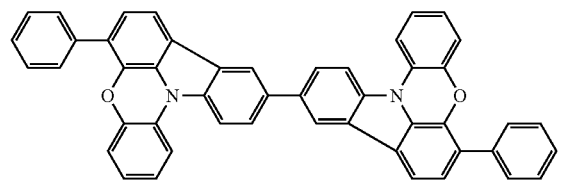
Compound (1-2-12)
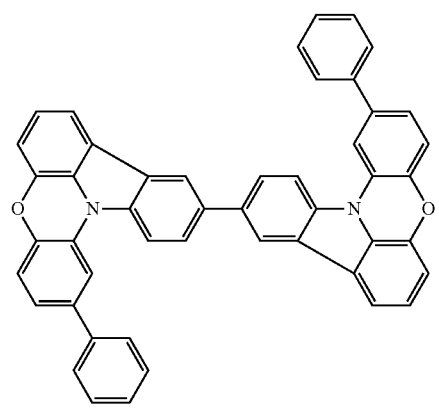
Compound (1-2-13)
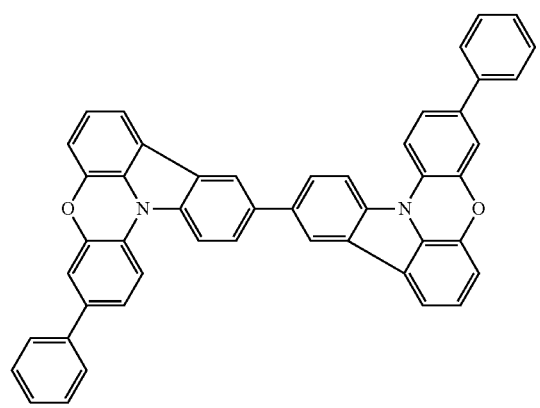
Compound (1-2-14)
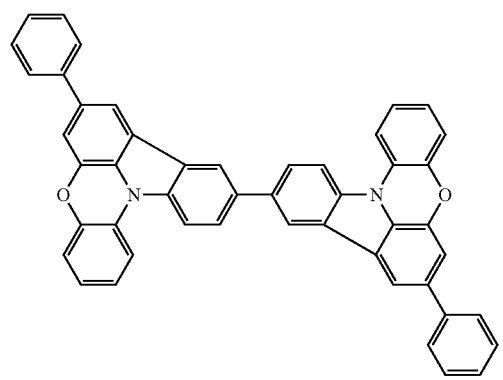
Compound (1-2-15)
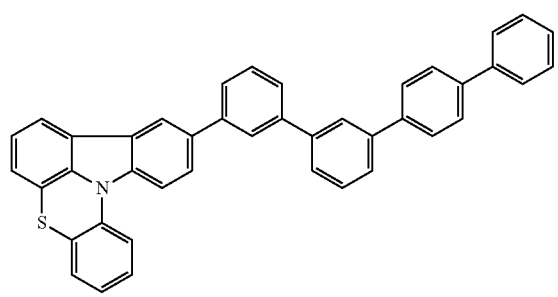
Compound (1-2-16)
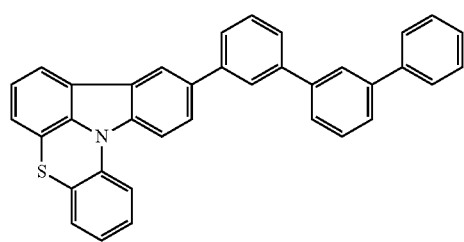
Compound (1-2-17)
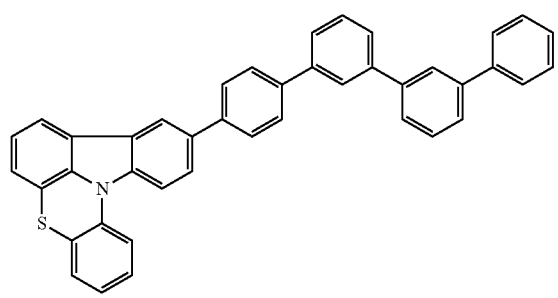

Compound (1-2-18)
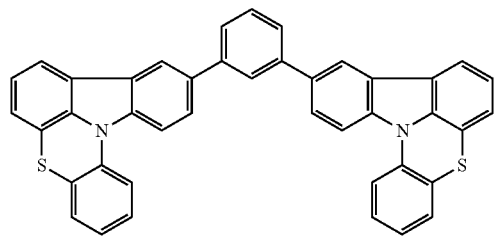
Compound (1-2-19)
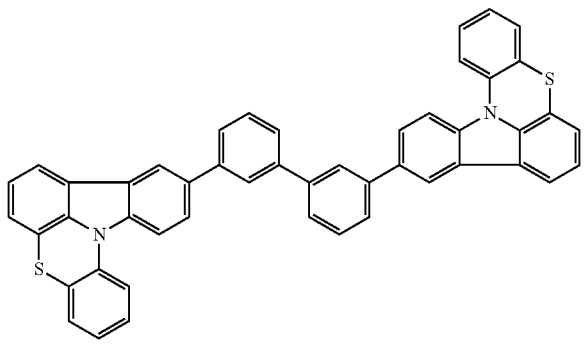
Compound (1-2-20)
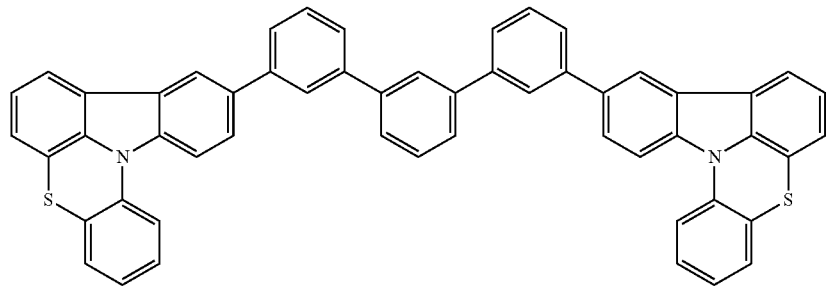
Compound (1-2-21)
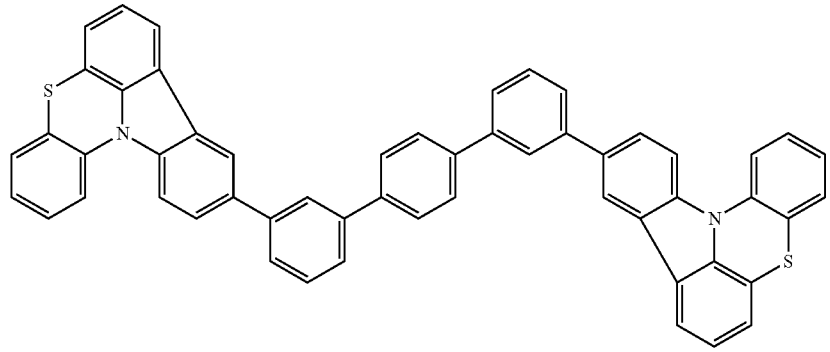
Compound (1-2-22)
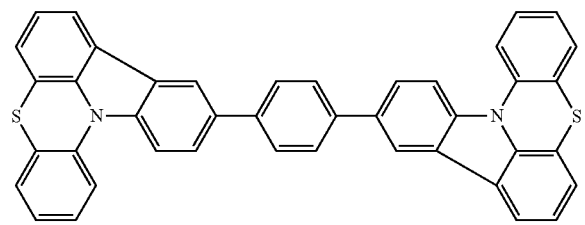
Compound (1-2-23)
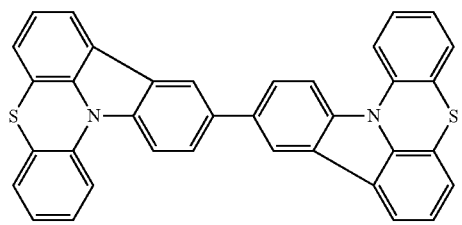
Compound (1-2-24)
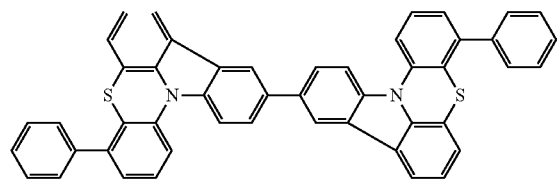
Compound (1-2-25)
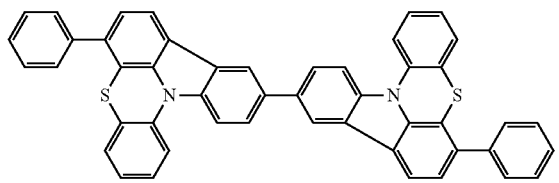

-continued
Compound (1-2-26)
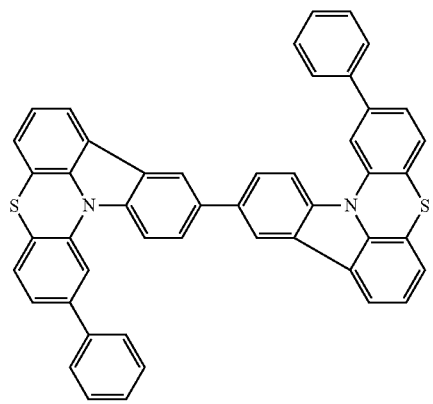
Compound (1-2-27)
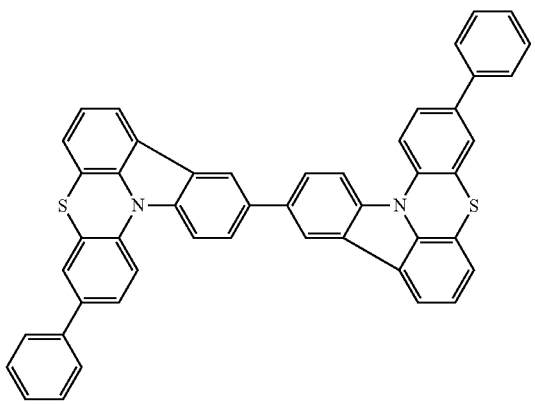
Compound (1-2-28)
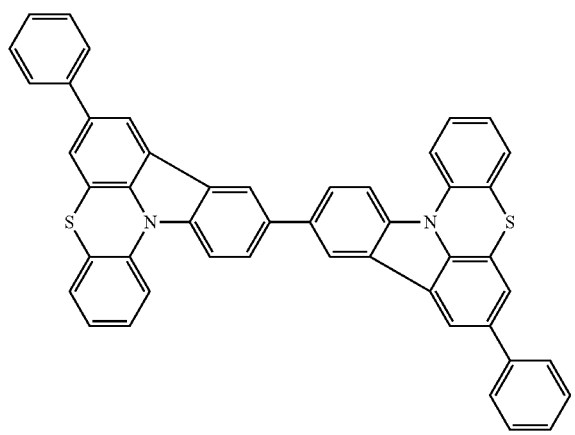
Compound (1-2-29)
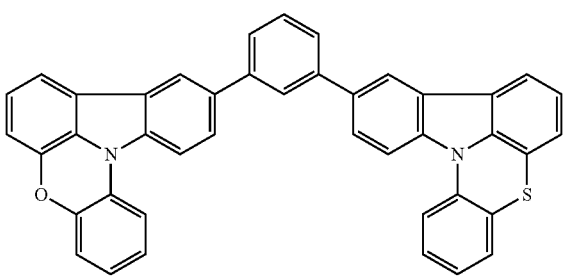
Compound (1-2-30)
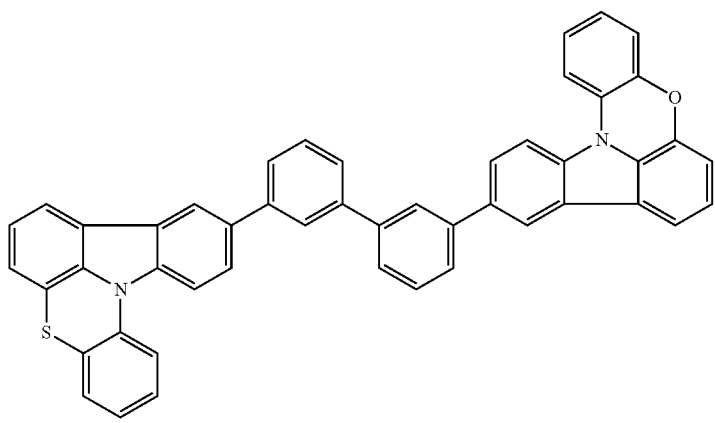

Compound (1-2-29)
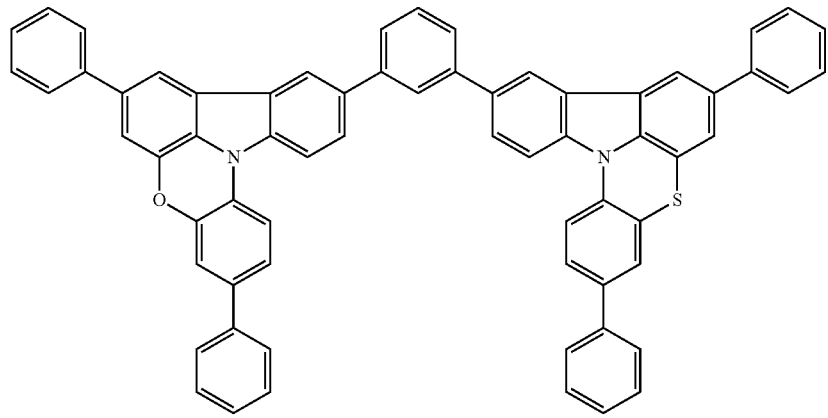
Compound (1-2-30)　　　Compound (1-2-31)
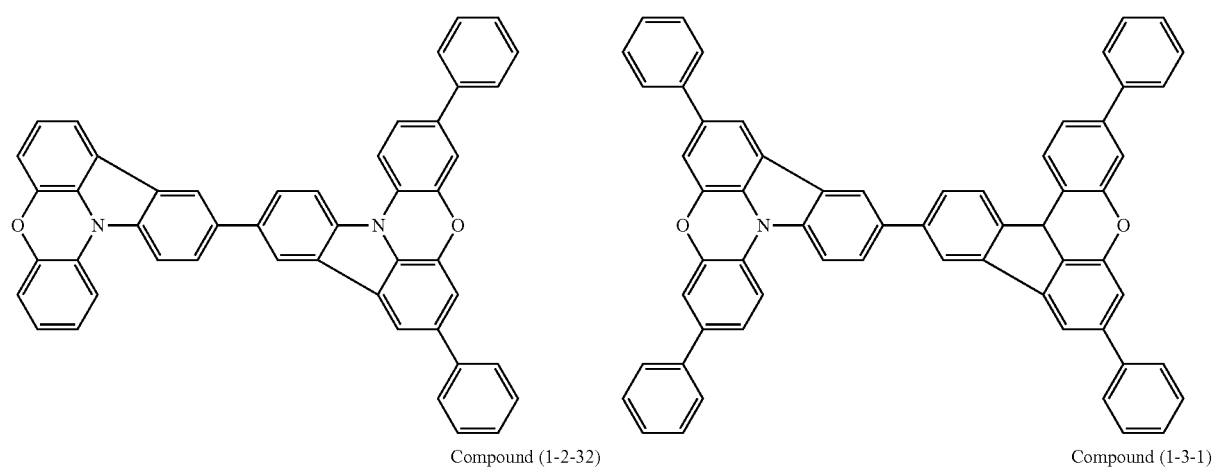
Compound (1-2-32)　　　Compound (1-3-1)
Compound (1-3-2)　　　Compound (1-3-3)
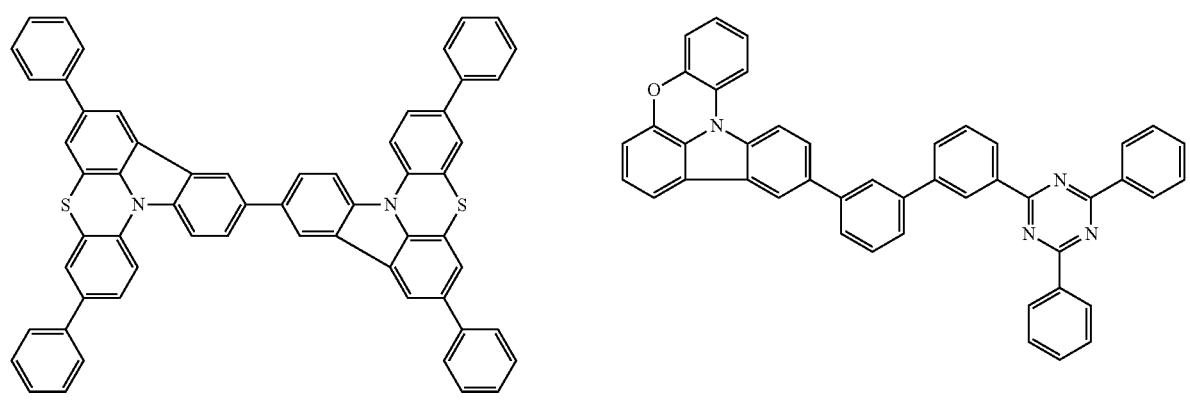
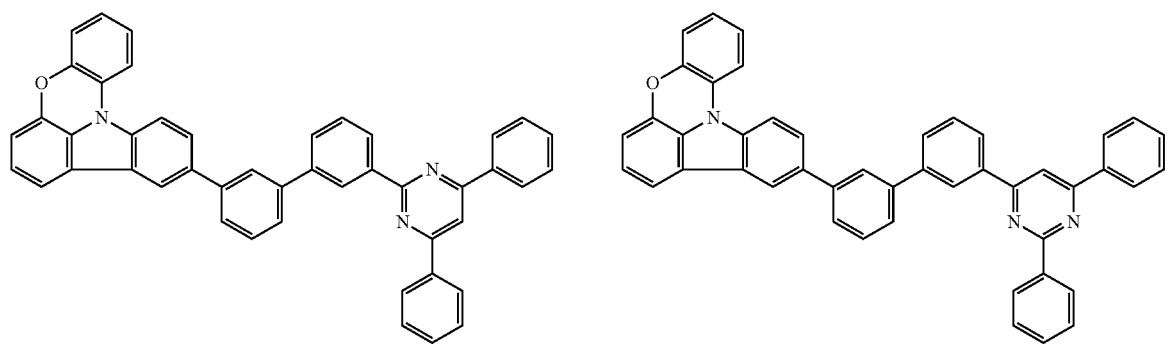

Compound (1-3-4)
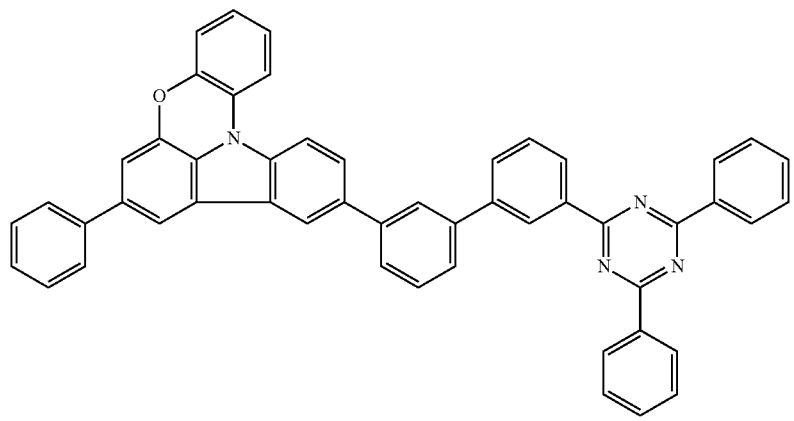
Compound (1-3-5)
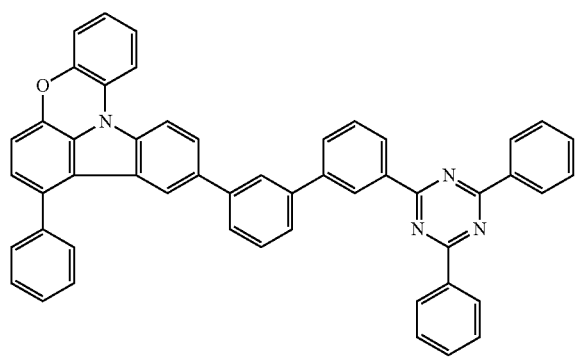
Compound (1-3-6)
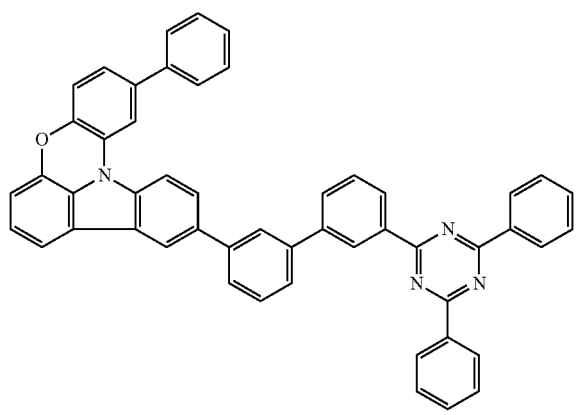
Compound (1-3-7)
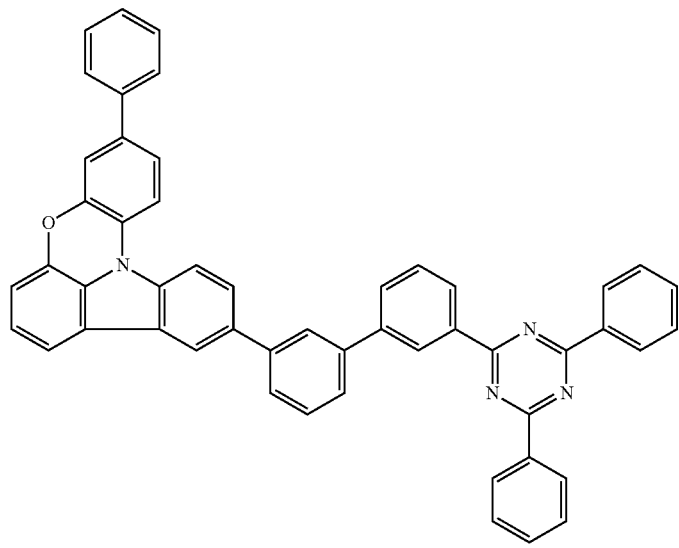

-continued
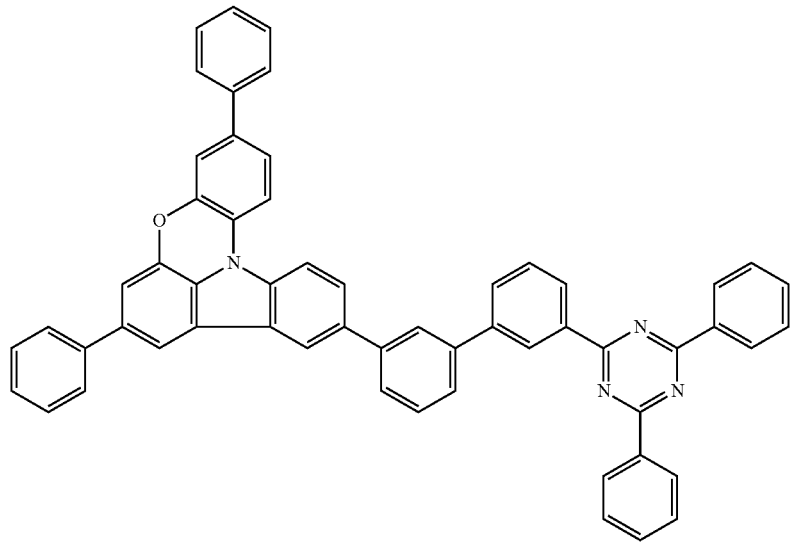
Compound (1-3-8)
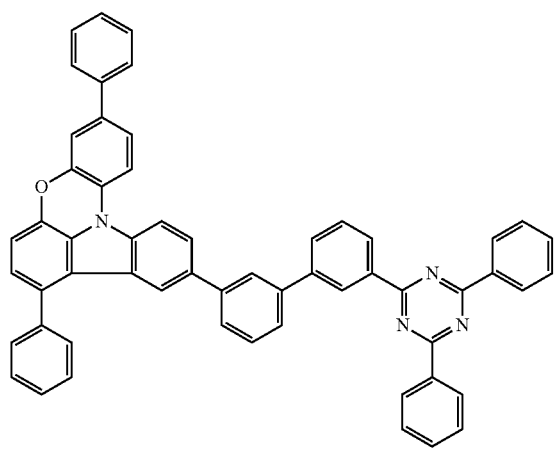
Compound (1-3-9)
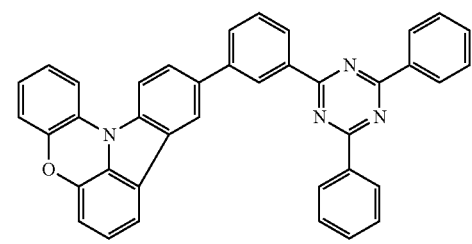
Compound (1-3-10)
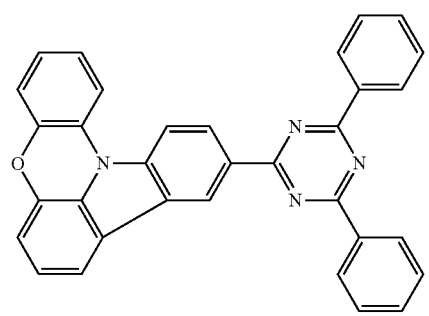
Compound (1-3-11)
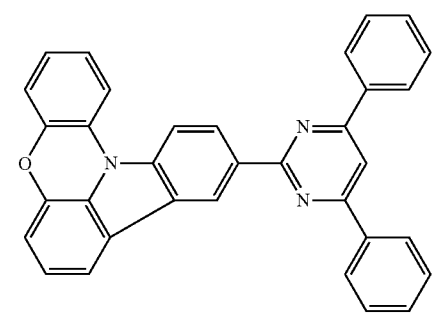
Compound (1-3-12)
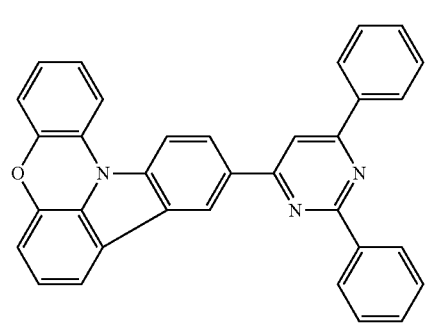
Compound (1-3-13)
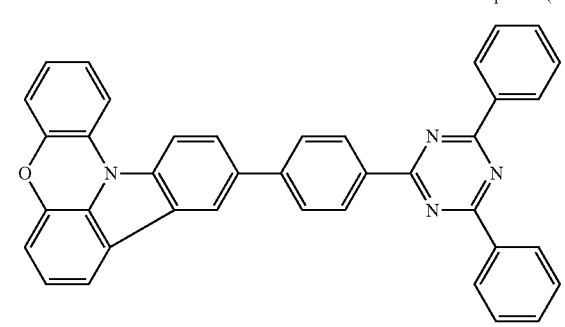
Compound (1-3-14)

-continued
Compound (1-3-15)
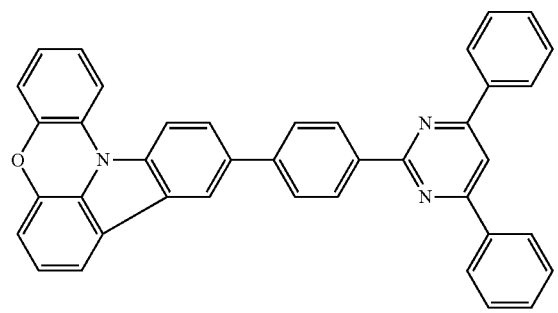
Compound (1-3-16)
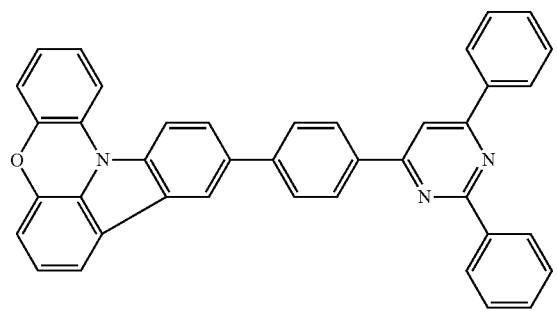
Compound (1-4-1)
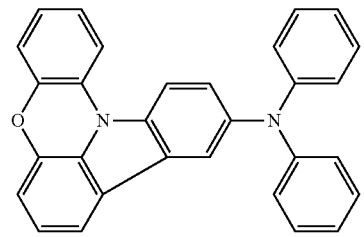
Compound (1-4-2)
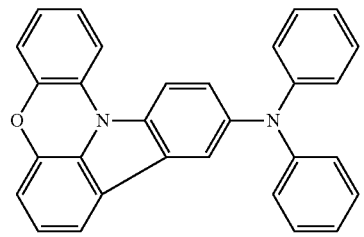
Compound (1-4-3)
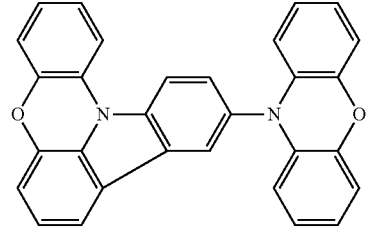
Compound (1-4-4)
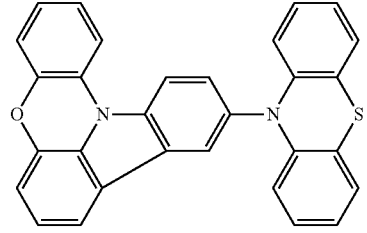
Compound (1-4-5)
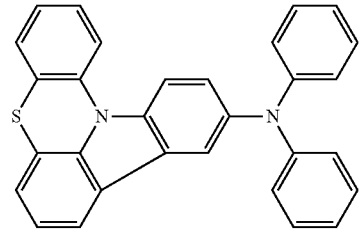
Compound (1-4-6)
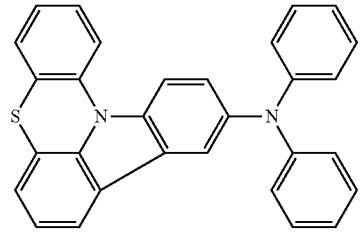
Compound (1-4-7)
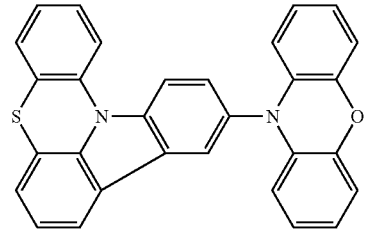
Compound (1-4-8)
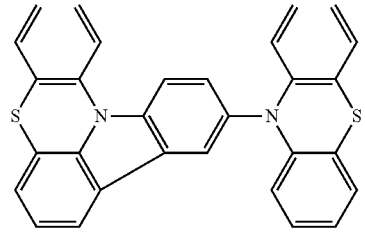
Compound (1-4-9)
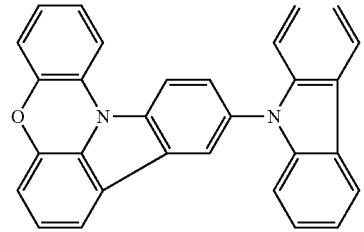
Compound (1-4-10)
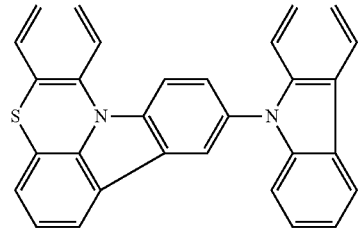

-continued
Compound (1-4-11)
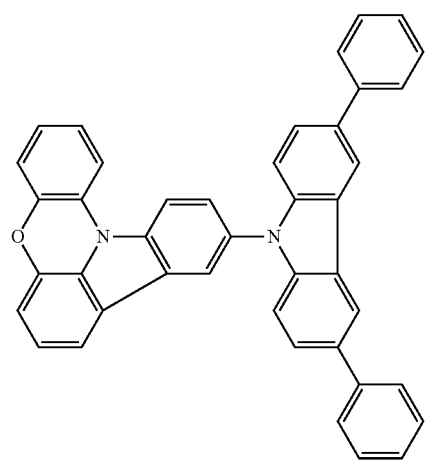
Compound (1-4-12)
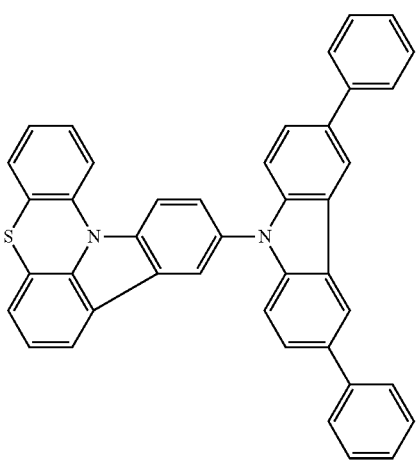
Compound (1-5-1)
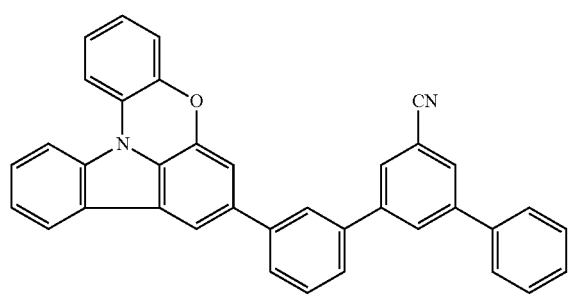
Compound (1-5-2)
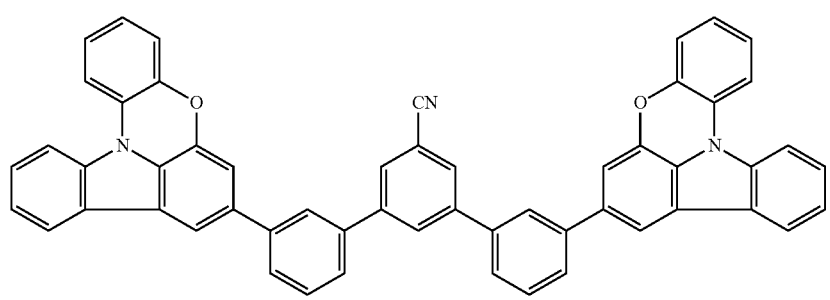
Compound (1-5-3)
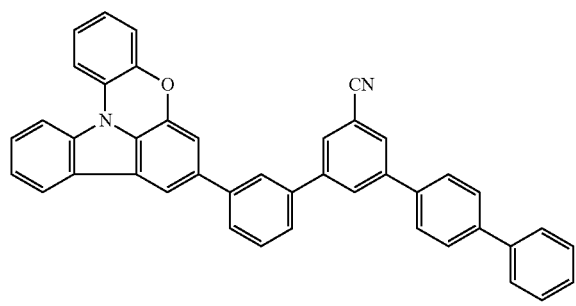
Compound (1-5-4)
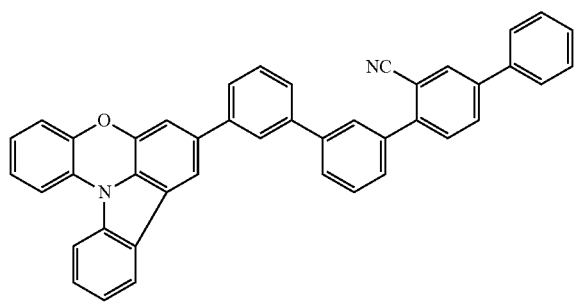

-continued
Compound (1-5-5) Compound (1-5-6)
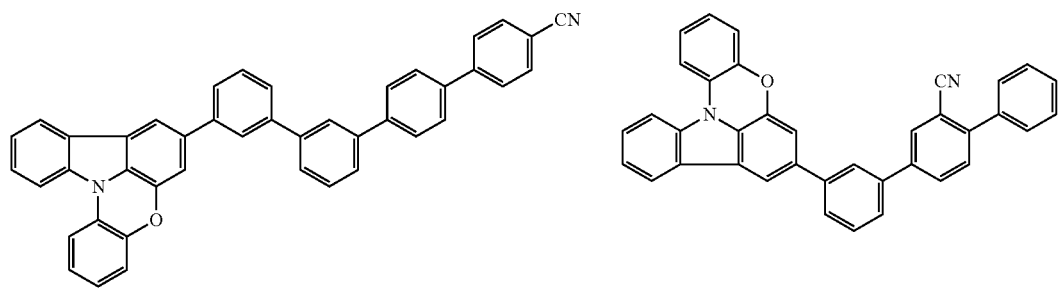
Compound (1-5-7)
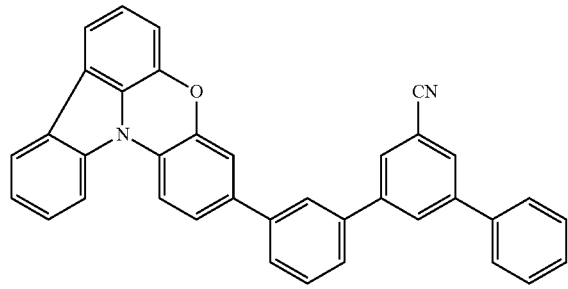
Compound (1-5-8)
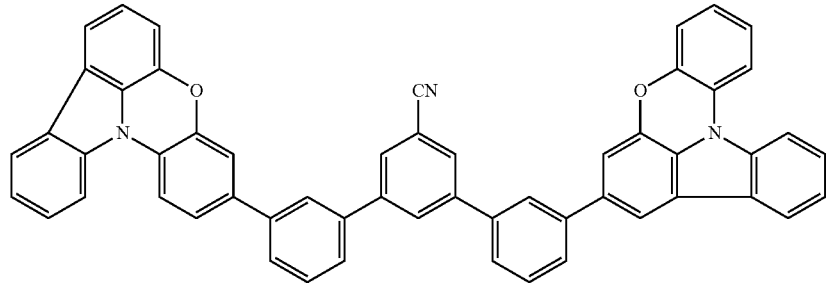
Compound (1-5-9) Compound (1-5-10)
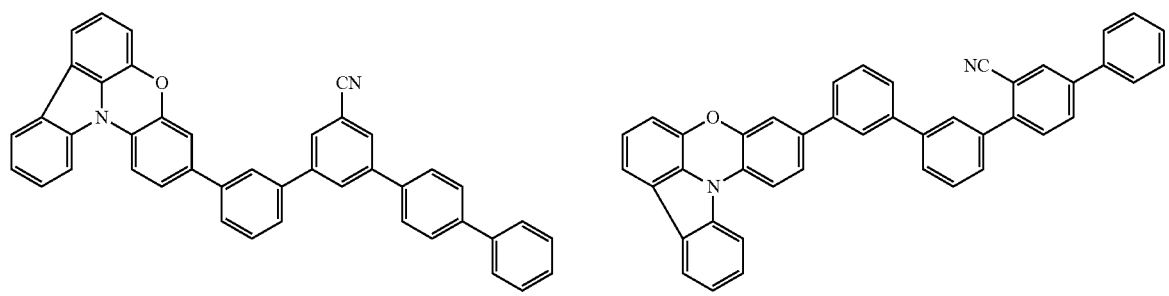
Compound (1-5-11) Compound (1-5-12)
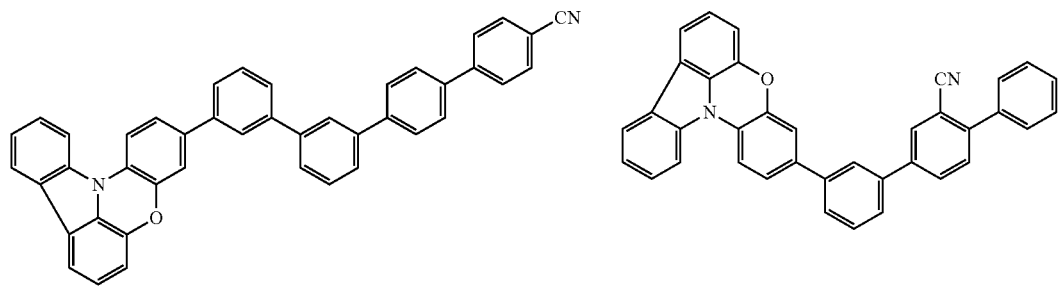

-continued
Compound (1-5-13)
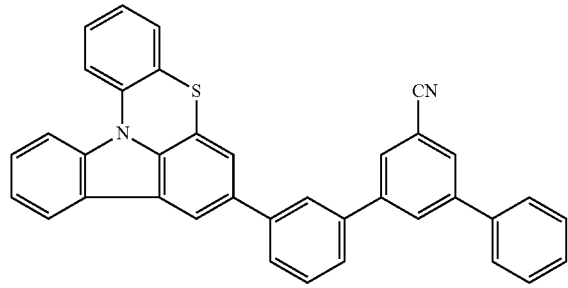
Compound (1-5-14)
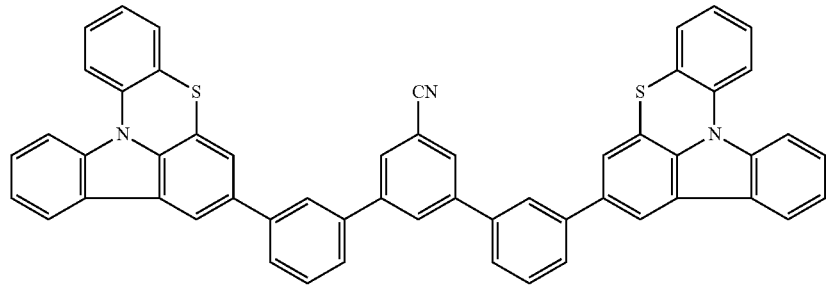
Compound (1-5-15)
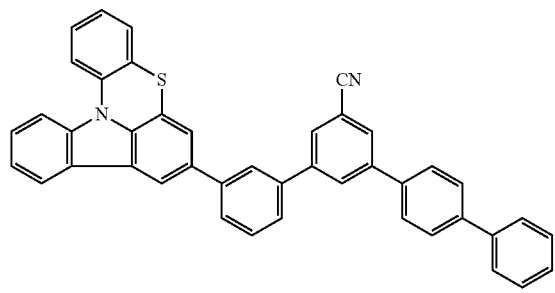
Compound (1-5-16)
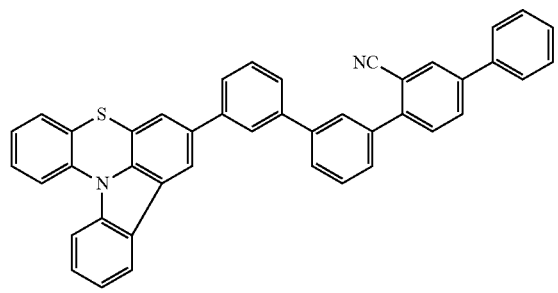
Compound (1-5-17)
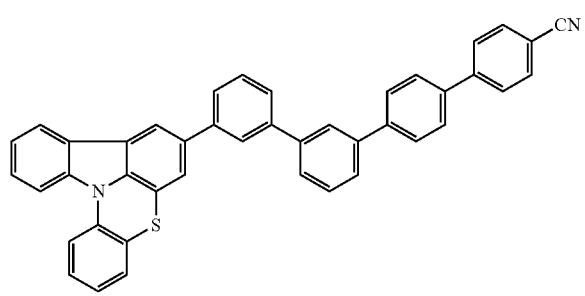
Compound (1-5-18)
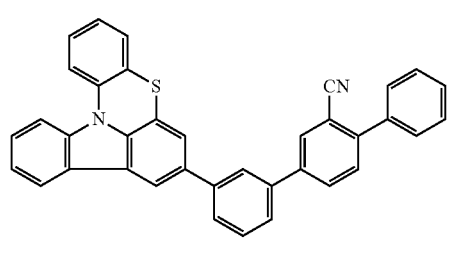
Compound (1-5-19)
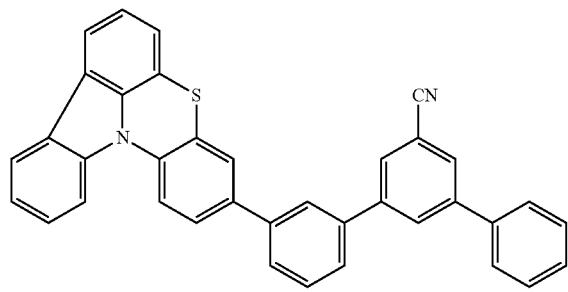

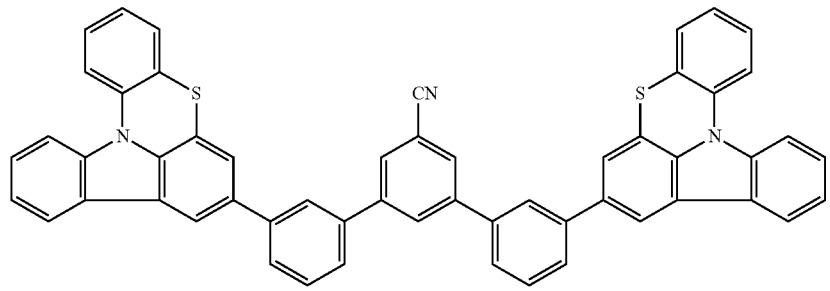

Compound (1-5-20)

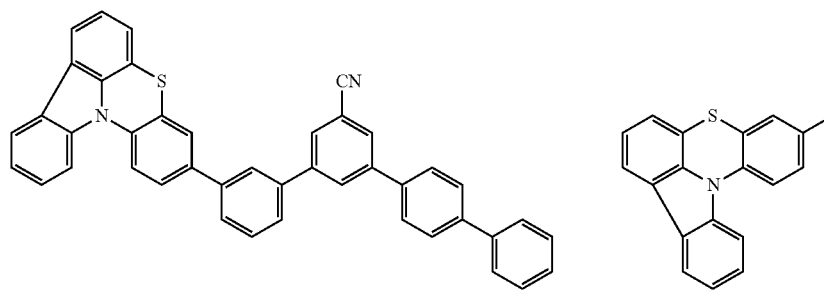

Compound (1-5-21)　　　　Compound (1-5-22)

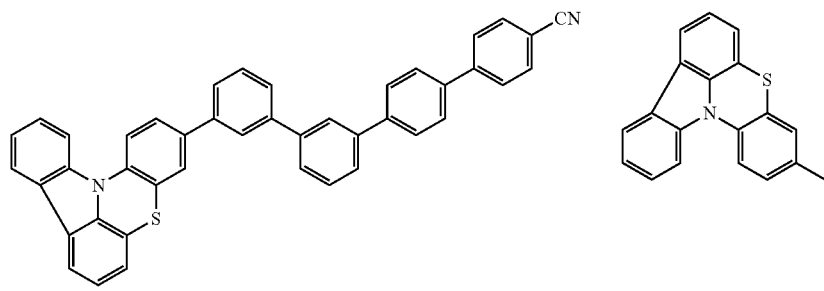

Compound (1-5-23)　　　　Compound (1-5-24)

The compound represented by any one of the general formula (1-1) to the general formula (1-3) can be synthesized by any method disclosed in JP-A-2007-266598, JP-A-2011-233603, etc., or any combination of the other known reactions.

It is preferred that after the synthesis, the compound is purified by column chromatography, recrystallization, or the like, and thereafter purified by sublimation purification. By sublimation purification, it is possible not only to separate organic impurities but also to effectively remove the inorganic salts, remaining solvent, or the like.

[Organic Electroluminescent Element]

The organic electroluminescent element according to the present invention includes a substrate; a pair of electrodes including an anode and a cathode, disposed on the substrate; and an organic layer disposed between the electrodes, and is characterized in that the organic layer contains at least one compound represented by any one of the general formula (1-1) to the general formula (1-3).

The configuration of the organic electroluminescent element according to the present invention is not particularly limited. FIG. 1 shows an example of the configuration of the organic electroluminescent element according to the present invention. The organic electroluminescent element 10 in FIG. 1 includes organic layers between a pair of electrodes (an anode 3, and a cathode 9) on a substrate 2.

The configuration of the element, the substrate, the anode and the cathode, of the organic electroluminescent element are described in detail, for example, in JP-A-2008-270736, and the matters described in the patent publication can be applied to the present invention.

Preferred embodiments of the organic electroluminescent element according to the present invention are hereunder described, in the order of the substrate, electrode, organic layer, protective layer, sealing enclosure, driving method, emission peak wavelength, and application thereof.

<Substrate>

The organic electroluminescent element according to the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Electrodes>

The organic electroluminescent element according to the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes to an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.
(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.
<Organic Layer>

The organic electroluminescent element according to the present invention includes (an) organic layer(s) disposed between the electrodes, and is characterized by the organic layer(s) containing at least one compound represented by any one of the general formula (1-1) to the general formula (1-3). The organic layer(s) preferably include(s) a phosphorescence emitting material and the compound represented by any one of the general formula (1-1) to the general formula (1-3).

The organic layer is not particularly limited, and may be appropriately selected according to the intended use and purpose of the organic electroluminescent element, and is preferably formed on the transparent electrode or the semi-transparent electrode. In this case, the organic layer is formed on the whole or a part of the surface of the transparent electrode or the semi-transparent electrode.

The shape, size and thickness of the organic layer are not particularly limited, and may be appropriately selected according to the intended purpose.

The configuration of the organic layers, the method of forming the organic layer, preferred aspects of each layer constituting the organic layers, and the material used in each layer, in the organic electroluminescent element according to the present invention are explained in turn bellow.
(Configuration of Organic Layers)

In the organic electroluminescent element according to the present invention, the organic layers preferably include a charge transporting layer.

The charge transporting layer means a layer in which charge transfer occurs when a voltage is applied to the organic electroluminescent element.

Specifically, examples of the charge transporting layer include a hole injecting layer, a hole transporting layer, an electron blocking layer, a light emitting layer, a hole blocking layer, an electron transporting layer and an electron injecting layer. The charge transporting layer is preferably a hole injecting layer, a hole transporting layer, an electron blocking layer or a light emitting layer. When a charge transporting layer formed by a coating method is a hole injecting layer, a hole transporting layer, an electron blocking layer or a light emitting layer, it becomes possible to manufacture an organic electroluminescent element of high efficiency with a low cost. The charge transporting layer is more preferably a hole injecting layer, a hole transporting layer or an electron blocking layer.

In the organic electroluminescent element according to the present invention, however, even when the organic layers include a light emitting layer and other organic layers, the layers are not always required to be clearly distinguished from one another.

In the organic electroluminescent element according to the present invention, the organic layers preferably contain a phosphorescence emitting material and the compound represented by any one of the general formula (1-1) to the general formula (1-3). In this case, the locations where the phosphorescence emitting material and the compound represented by any one of the general formula (1-1) to the general formula (1-3) are contained are not particularly limited. In the present invention, it is more preferred that the organic layers include a light emitting layer containing the phosphorescence emitting material and other organic layers, and the light emitting layer contains the compound represented by any one of the general formula (1-1) to the general formula (1-3). In this case, it is preferred that the compound represented by any one of the general formula (1-1) to the general formula (1-3) is used as a host material (hereinafter, sometimes referred to as a host compound) of the light emitting layer.

In the present invention, the compound represented by any one of the general formula (1-1) to the general formula (1-3) is not limited in its use, and may be contained in any layer of the organic layers between the cathode and the anode of the organic electroluminescent element. The layer in which the compound represented by any one of the general formula (1-1) to the general formula (1-3) is introduced is preferably the light emitting layer, a layer between the light emitting layer and the cathode, or a layer between the light emitting layer and the anode, and the compound may be contained in one layer or plural layers thereof. The compound is more preferably contained in any one of the light emitting layer, a hole injecting layer, a hole transporting layer, an electron transporting layer, an electron injecting layer, an exciton blocking layer and a charge blocking layer (a hole blocking layer, an electron blocking layer, etc.) or in plural layers thereof, especially preferably contained in anyone of the light emitting layer, an exciton blocking layer, a charge blocking layer, an electron transporting layer and an electron injecting layer, and more especially preferably contained in the light emitting layer or a hole blocking layer.

In the present invention, the compound represented by any one of the general formula (1-1) to the general formula (1-3) is preferably contained in the light emitting layer, an organic layer adjacent to the light emitting layer between the light emitting layer and the cathode (an layer adjacent to the light emitting layer on the cathode side), and an electron injecting layer adjacent to the cathode on the light emitting layer side, more preferably contained in any one of the light emitting layer and a layer adjacent to the light emitting layer on the cathode side, and still more preferably contained in the light emitting layer. Alternatively, the compound represented by any one of the general formula (1-1) to the general formula (1-3) may be contained in both layers of the light emitting layer and a layer adjacent to the light emitting layer on the cathode side.

<<Case where the Compound Represented by any One of the General Formula (1-1) to the General Formula (1-3) is Contained in the Light Emitting Layer as a Host Material of the Light Emitting Layer>>

In the case where the compound represented by any one of the general formula (1-1) to the general formula (1-3) is contained in the light emitting layer as a host material of the light emitting layer, the compound represented by any one of the general formula (1-1) to the general formula (1-3) is preferably contained in an amount of 0.1 to 99% by mass, more preferably 1 to 97% by mass, and still more preferably 10 to 96% by mass, relative to the total mass of the light emitting layer.

In the case where the compound represented by any one of the general formula (1-1) to the general formula (1-3) is used as a host material of the light emitting layer, the maximum emission wavelength (hereinafter, sometimes referred to as emission peak wavelength) of the light emitting material is preferably 400 to 700 nm, more preferably 470 to 600 nm, still more preferably 490 to 550 nm, and most preferably 510 to 540 nm.

<<Case where the Compound Represented by any One of the General Formula (1-1) to the General Formula (1-3) is Contained in a Layer Other than the Light Emitting Layer>>

It is also preferred that the organic layers include a light emitting layer containing the phosphorescence emitting material and other organic layers, and the other organic layers disposed between the light emitting layer and the cathode contain a compound having a structure represented by any one of the general formula (1-1) to the general formula (1-3). Among such cases, it is more preferred that the organic layers include an electron transporting layer or a hole blocking layer (more preferably a hole blocking layer), and the electron transporting layer or the hole blocking layer contains the compound represented by any one of the general formula (1-1) to the general formula (1-3). In the case where the compound represented by any one of the general formula (1-1) to the general formula (1-3) is contained in a layer other than the light emitting layer, the compound is preferably contained in an amount of 70 to 100% by mass, and more preferably 85 to 100% by mass, relative to the total mass of the layers other than the light emitting layer.

A number of layers may be provided for each of these organic layers. When providing plural layers, the layers may be formed from the same material or from different materials for respective layers.

(Method for Forming Organic Layer)

The organic layers in the organic electroluminescent element according to the present invention can be suitably formed by any of dry film forming methods such as a deposition method and a sputtering method, and wet type film forming methods (solution coating methods) such as a transfer method, a printing method, a spin coating method, and a bar coating method.

In the organic electroluminescent element according to the present invention, the organic layers disposed between the pair of electrodes preferably contain at least one layer formed by vapor deposition of a composition containing the compound represented by any one of the general formula (1-1) to the general formula (1-3).

(Light Emitting Layer)

The light emitting layer is a layer having a function of, upon application of an electric field, receiving holes from the anode, the hole injecting layer or the hole transporting layer, receiving electrons from the cathode, the electron injecting layer or the electron transporting layer, providing a recombination site of the holes and the electrons, and thereby causing light emitting. However, the light emitting layer in the present invention is not necessarily limited to the light emitting by such a mechanism. The light emitting layer in the organic electroluminescent element according to the present invention preferably contains at least one phosphorescence emitting material.

The light emitting layer in the organic electroluminescent element according to the present invention may be configured only of the light emitting material, or may have a configuration of the layer in which a host material and the light emitting material are mixed. A single, or two or more light emitting materials may be used. The host material is preferably a charge transporting material. A single material or two or more materials may be used as the host material. Examples thereof include a configuration in which an electron transporting host material and a hole transporting host material are mixed. Furthermore, the light emitting layer may contain a material which does not have charge transporting property and does not emit light.

In addition, the light emitting layer may be made of a single layer or multiple layers including two or more layers. The layers may include the same light emitting material or host material, or also may include different materials for the respective layers. In the case where plural light emitting layers are present, the light emitting layers may emit light in different luminous colors from one another.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

In the organic electroluminescent element according to the present invention, it is a preferred embodiment that the light emitting layer contains the compound represented by any one of the general formula (1-1) to the general formula (1-3), and it is a more preferred embodiment that the compound represented by any one of the general formula (1-1) to the general formula (1-3) is used as a host material of the light emitting layer. Here, the host material as referred to in the present specification is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably not more than 5%, more preferably not more than 3%, and still more preferably not more than 1%, relative to the total amount of light emission in the whole of the element.

The light emitting material, and host materials other than the compound represented by any one of the general formula (1-1) to the general formula (1-3), as the materials for the light emitting layer, are described in turn below. Incidentally, the compound represented by any one of the general formula (1-1) to the general formula (1-3) may be used as a material other than one for the light emitting layer, in the organic electroluminescent element according to the present invention.

(Light Emitting Material)

As the light emitting material in the present invention, any of a phosphorescence emitting material, a fluorescence emitting material, and the like may be used.

The light emitting layer in the present invention may contain two or more light emitting materials in order to enhance color purity or to expand the emission wavelength range. At least one of the light emitting materials is preferably a phosphorescence emitting material.

In the present invention, in addition to the at least one phosphorescence emitting material contained in the light emitting layer, a fluorescence emitting material, or a phosphorescence emitting material that is different from the phosphorescence emitting material contained in the light emitting layer can be used as the light emitting material.

The fluorescence emitting material or the phosphorescence emitting material is described in detail in, for example, paragraphs [0100] to [0164] of JP-A-2008-270736, and paragraphs [0088] to [0090] of JP-A-2007-266458, and the matters described in these patent publications may be applied to the present invention.

Examples of the phosphorescence emitting material usable in the present invention include, phosphorescence emitting compounds described in patent publications such as, for example, U.S. Pat. No. 6,303,238B1, U.S. Pat. No.

6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, JP-A-2007-96259, WO 07/095,118, WO 10/111,175, WO 10/027,583, WO 10/028,151, etc., and among them, more preferred examples of the light emitting material include phosphorescence emitting metal complex compounds such as iridium (Ir) complex, platinum (Pt) complex, Cu complex, Re complex, W complex, Rh complex, Ru complex, Pd complex, Os complex, Eu complex, Tb complex, Gd complex, Dy complex, Ce complex, etc. Especially preferred light emitting material is iridium (Ir) complex, platinum (Pt) complex, or Re complex, and among them, preferred are iridium (Ir) complex, platinum (Pt) complex or Re complex containing at least one coordination form from among metal-carbon bond, metal-nitrogen bond, metal-oxygen bond and metal-sulfur bond. Furthermore, in terms of luminous efficiency, driving durability, chromaticity, and the like, iridium (Ir) complex and platinum (Pt) complex are especially preferred, and iridium (Ir) complex is most preferred.

As the phosphorescence emitting material contained in the light emitting layer according to the present invention, iridium (Ir) complex represented by the general formula (E-1) described below, or the platinum (Pt) complex described below is preferably used.

General Formula (E-1)

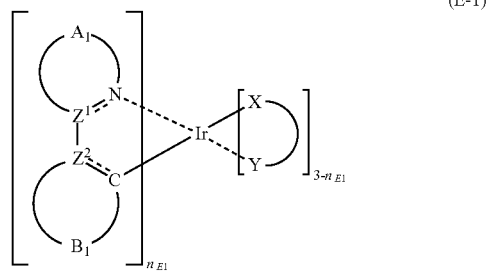

(E-1)

In the general formula (E-1), $Z^1$ and $Z^2$ each independently represent a carbon atom or a nitrogen atom. $A_1$ represents an atomic group that together with $Z^1$ and a nitrogen atom forms a 5- or 6-membered hetero ring. $B_1$ represents an atomic group that together with $Z^2$ and a carbon atom forms a 5- or 6-membered ring. $Z^1$ and $Z^2$ each independently represent a carbon atom or a nitrogen atom. (X—Y) represents a mono-anionic bidentate ligand. $n_{E1}$ represents an integer of 1 to 3.

$Z^1$ and $Z^2$ each are preferably a carbon atom. $n_{E1}$ is preferably 2 or 3, and in this case, two or three ligands each containing $Z^1$, $Z^2$, $A_1$ and $B_1$ exist, but the ligands may be the same as or different from one another.

Examples of the 5- or 6-membered hetero ring containing $A_1$, $Z^1$ and a nitrogen atom include a pyridine ring, a pyrimidine ring, a pyrazine ring, a triazine ring, an imidazole ring, a pyrazole ring, an oxazole ring, a thiazole ring, a triazole ring, an oxadiazole ring, a thiadiazole ring, etc. The 5- or 6-membered hetero ring formed of $A_1$, $Z^1$ and a nitrogen atom may have a substituent.

Examples of the 5- or 6-membered ring formed of $B_1$, $Z^2$ and a carbon atom include a benzene ring, a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, a furan ring, a pyrrole ring, etc. The 5- or 6-membered ring formed of $B_1$, $Z^2$ and a carbon atom may have a substituent.

As the substituent, the Substituent Group A is exemplified. The substituents may be connected together to form a ring. Examples of the thus formed ring include an unsaturated 4- to 7-membered ring, a benzene ring, a pyridine ring, a pyrazine ring, a pyridazine ring, a pyrimidine ring, an imidazole ring, an oxazole ring, a thiazole ring, a pyrazole ring, a thiophene ring, a furan ring, etc. The thus formed ring may have a substituent, and may form a further ring via a substituent on the formed ring. In addition, a substituent on the 5- or 6-membered hetero ring formed of the $A_1$, $Z^1$ and a nitrogen atom and a substituent on the 5- or 6-membered ring formed of the $B_1$, $Z^2$ and a carbon atom may be connected together to form a fused ring similar to one described above. A further ring may be formed via a substituent on the formed ring.

Examples of the ligand represented by (X—Y) include various known ligands used in conventionally known metal complexes such as, for example, ligands described in "Photochemistry and Photophysics of Coordination Compounds" (written by H. Yersin, Springer-Verlag (1987)), nitrogen-containing heteroaryl ligands and diketone ligands, and preferred are the following general formulae (1-1) to (1-39), more preferred are the general formulae (1-1), (1-4), (1-15), (1-16), (1-17), (1-18), (1-19), (1-22), (1-25), (1-28), (1-29), (1-36) and (1-39). The present invention is however not limited thereto

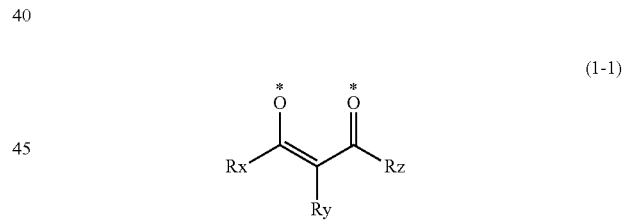

(1-1)

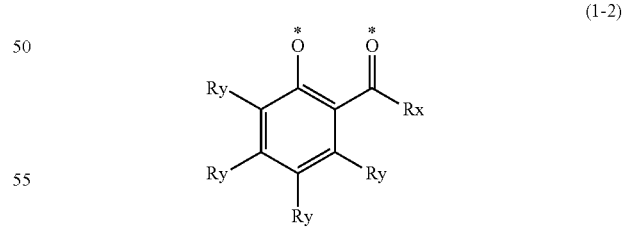

(1-2)

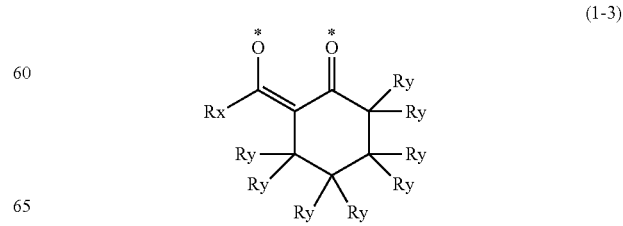

(1-3)

(1-4)
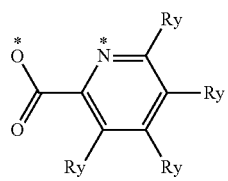
(1-5)
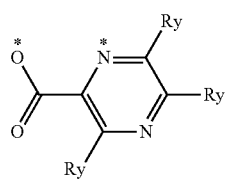
(1-6)
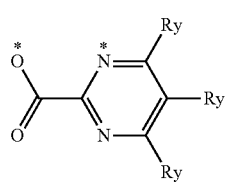
(1-7)
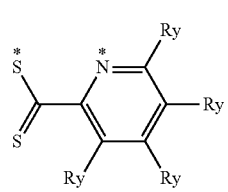
(1-8)
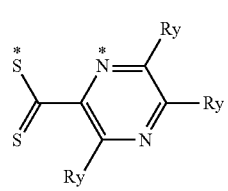
(1-9)
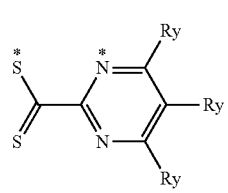
(1-10)
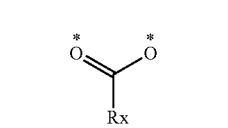
(1-11)
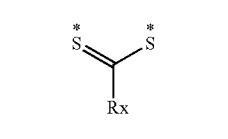
(1-11)
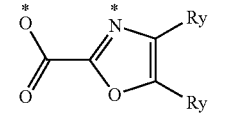
(1-12)
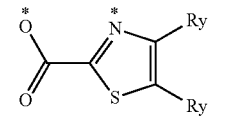
(1-13)
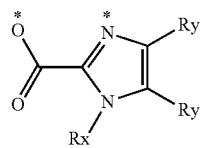
(1-14)
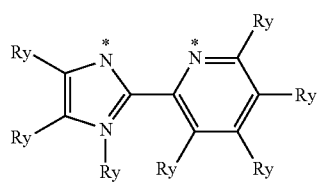
(1-15)
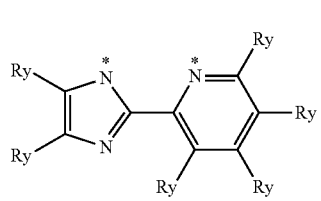
(1-16)
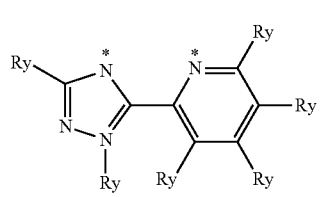
(1-17)
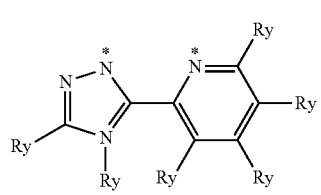
(1-18)
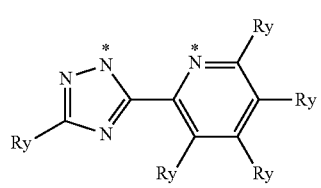
(1-19)
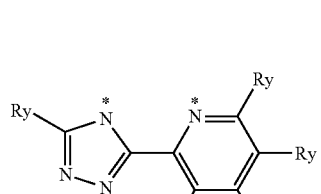
(1-20)
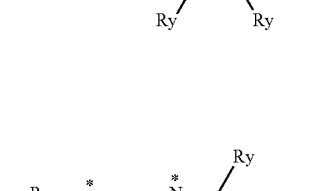
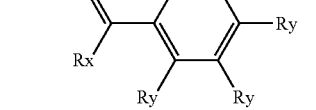

-continued
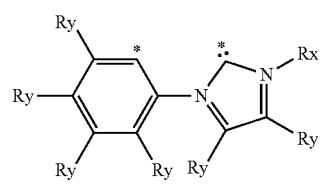
(1-21)
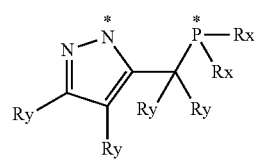
(1-22)
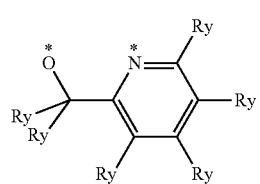
(1-23)
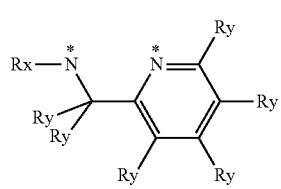
(1-24)
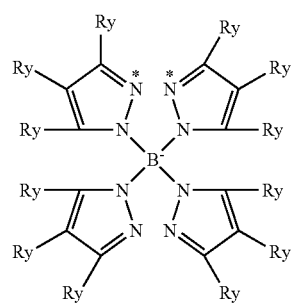
(1-25)
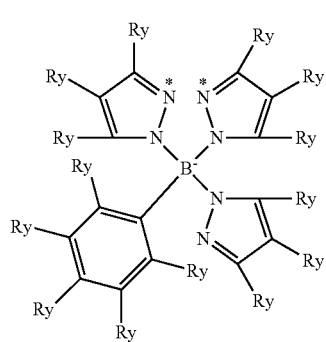
(1-26)
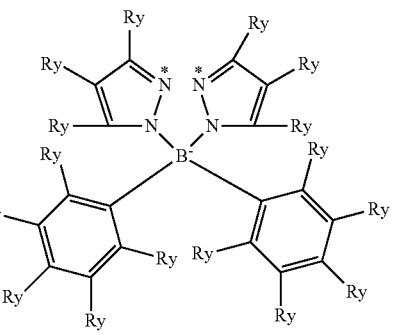
(1-27)
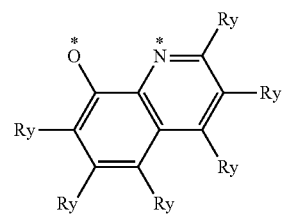
(1-28)
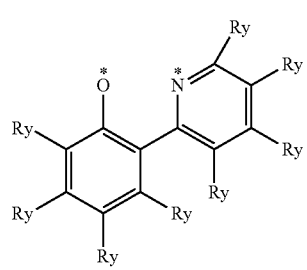
(1-29)
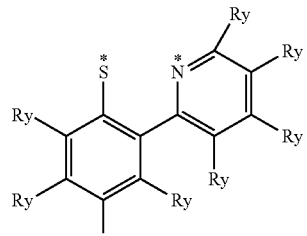
(1-30)
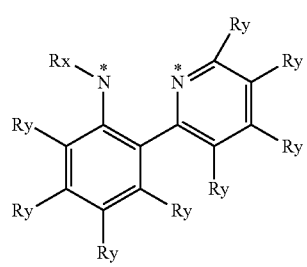
(1-31)
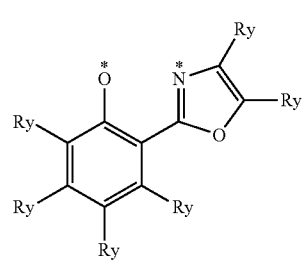
(1-32)

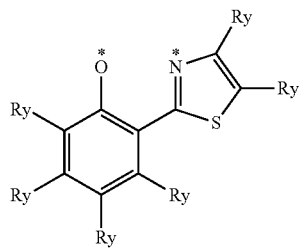
(1-33)

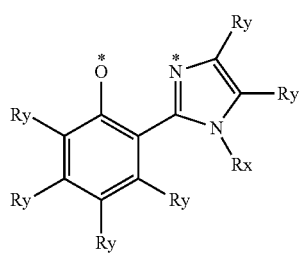
(1-34)

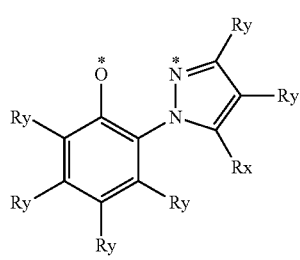
(1-35)

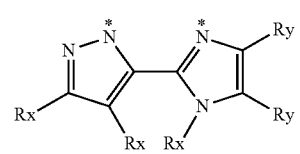
(1-36)

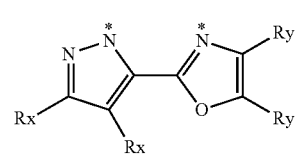
(1-37)

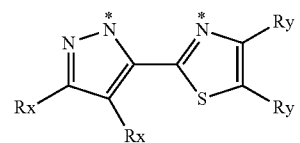
(1-38)

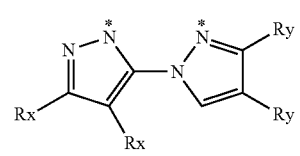
(1-39)

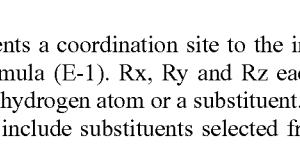

\* represents a coordination site to the iridium (Ir) in the general formula (E-1). Rx, Ry and Rz each independently represent a hydrogen atom or a substituent. Examples of the substituent include substituents selected from the Substituent Group A mentioned above. Rx and Rz preferably each independently represent an alkyl group, a perfluoroalkyl group or an aryl group. Ry is preferably any one of a hydrogen atom, an alkyl group, a perfluoroalkyl group, a fluorine atom, a cyano group and an aryl group. The plural Rxs and Rys present in one ligand may be the same as or different from one another.

The complex having such a ligand can be synthesized in a similar manner to a known example of the synthesis, by using a corresponding ligand precursor.

A preferred embodiment of the iridium (Ir) complex represented by the general formula (E-1) is the iridium (Ir) complex represented by the following general formula (E-2).

General Formula (E-2)

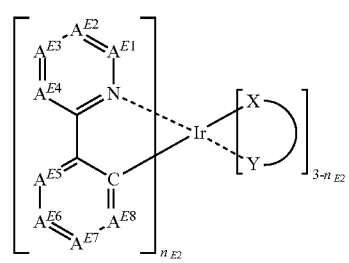

In the general formula (E-2), $A^{E1}$ to $A^{E8}$ each independently represent a nitrogen atom or C—$R^E$. $R^E$ represents a hydrogen atom or a substituent. As the substituent, those exemplified above as the Substituent Group A may be applied. $R^E$s may be connected to each other to form a ring. Examples of the formed ring include those similar to the fused rings described above in the general formula (E-1). (X—Y) and $n_{E2}$ have the same definitions as (X—Y) and $n_{E1}$ in the general formula (E-1), and preferred ranges thereof are also the same as described above. When $n_{E2}$ is 2 or 3, two or three ligands each containing $A^{E1}$ to $A^{E8}$ exist, but the ligands may be the same as or different from one another.

A preferred embodiment of the compound represented by the general formula (E-2) is a compound represented by the following general formula (E-3).

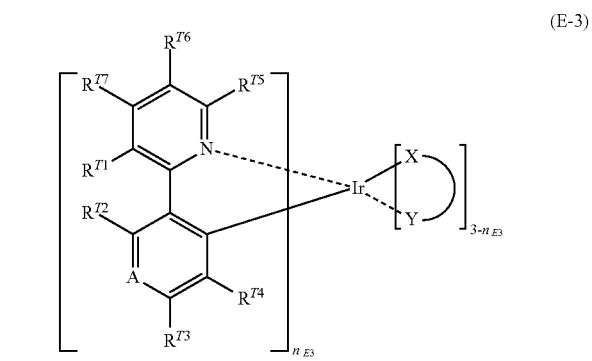

In the general formula (E-3), $R^{T1}$, $R^{T2}$, $R^{T3}$, $R^{T4}$, $R^{T5}$, $R^{T6}$ and $R^{T7}$ have the same definition as the above $R^E$. A represents CR"" or a nitrogen atom and R"" has the same definition as the above $R^E$. Any adjacent two of $R^{T1}$ to $R^{T7}$ and R"" may be bound to each other to form a fused 4- to 7-membered ring. The fused 4- to 7-membered ring is cycloalkene, cycloalkadiene, aryl or heteroaryl, and the fused 4- to 7-membered ring may further have a substituent represented by the Substituent Group A. (X—Y) and $n_{E3}$ have the same definitions as (X—Y) and $n_{E1}$ in the general formula (E-1), and the preferred ranges thereof are also the same as described above. When $n_{E3}$ is 2 or 3, two or three ligands each containing $R^{T1}$, $R^{T2}$, $R^{T3}$, $R^{T4}$, $R^{T5}$, $R^{T6}$, $R^{T7}$ and A exist, but the ligands may be the same as or different from one another.

Preferred ranges of A and $R^{T1}$ to $R^{T7}$ vary depending on the luminescent color required according to the use. The preferred range is described for three different regions of the intended luminescent color: blue to light blue, green to yellow, and yellowish orange to red, but not limited to these descriptions.

In order to obtain a yellowish orange to red luminescent color, the compound represented by the general formula (E-1) is preferably a compound represented by the following general formula (E-4), the following general formula (E-5) or the following general formula (E-6) below.

General Formula (E-4)

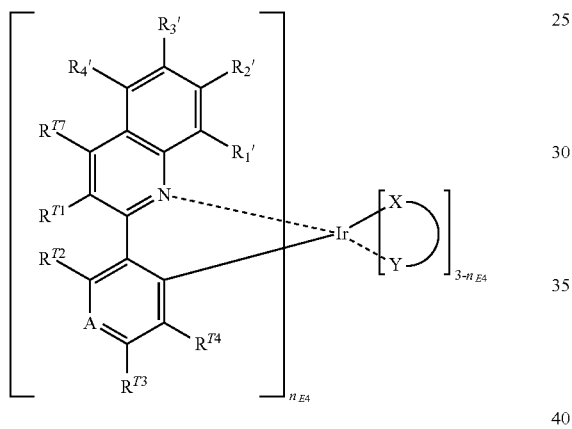

$R^{T1}$ to $R^{T4}$, $R^{T7}$, A (CR'''' or a nitrogen atom), (X—Y) and $n_{E4}$ in the general formula (E-4) have the same definitions as $R^{T1}$ to $R^{T4}$, $R^{T7}$, A, (X—Y) and $n_{E3}$ in the general formula (E-3). $R_1'$ to $R_4'$ have the same definitions as the above-described $R^E$.

Any adjacent two of $R^{T1}$ to $R^{T4}$, $R^{T7}$, $R_1'$ to $R_4'$ and R'''' may be bound to each other to form a fused 4- to 7-membered ring, the fused 4- to 7-membered ring is cycloalkene, cycloalkadiene, aryl or heteroaryl, and the fused 4- to 7-membered ring may further have a substituent represented by the Substituent Group A.

When $n_{E4}$ is 2 or 3, two or three ligands each containing $R^{T1}$ to $R^{T4}$, $R^{T7}$, A and $R_1'$ to $R_4'$ exist, but the ligands may be the same as or different from one another.

$R_1'$ to $R_4'$ are each preferably a hydrogen atom, a fluorine atom, an alkyl group or an aryl group. It is preferred that while A represents CR'''', zero to three of $R^{T1}$ to $R^{T4}$, $R^{T7}$ and R'''' each represent an alkyl group or a phenyl group, and all the remaining groups thereof each are a hydrogen atom.

Specific examples of the compound represented by the general formula (E-4) are listed below, but the compound is not limited thereto.

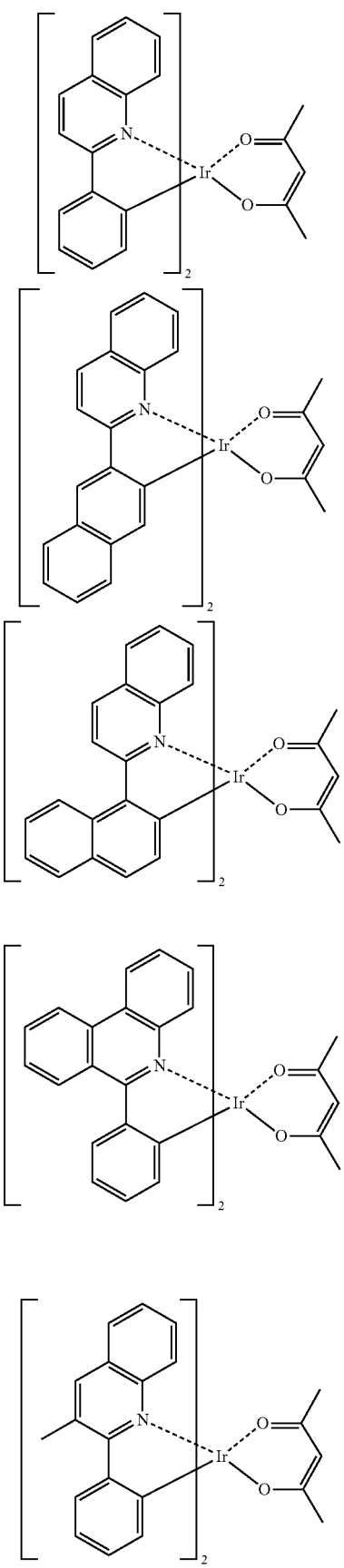

-continued
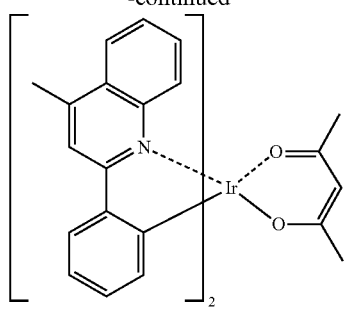
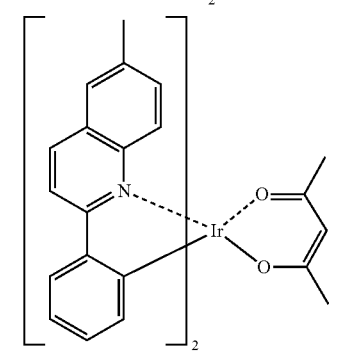
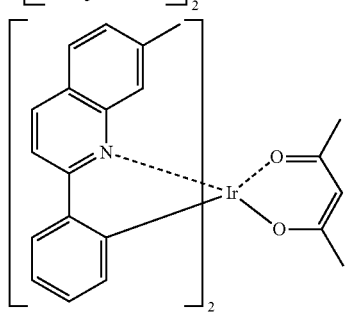
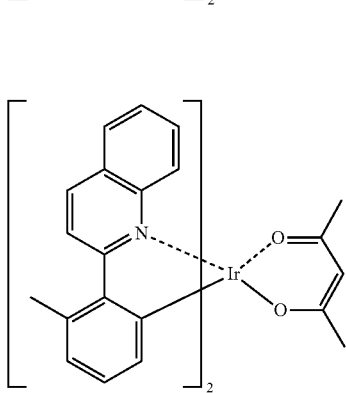
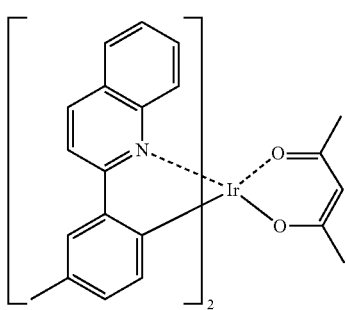
-continued
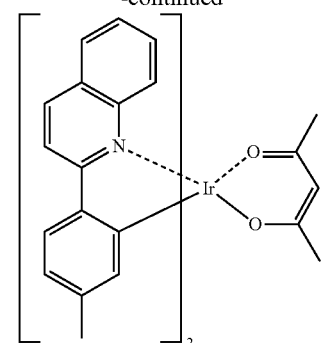
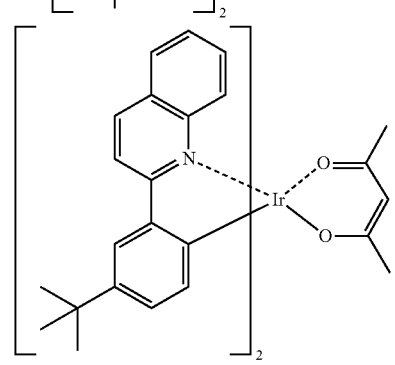
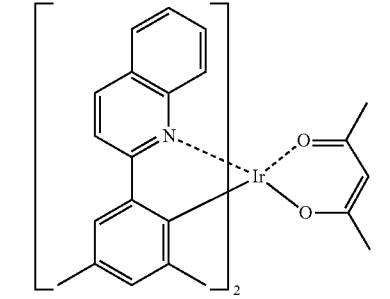
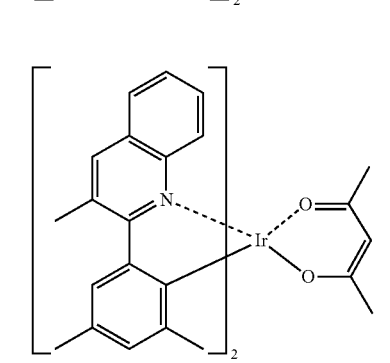
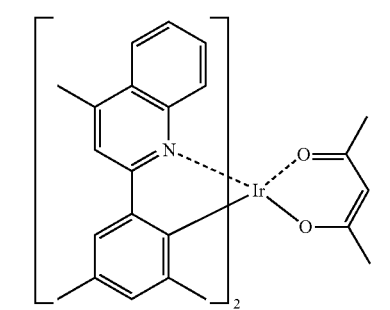

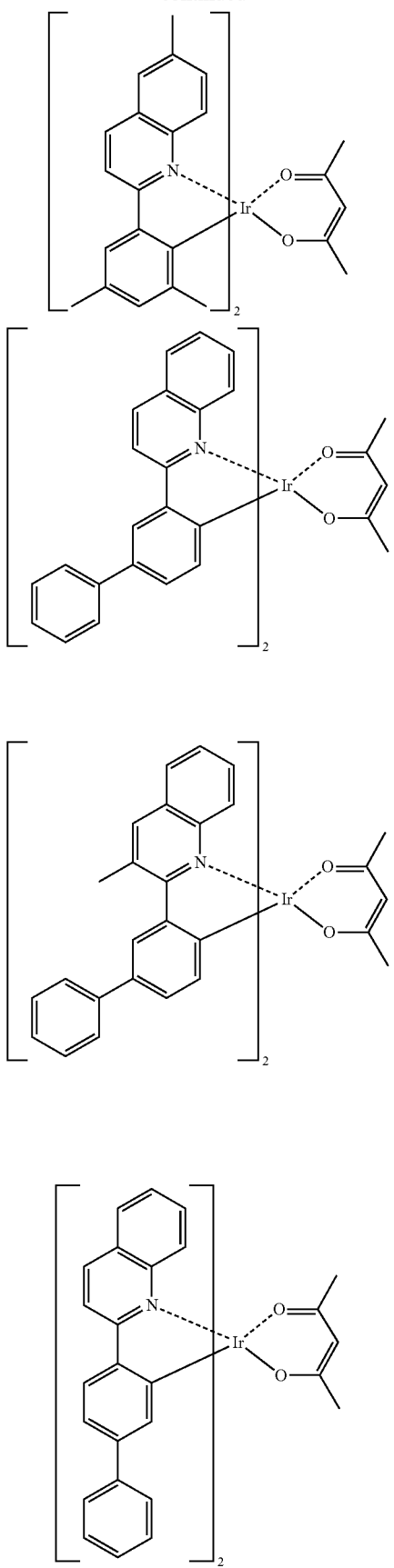
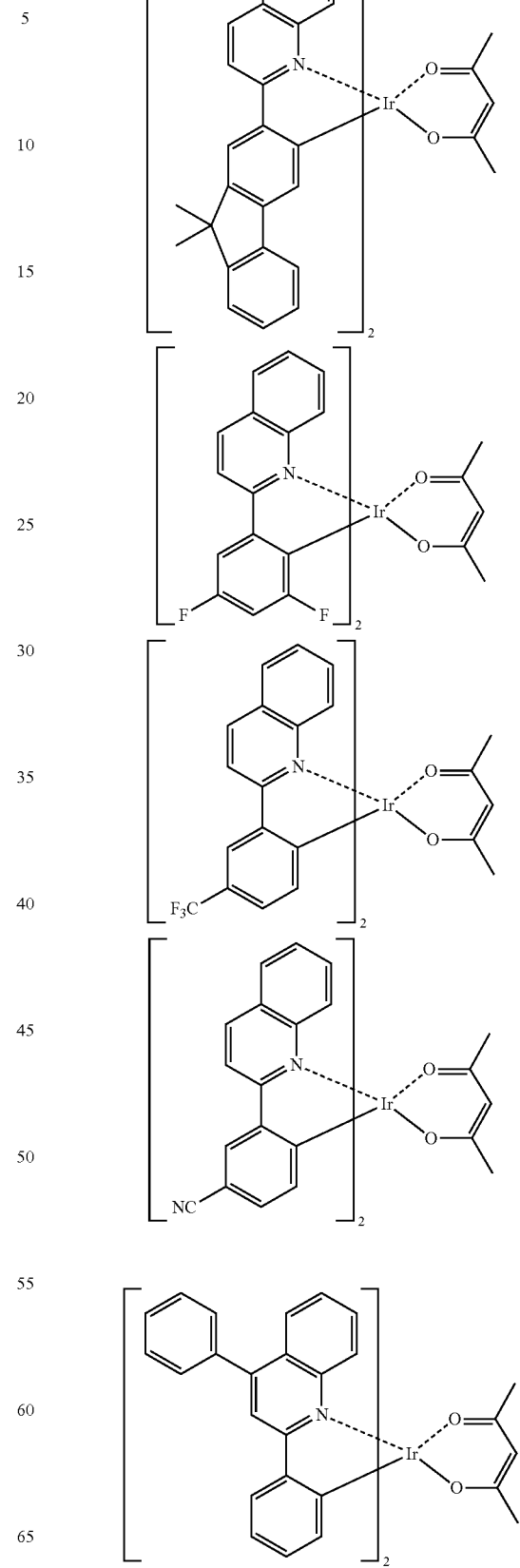

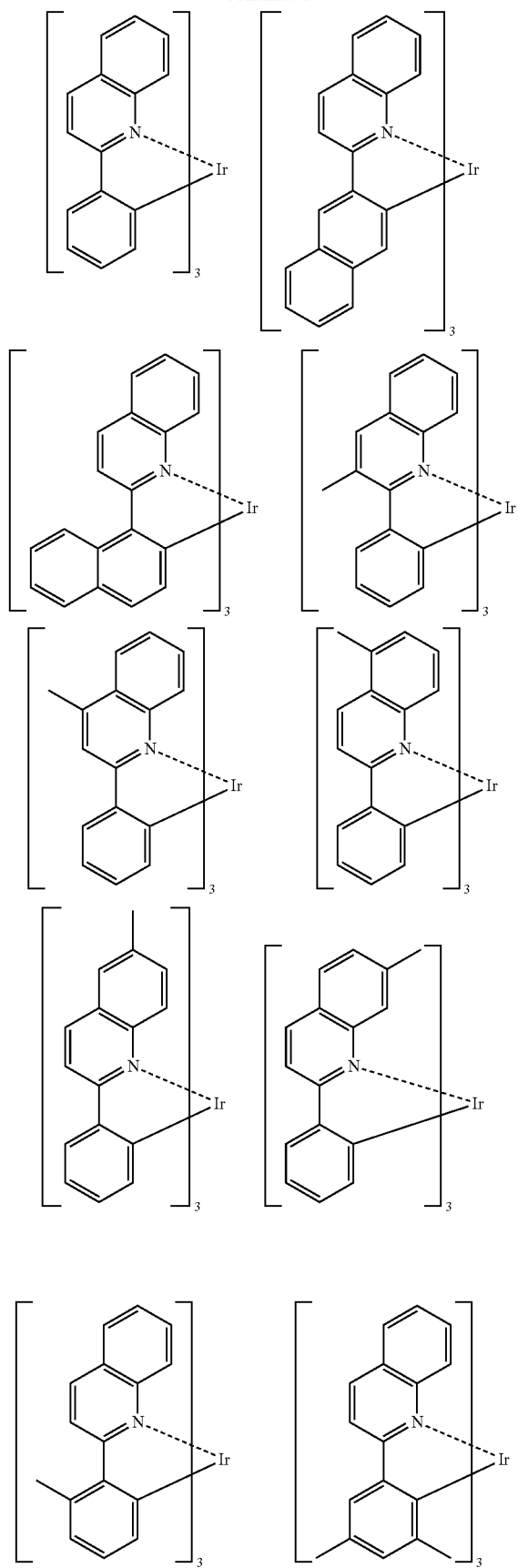

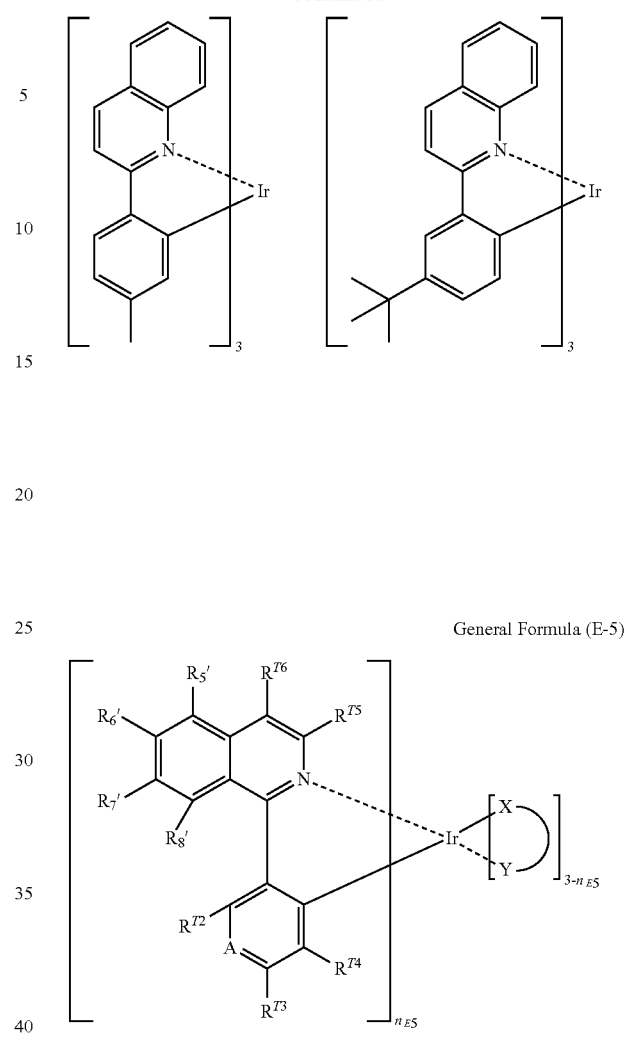

General Formula (E-5)

$R^{T2}$ to $R^{T6}$, A (CR'''' or a nitrogen atom), (X—Y) and $n_{E5}$ in the general formula (E-5) have the same definitions as $R^{T2}$ to $R^{T6}$, A, (X—Y) and $n_{E3}$ in the general formula (E-3). $R_5'$ to $R_8'$ have the same definitions as $R_1'$ to $R_4'$ in the general formula (E-4).

Any adjacent two of $R^{T2}$ to $R^{T6}$, $R_5'$ to $R_8'$, R'''' may be bound to each other to form a fused 4- to 7-membered ring, the fused 4- to 7-membered ring is cycloalkene, cycloalkadiene, aryl or heteroaryl, and the fused 4- to 7-membered ring may further have a substituent represented by the Substituent Group A.

When $n_{E5}$ is 2 or 3, two or three ligands each containing $R^{T2}$ to $R^{T6}$, A and $R_5'$ to $R_8'$ exist, but the ligands may be the same as or different from one another.

In addition, preferred ranges of $R_5'$ to $R_8'$ are the same as the preferred ranges of $R_1'$ to $R_4'$ in the general formula (E-4). It is preferred that while A represents CR'''', zero to three of $R^{T2}$ to $R^{T6}$, R'''', and $R_5'$ to $R_8'$ are each an alkyl group or a phenyl group, and all the remaining groups are each a hydrogen atom.

Specific preferred examples of the compound represented by the general formula (E-5) are listed below, but the compound is not limited thereto.

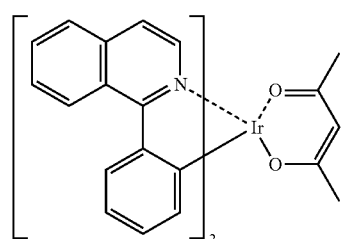
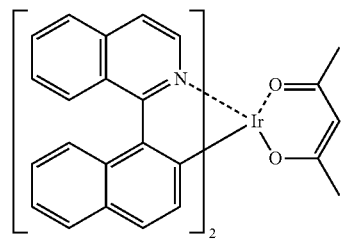
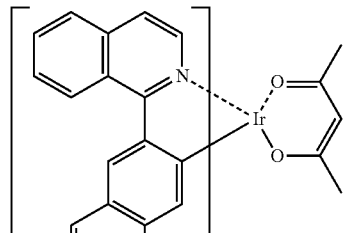
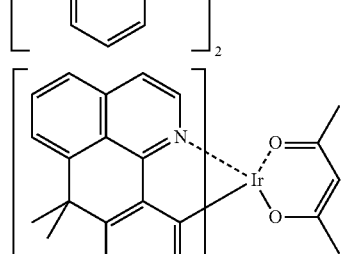
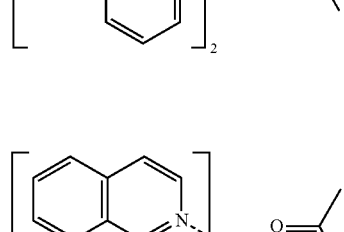
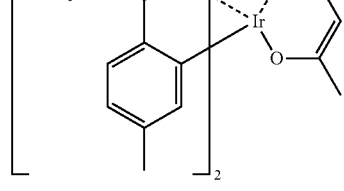
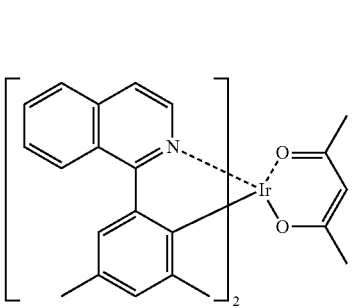
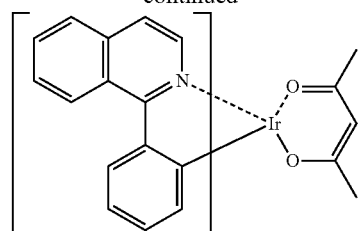
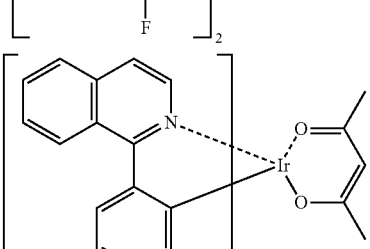
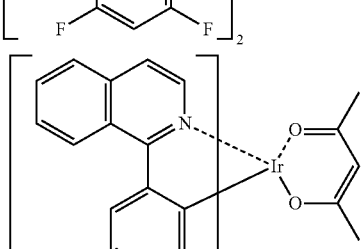
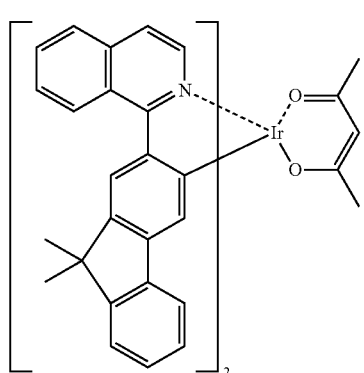

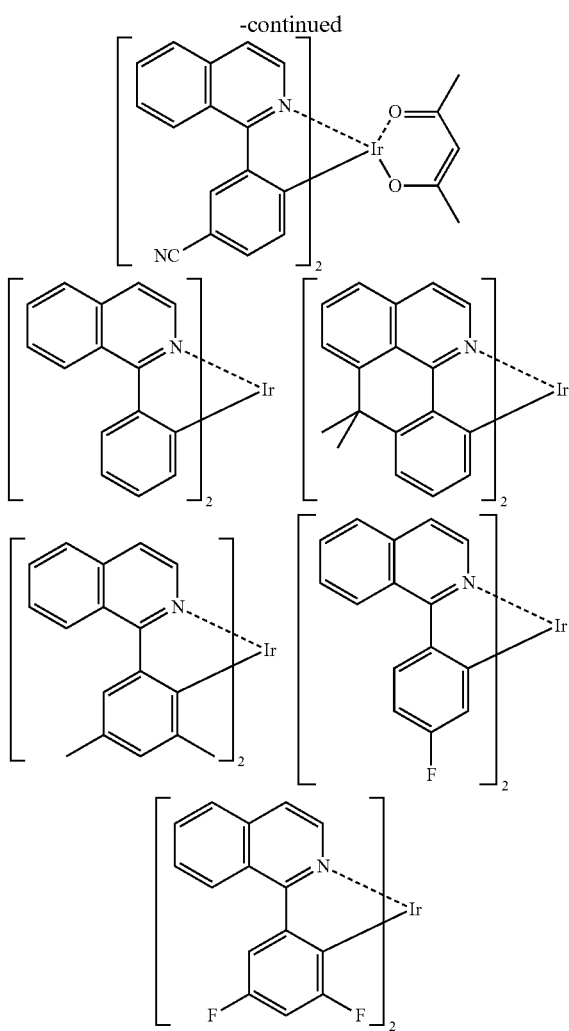

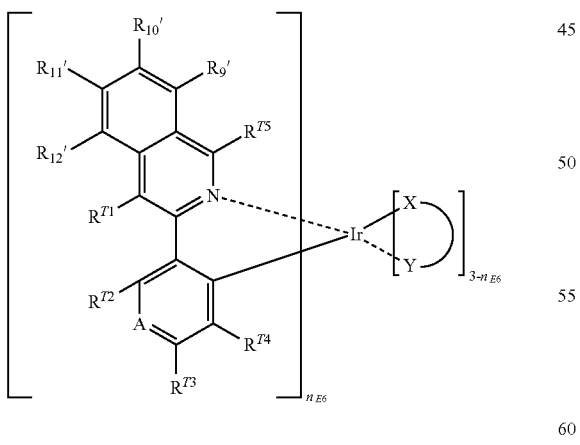

General Formula (E-6)

$R^{T1}$ to $R^{T5}$, A (CR'''' or a nitrogen atom), (X—Y) and $n_{E6}$ in the general formula (E-6) have the same definitions as $R^{T1}$ to $R^{T5}$, A, (X—Y) and $n_{E3}$ in the general formula (E-3). $R_9{}'$ to $R_{12}{}'$ have the same definitions as $R_1{}'$ to $R_4{}'$ in the general formula (E-4).

Any adjacent two of $R^{T1}$ to $R^{T5}$, $R_9{}'$ to $R_{12}{}'$ and R'''' may be bound to each other to form a fused 4- to 7-membered ring, the fused 4- to 7-membered ring is cycloalkene, cycloalkadiene, aryl or heteroaryl, and the fused 4- to 7-membered ring may further have a substituent represented by the Substituent Group A.

When $n_{E6}$ is 2 or 3, two or three ligands each containing $R^{T1}$ to $R^{T5}$, A and $R_9{}'$ to $R_{12}{}'$ exist, but the ligands may be the same as or different from one another.

Preferred ranges of $R_9{}'$ to $R_{12}{}'$ are the same as the preferred ranges of $R_1{}'$ to $R_4{}'$ in the general formula (E-4). It is preferred that while A represents CR'''', zero to three of $R^{T1}$ to $R^{T5}$, R'''', and $R_9{}'$ to $R_{12}{}'$ each represent an alkyl group or a phenyl group, and all the remaining groups thereof are each a hydrogen atom.

Specific preferred examples of the compound represented by the general formula (E-6) are listed below, but the compound is not limited thereto.

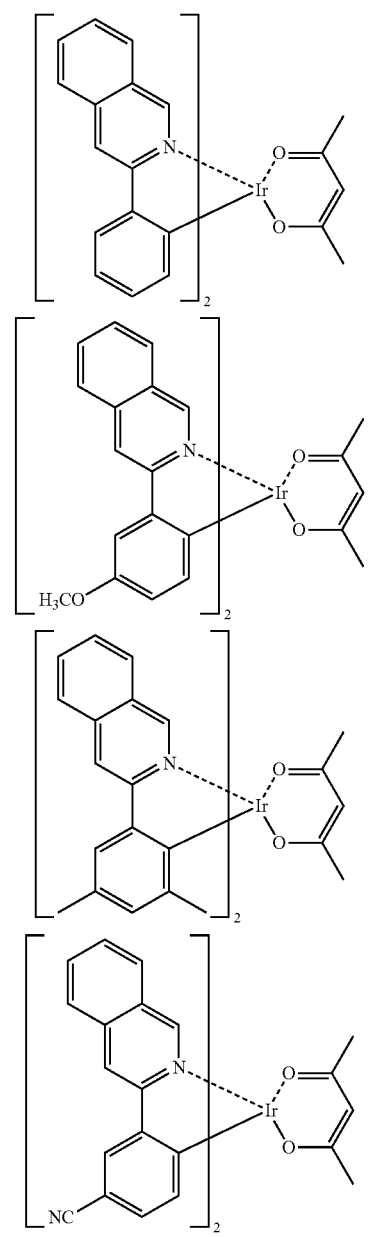

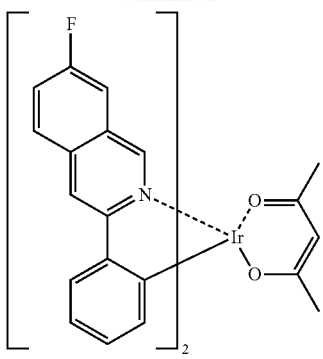
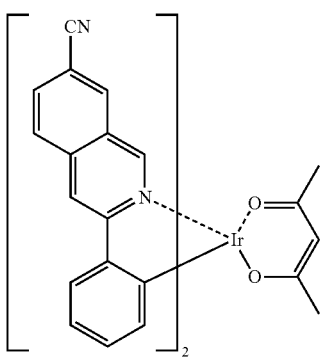
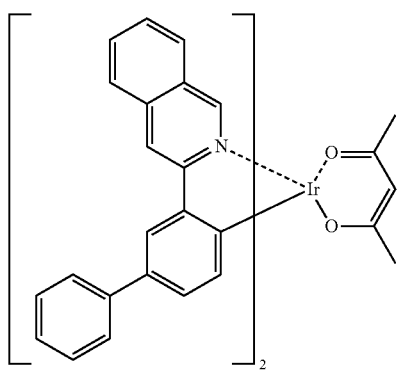
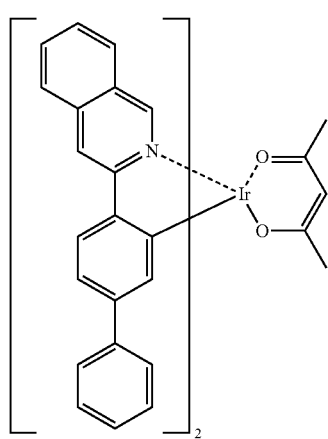
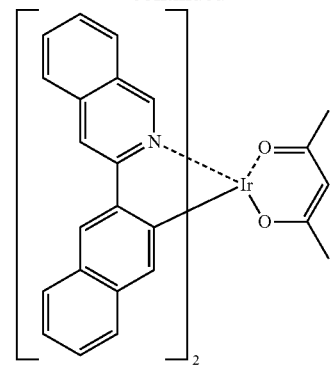
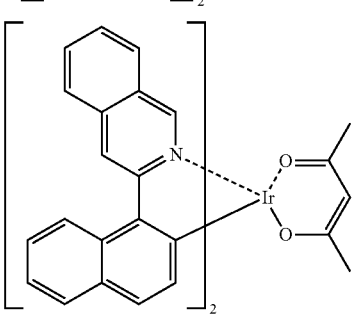
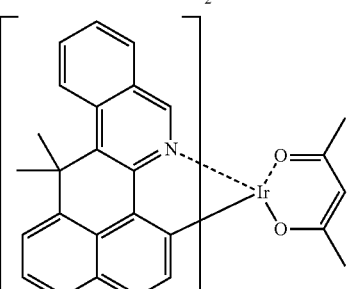
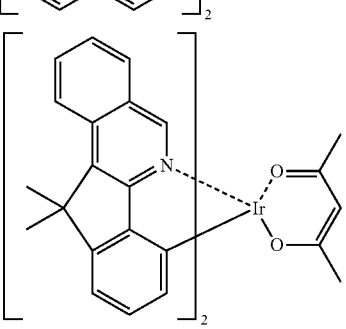
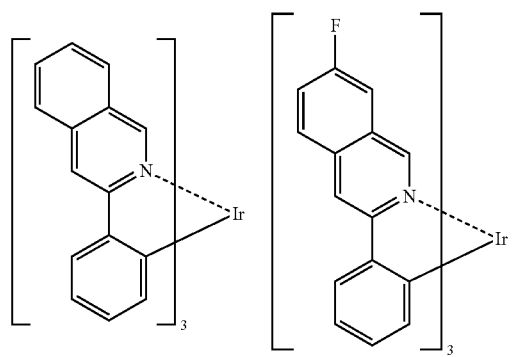

-continued

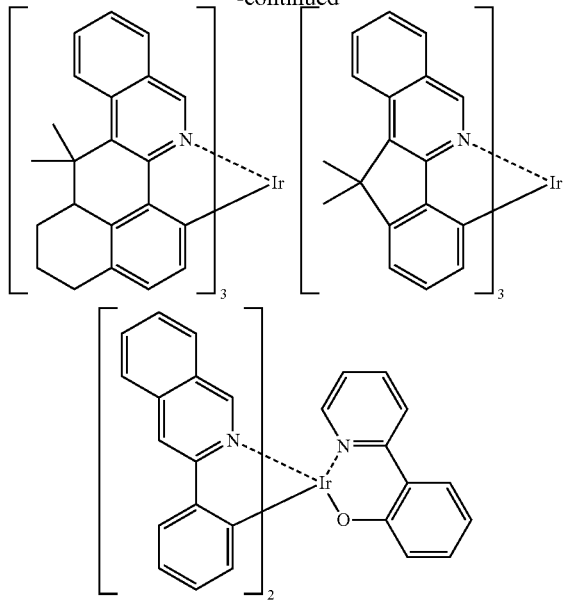

In order to obtain a green to yellow luminescent color, the compound represented by the general formula (E-1) described above is preferably a compound represented by the following general formula (E-7).

General Formula (E-7)

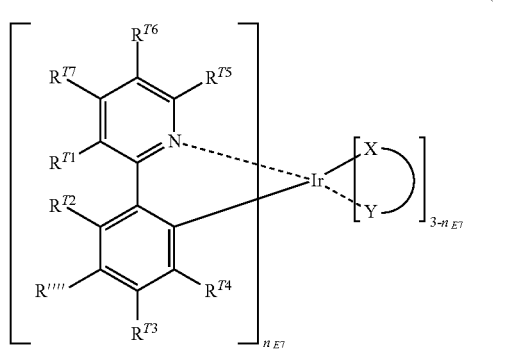

In the general formula (E-7), $R^{T1}$, $R^{T2}$, $R^{T3}$, $R^{T4}$, $R^{T5}$, $R^{T6}$, $R^{T7}$, R'''', (X—Y) and $n_{E3}$ have the same definitions as $R^{T1}$, $R^{T2}$, $R^{T3}$, $R^{T4}$, $R^{T5}$, $R^{T6}$, $R^{T7}$, R'''', (X—Y) and $n_{E3}$ in the general formula (E-3). Any adjacent two of $R^{T1}$ to $R^{T7}$, and R'''' may be bound to each other to form a fused 4- to 7-membered ring, the fused 4- to 7-membered ring is cycloalkene, cycloalkadiene, aryl or heteroaryl, and the fused 4- to 7-membered ring may further have a substituent represented by the Substituent Group A.

When $n_{E7}$ is 2 or 3, two or three ligands containing $R^{T1}$, $R^{T2}$, $R^{T3}$, $R^{T4}$, $R^{T5}$, $R^{T6}$, $R^{T7}$ and R'''' exist, but the ligands may be the same as or different from one another.

$R^{T1}$, $R^{T2}$, $R_{T3}$, $R^{T4}$, $R^{T5}$, $R^{T6}$, $R^{T7}$ and R'''' each are preferably a hydrogen atom, a fluorine atom, an alkyl group, an aryl group, a heteroaryl group or a cyano group.

$n_{E7}$ is preferably 3, and the general formula (E-7) is further preferably a compound represented by the general formula (E-7-1).

General Formula (E-7-1)

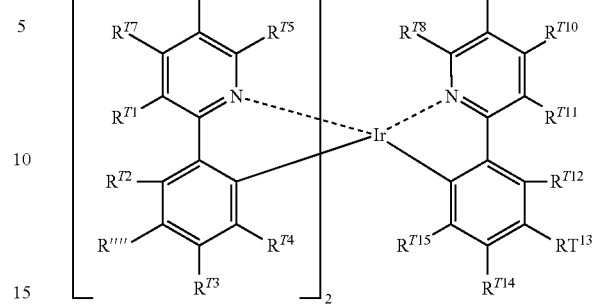

In the general formula (E-7-1), $R^{T1}$, $R^{T2}$, $R^{T3}$, $R^{T4}$, $R^{T5}$, $R^{T6}$, $R^{T7}$ and R'''' have the same definitions as $R^{T1}$, $R^{T2}$, $R^{T3}$, $R^{T4}$, $R^{T5}$, $R^{T6}$, $R^{T7}$ and R'''' in the general formula (E-7), and the preferred ranges thereof are also the same. $R^{T8}$ to $R^{T15}$ have the same definitions as $R^{T1}$, $R^{T2}$, $R^{T3}$, $R^{T4}$, $R^{T5}$, $R^{T6}$, $R^{T7}$, R'''', and the preferred ranges thereof are also the same. However, the phenylpyridine ligand containing $R^{T1}$, $R^{T2}$, $R^{T3}$, $R^{T4}$, $R^{T5}$, $R^{T6}$, $R^{T7}$ and R'''' and the phenylpyridine ligand containing $R^{T8}$ to $R^{T15}$ are different from each other.

In order to obtain a luminescent color closer to green among the green to yellow luminescent colors, it is preferred that $R^{T1}$, $R^{T2}$, $R^{T3}$, $R^{T4}$, $R^{T5}$, $R^{T6}$, $R^{T7}$ and R'''' each are a hydrogen atom, a fluorine atom, an alkyl group or a cyano group, and it is more preferred that one to three of the $R^{T1}$, $R^{T5}$, $R^{T4}$ and R'''' each are an alkyl group. $R^{T8}$ to $R^{T11}$ each are preferably a hydrogen atom or an alkyl group. $R^{T12}$ to $R^{T15}$ each are preferably a hydrogen atom, an alkyl group, a cyano group or an aryl group. The substituted position by the alkyl group, the cyano group or the aryl group is preferably on $R^{T13}$ or $R^{T14}$. The aryl group may further have a substituent, or may form a fused ring via a substituent.

In order to obtain a luminescent color closer to yellow among the green to yellow luminescent colors, it is preferred that $R^{T1}$, $R^{T2}$, $R^{T3}$, $R^{T4}$, $R^{T5}$, $R^{T6}$, $R^{T7}$ and R'''' each are a hydrogen atom and an alkyl group, and it is more preferred that one to three of the $R^{T1}$, $R^{T5}$, $R^{T4}$, R'''' each are an alkyl group. It is preferred that at least one of $R^{T8}$ to $R^{T11}$ is an aryl group, and it is more preferred that either one of $R^{T9}$ and $R^{T10}$ is an aryl group and the remaining one is a hydrogen atom or an alkyl group. The aryl group may further have a substituent or may form a fused ring via a substituent.

The general formula (E-7-1) may also preferably include a partial structure represented by the general formula (E-7-2) in the general formula (E-7-1). When having the general formula (E-7-2), the effects such as decrease of voltage and enhancement of durability are sometimes exhibited significantly.

General Formula (E-7-2)

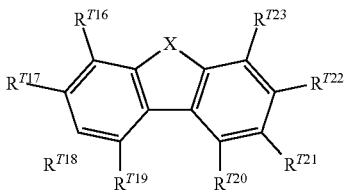

In the general formula (E-7-2), X is —O—, —S—, —NR$^{T24}$—, —CR$^{T25}$R$^{T26}$— or —SiR$^{T27}$R$^{T28}$—, and any one of $R^{T16}$ to $R^{T28}$ is bound to a part of the general formula (E-7-1) via a single bond or via a substituent.

In the general formula (E-7-2), any one of $R^{T16}$ to $R^{T28}$ is preferably bound to a part of the general formula (E-7-1) via a single bond or via an aryl group. In the case where a luminescent color closer to green is desired, the bond to a part of the general formula (E-7-1) is made preferably on $R^{T13}$ or $R^{T14}$ and more preferably on $R^{T13}$. In the case where a luminescent color closer to yellow is desired, the bond is made preferably on $R^{T9}$ or $R^{T10}$.

X is preferably —O—, —S—, —NR$^{T24}$— or —CR$^{T25}$R$^{T26}$—, and more preferably —O— or —S—.

When X is —O— or —S—, X is preferably bound to a part of the general formula (E-7-1) via a single bond at the position of $R^{T16}$, and when X is —NR$^{T24}$—, X is preferably bound to a part of the general formula (E-7-1) via a single bond at the position of $R^{T18}$ or $R^{T24}$, and when X is —CR$^{T25}$R$^{T26}$—, X is preferably bound to a part of the general formula (E-7-1) via a single bond at the position of $R^{T17}$.

Specific preferred examples of the compound represented by the general formula (E-7) are listed below, but the compound is not limited thereto.

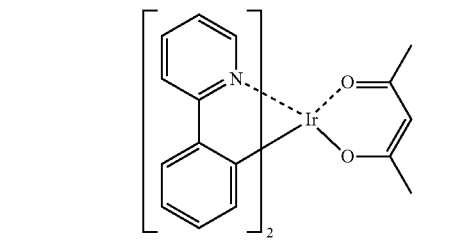

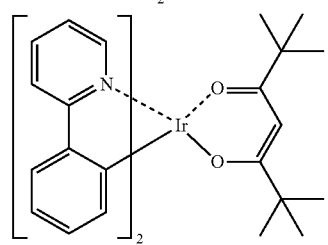

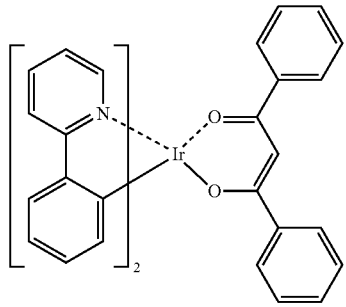

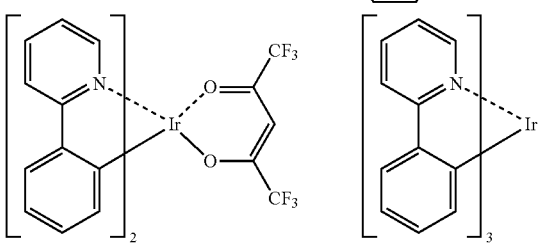

-continued

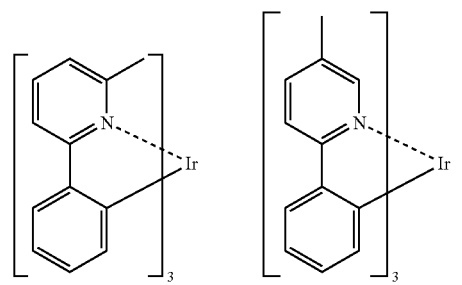

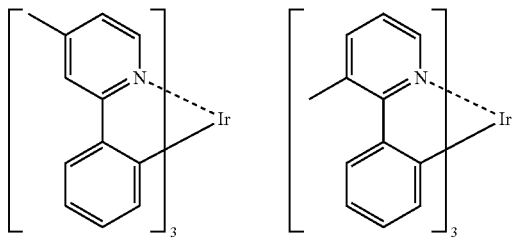

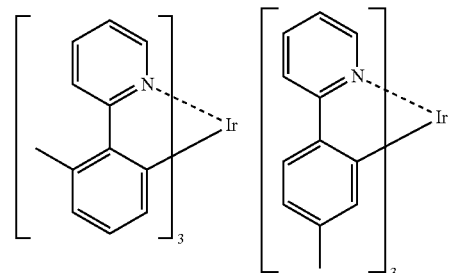

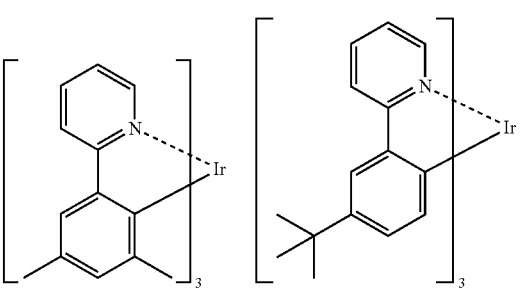

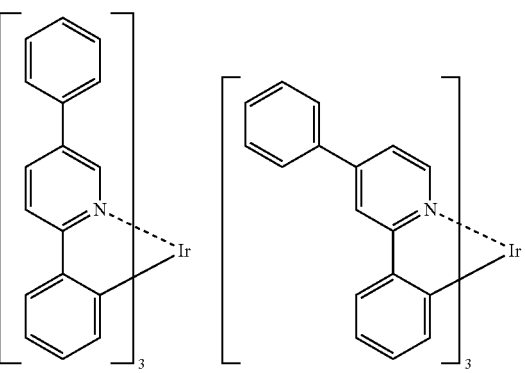

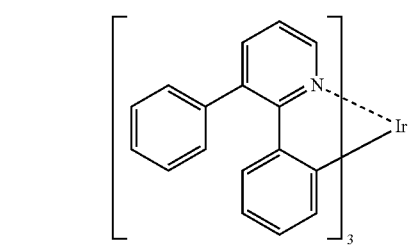

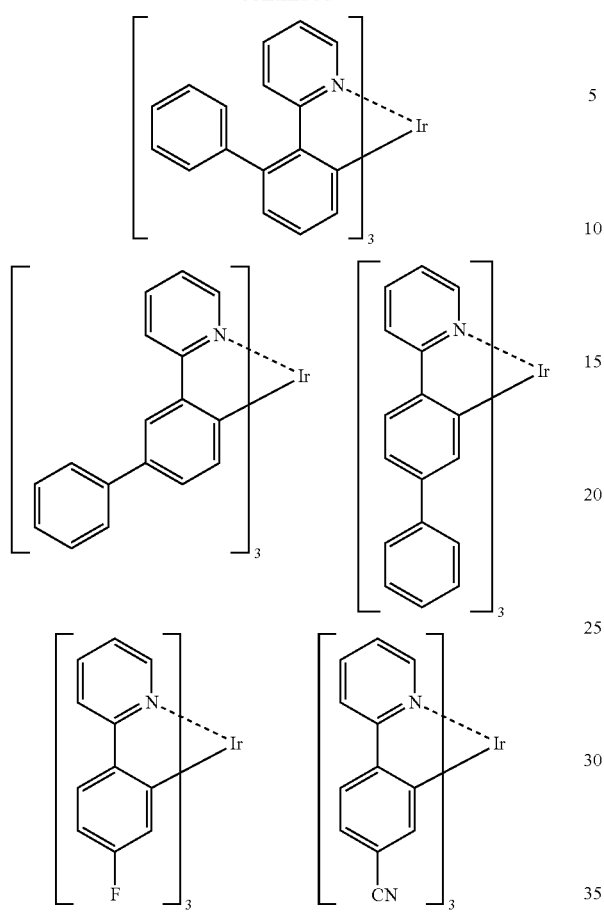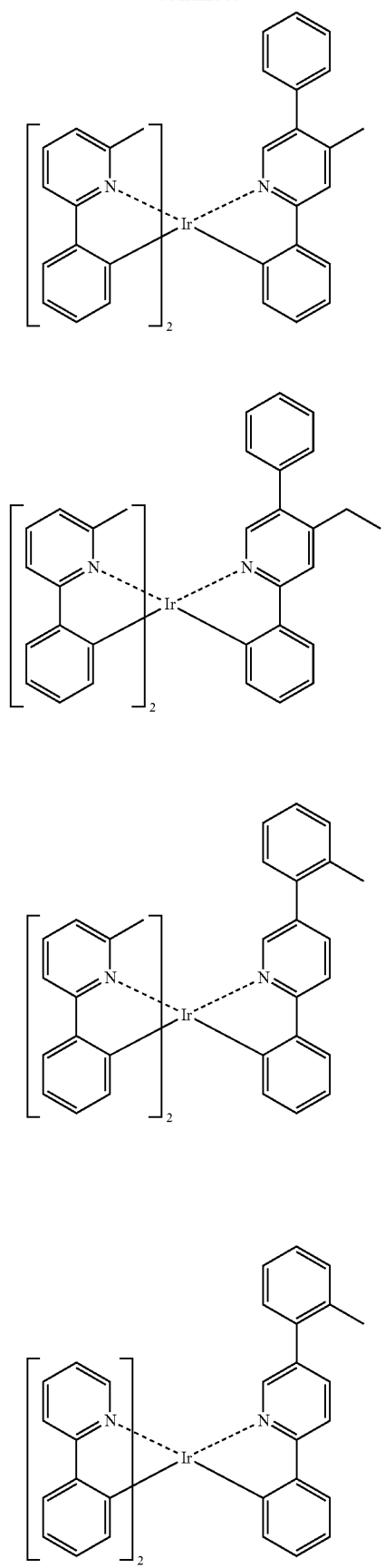

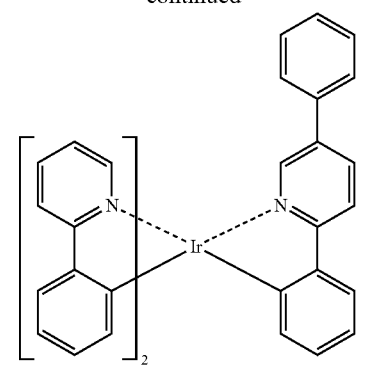
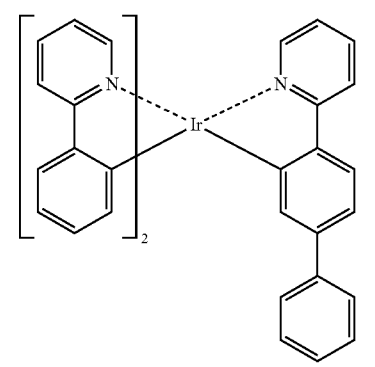
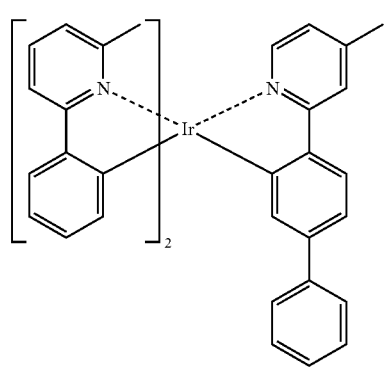
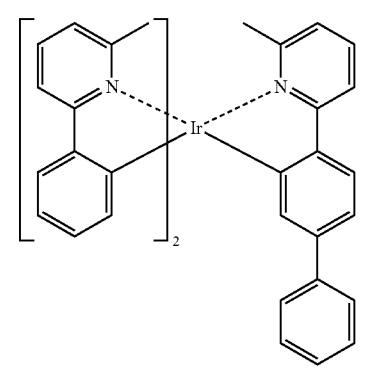
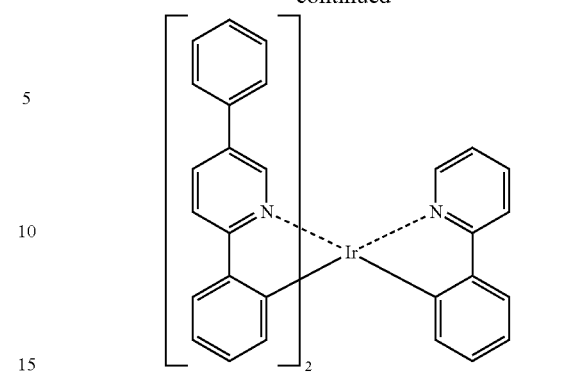
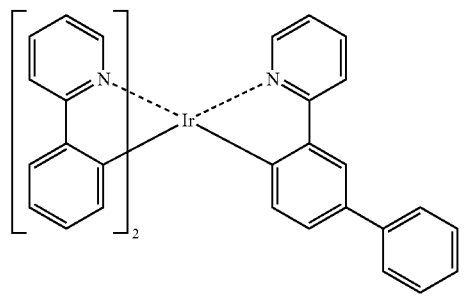
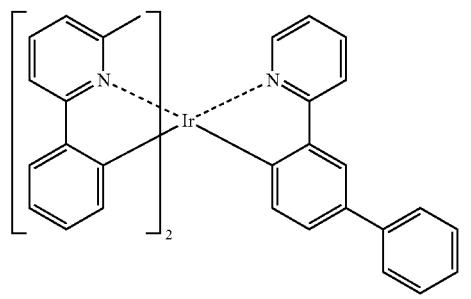
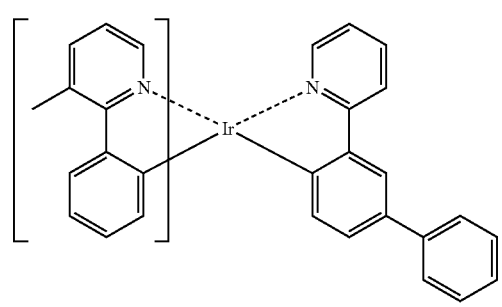
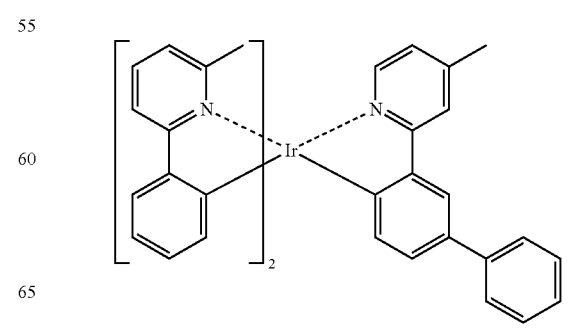

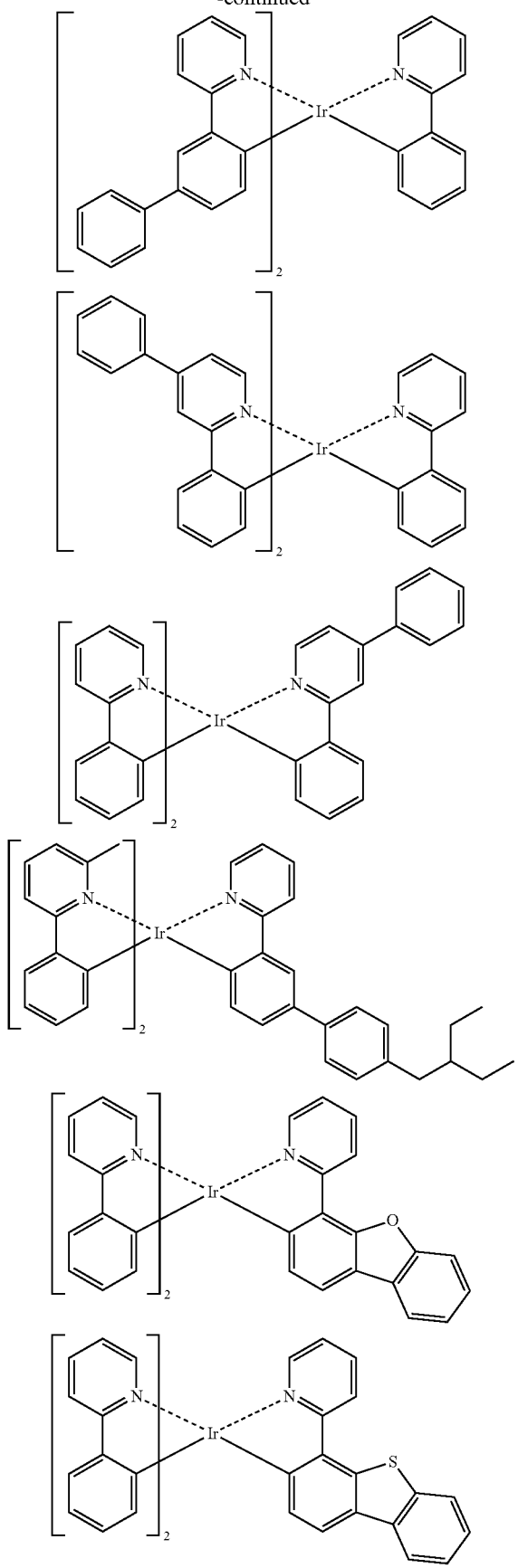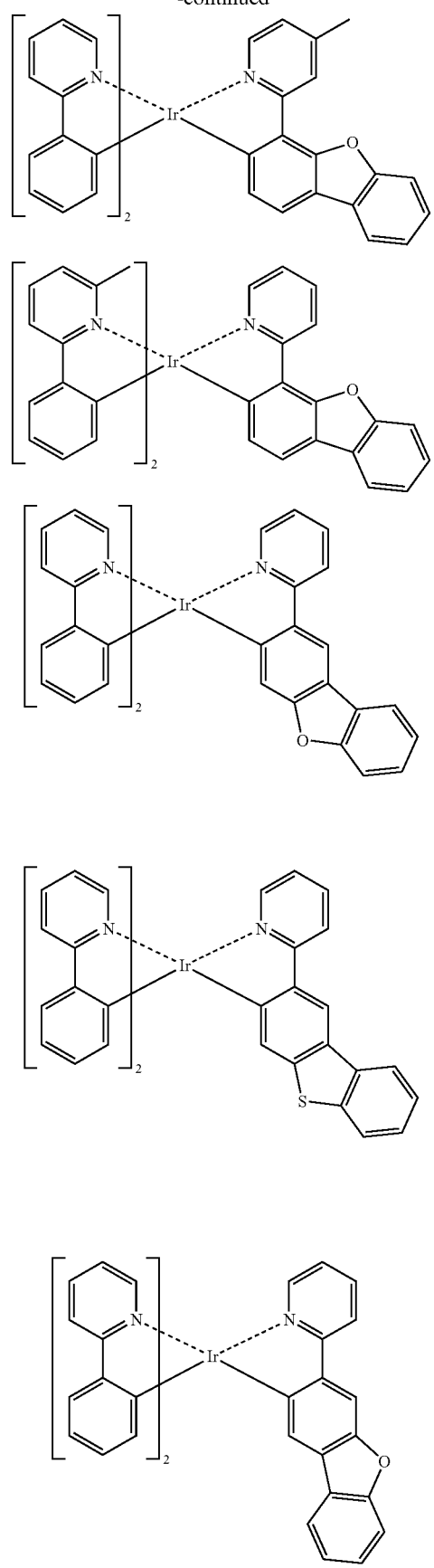

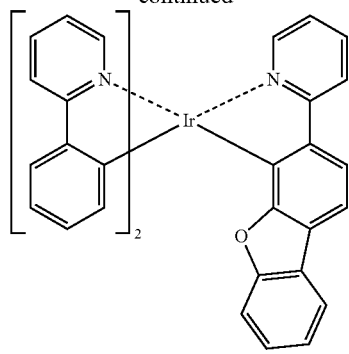
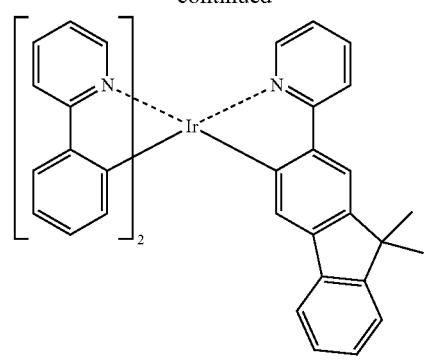
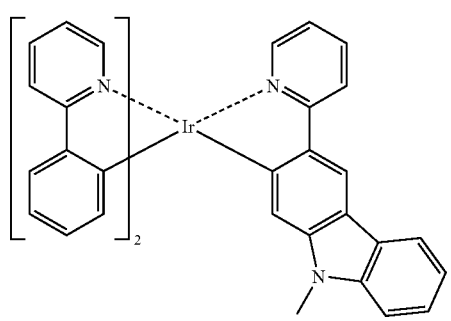
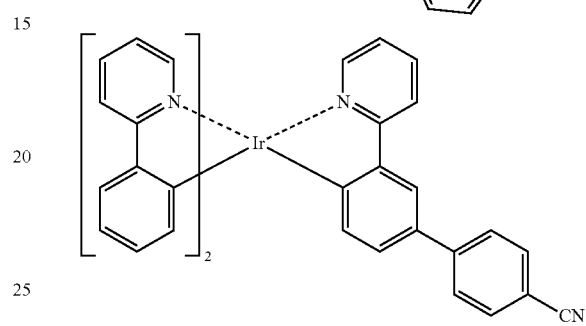
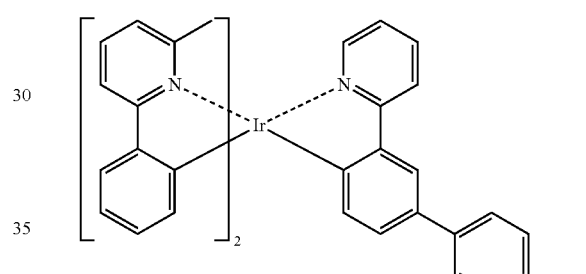
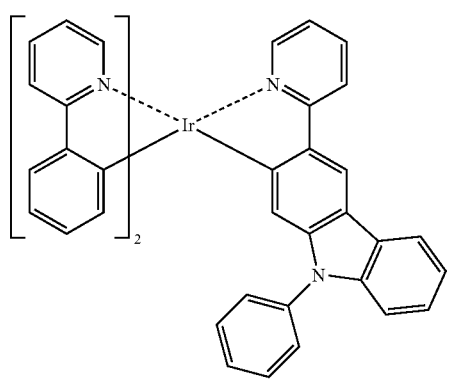
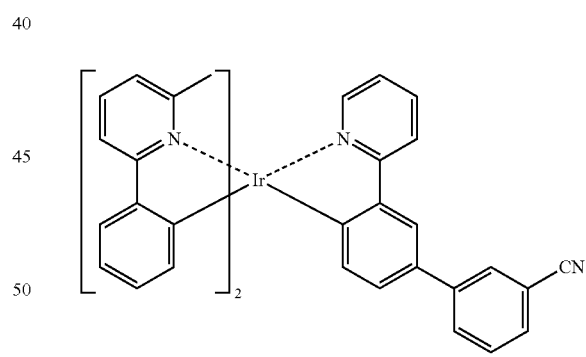
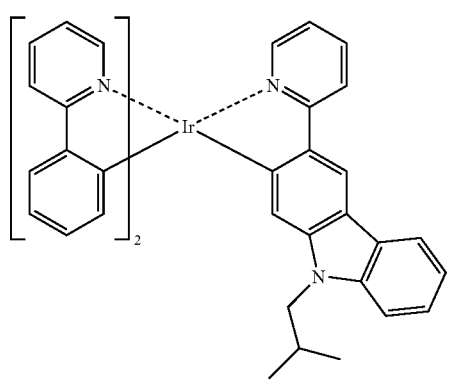
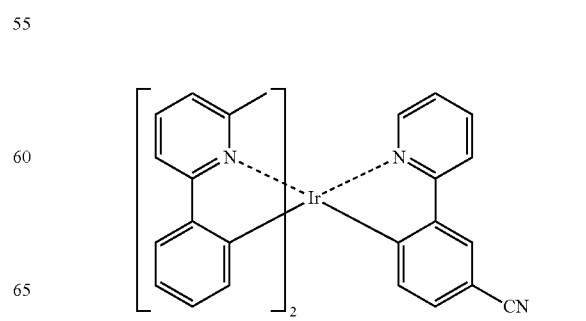

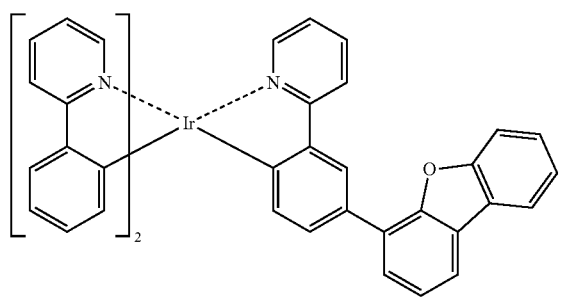
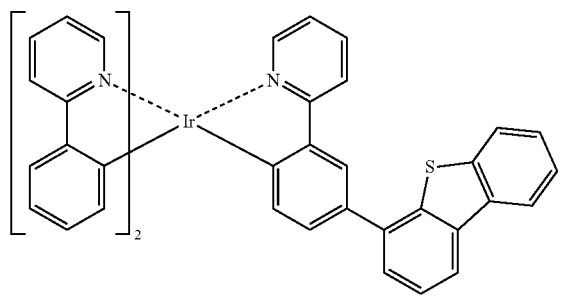
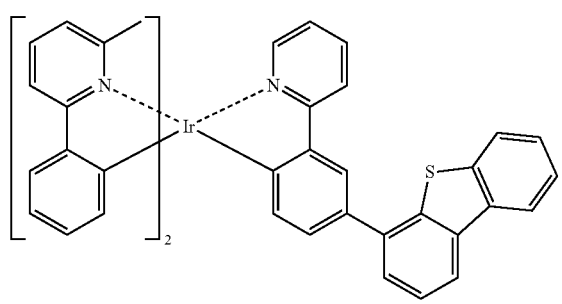
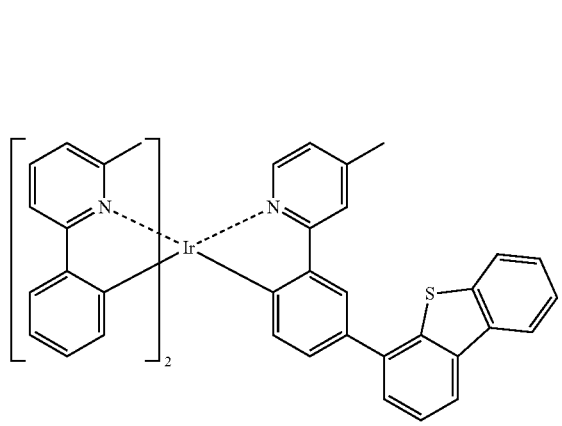
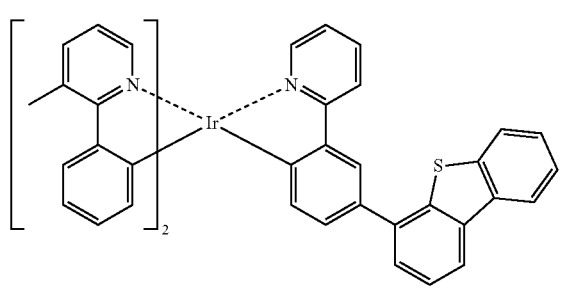
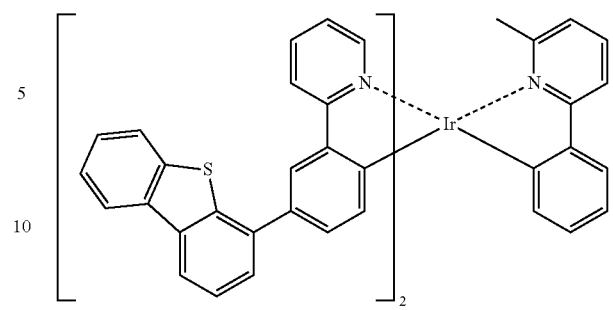
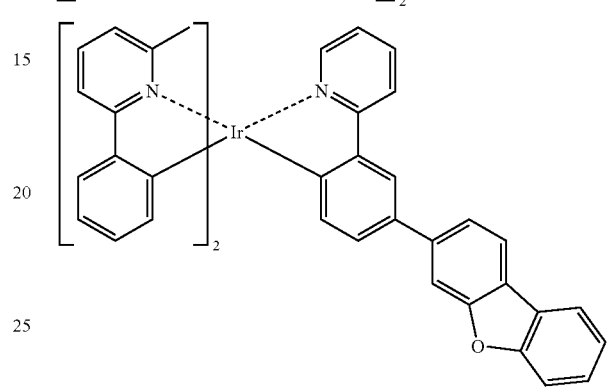
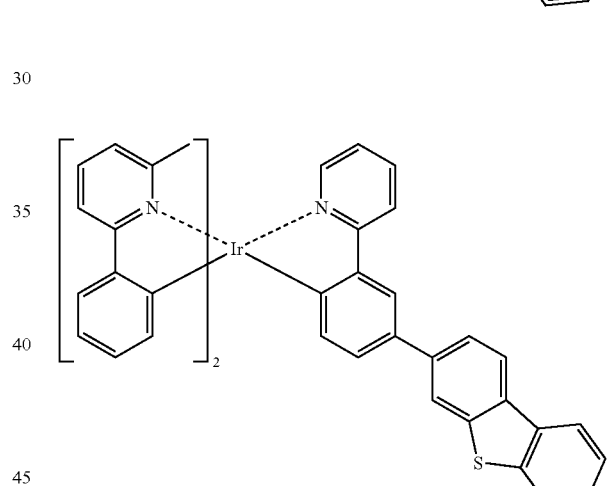
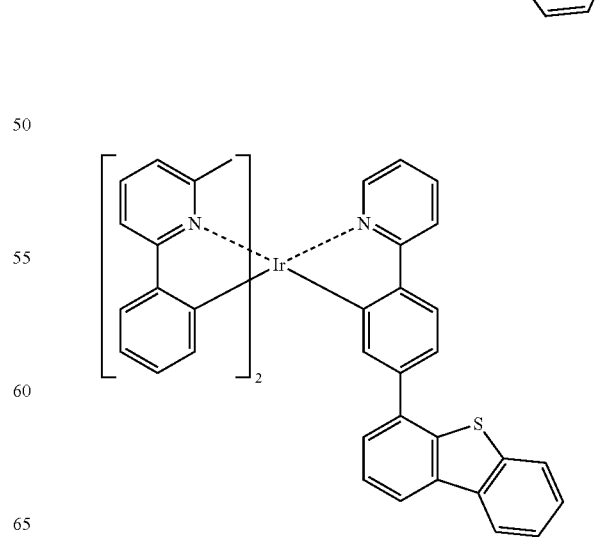

93
-continued
94
-continued
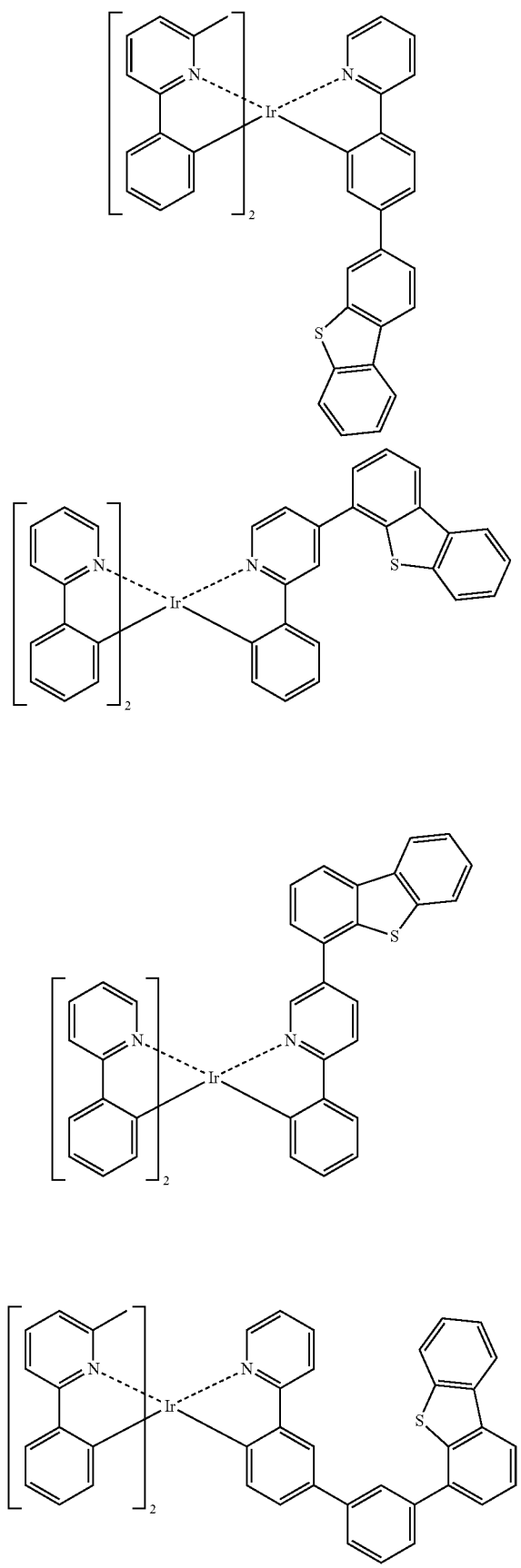
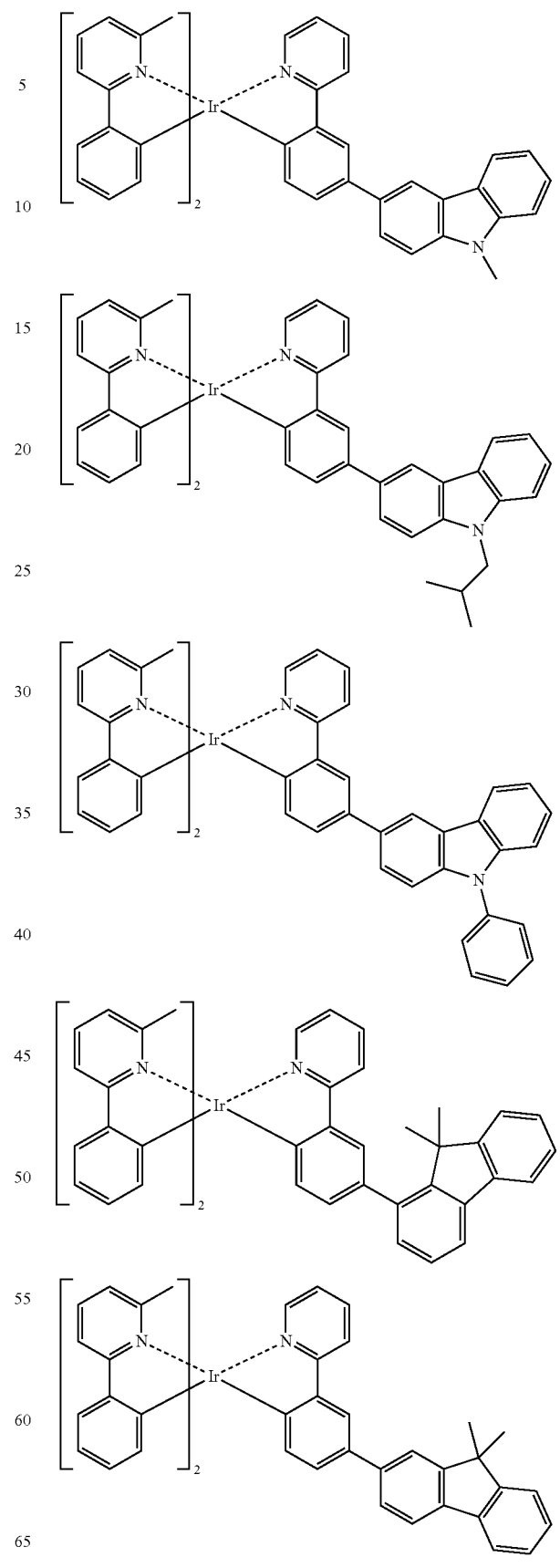

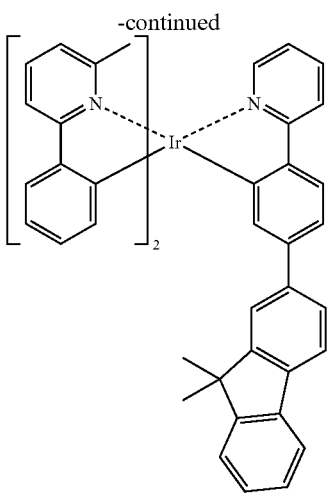

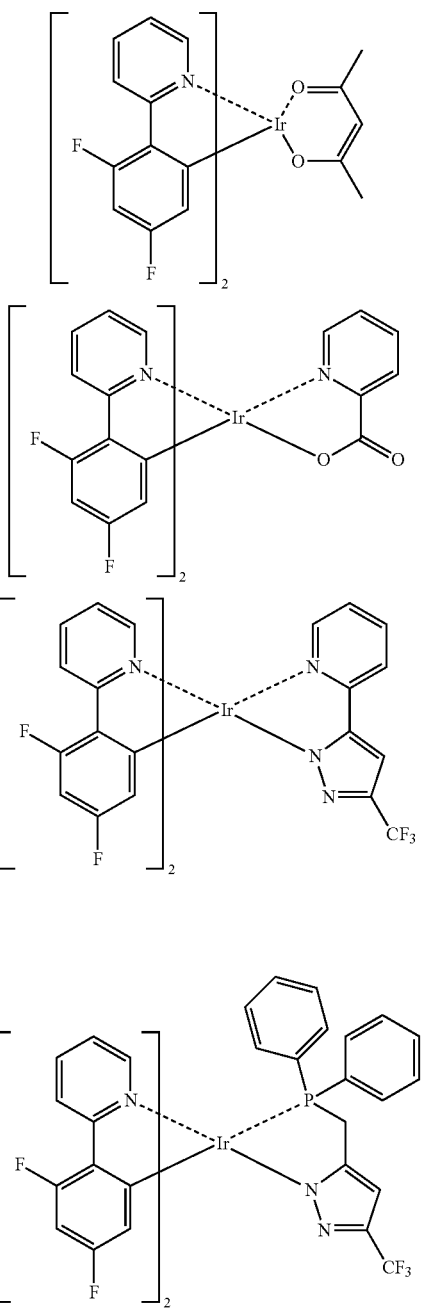

In order to obtain a blue to light blue luminescent color, the compound represented by the general formula (E-1) is preferably a compound represented by the following general formula (E-8) or the following general formula (E-9).

General Formula (E-8)

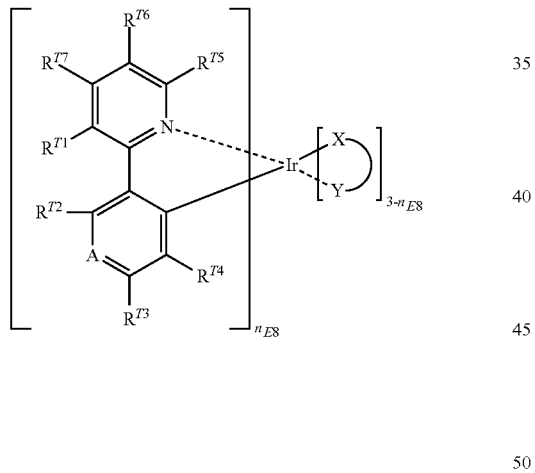

$R^{T1}$, $R^{T2}$, $R^{T3}$, $R^{T4}$, $R^{T5}$, $R^{T6}$, $R^{T7}$, A (CR"" or a nitrogen atom), (X—Y) and $n_{E8}$ in the general formula (E-8) have the same definitions as $R^{T1}$, $R^{T2}$, $R^{T3}$, $R^{T4}$, $R^{T5}$, $R^{T6}$, $R^{T7}$, A, (X—Y), $n_{E3}$ in the general formula (E-3).

$R^{T1}$, $R^{T5}$ to $R^{T7}$ in the general formula (E-8) each are more preferably a hydrogen atom, an alkyl group or an aryl group. $R^{T2}$ to $R^{T4}$ each are preferably a hydrogen atom, a fluorine atom or a cyano group. A is preferably a CR"" wherein R"" is a fluorine atom or a cyano group, or a nitrogen atom. $n_{E8}$ is preferably 2 or 3. (X—Y) has the same definition as (X—Y) in the general formula (E-1), and the preferred range thereof is also the same.

Specific preferred examples of the compound represented by the general formula (E-8) are listed below, but the compound is not limited thereto.

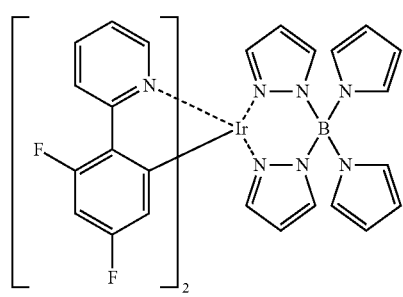

97
-continued
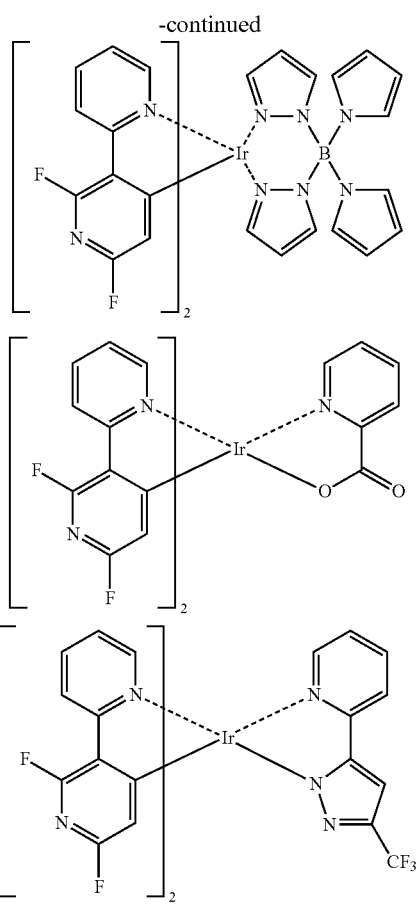
98
-continued
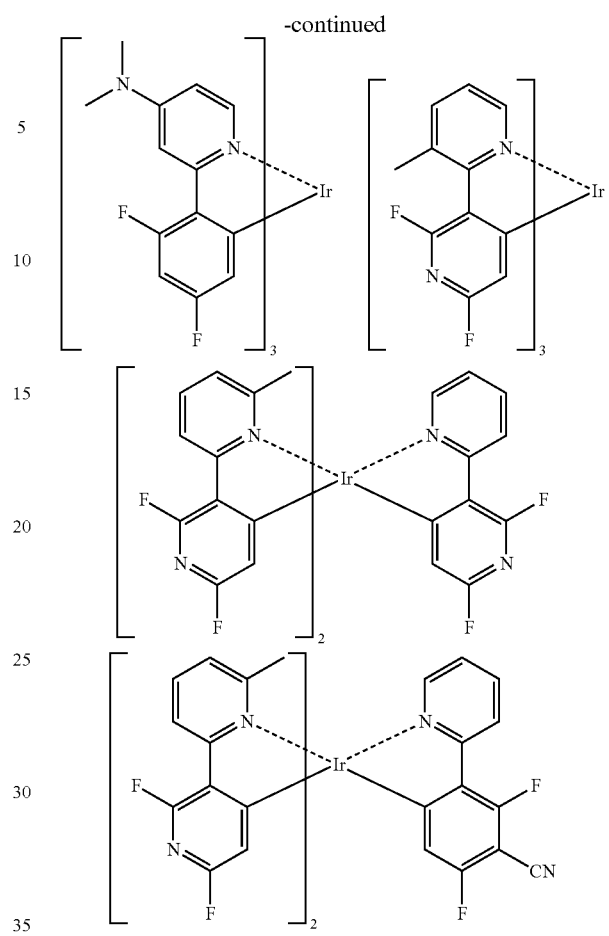
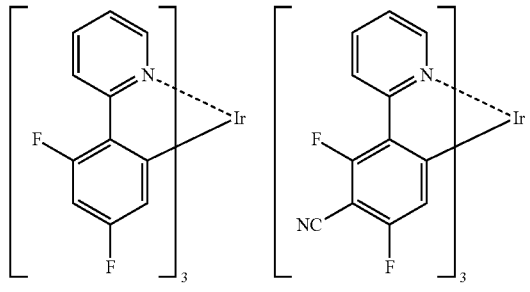

General Formula (E-9)

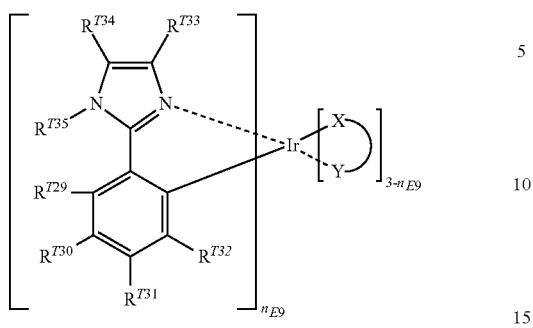

In the general formula (E-9), $R^{T29}$ to $R^{T34}$, (X—Y) and $n_{E8-}$ have the same definitions as $R^{T1}$ to $R^{T6}$, (X—Y) and $n_{E3}$ in the general formula (E-3). $R^{T35}$ represents a substituent, and as the substituent, the above-mentioned Substituent Group B is exemplified. Any adjacent two of $R^{T29}$ to $R^{T35}$ may be bound to each other to form a fused 4- or 7-membered ring, the fused 4- or 7-membered ring is cycloalkene, cycloalkadiene, aryl or heteroaryl, and the fused 4- or 7-membered ring may further have a substituent represented by the Substituent Group A.

When $n_{E7}$ is 2 or 3, two or three ligands each containing $R^{T1}$, $R^{T2}$, $R^{T3}$, $R^{T4}$, $R^{T5}$, $R^{T6}$, $R^{T7}$ and R"" exist, but the ligands may be the same as or different from one another.

$R^{T29}$ to $R^{T34}$ each are preferably a hydrogen atom, an alkyl group, an aryl group or a cyano group. $R^{T35}$ is preferably an alkyl group or an aryl group. $R^{T35}$ is preferably connected to $R^{T29}$ to form a ring. $R^{T35}$ and $R^{T29}$ are preferably bound together via an aryl group to result in forming a nitrogen-containing 6-membered ring. The aryl group connected to $R^{T35}$ and $R^{T29}$ may further have a substituent, and from the viewpoint of durability, the aryl group is preferably substituted with an alkyl group.

Specific preferred examples of the compound represented by the general formula (E-9) are listed below, but the compound is not limited thereto.

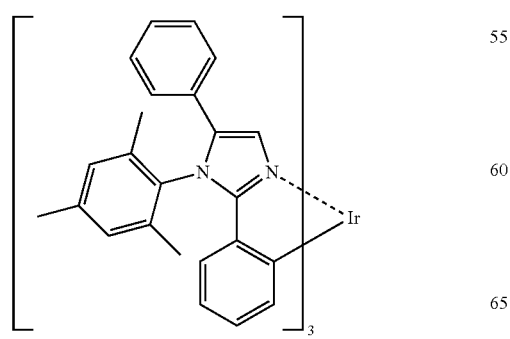

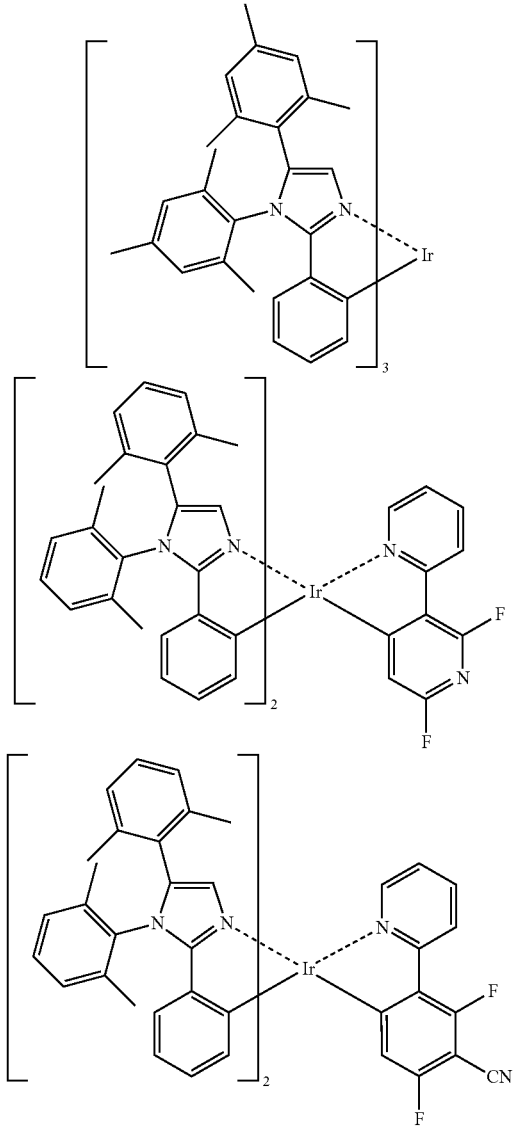

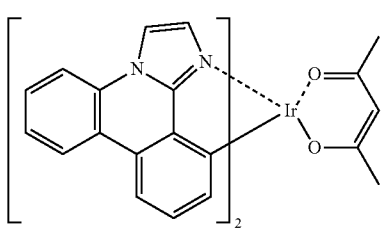

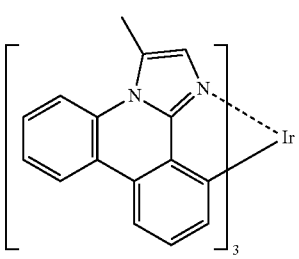

101
-continued
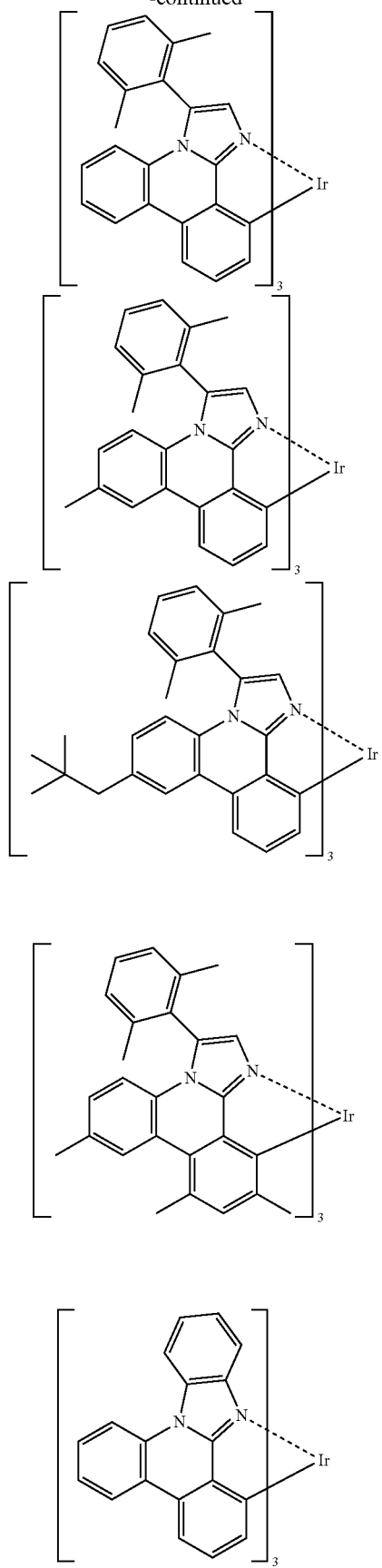
102
-continued
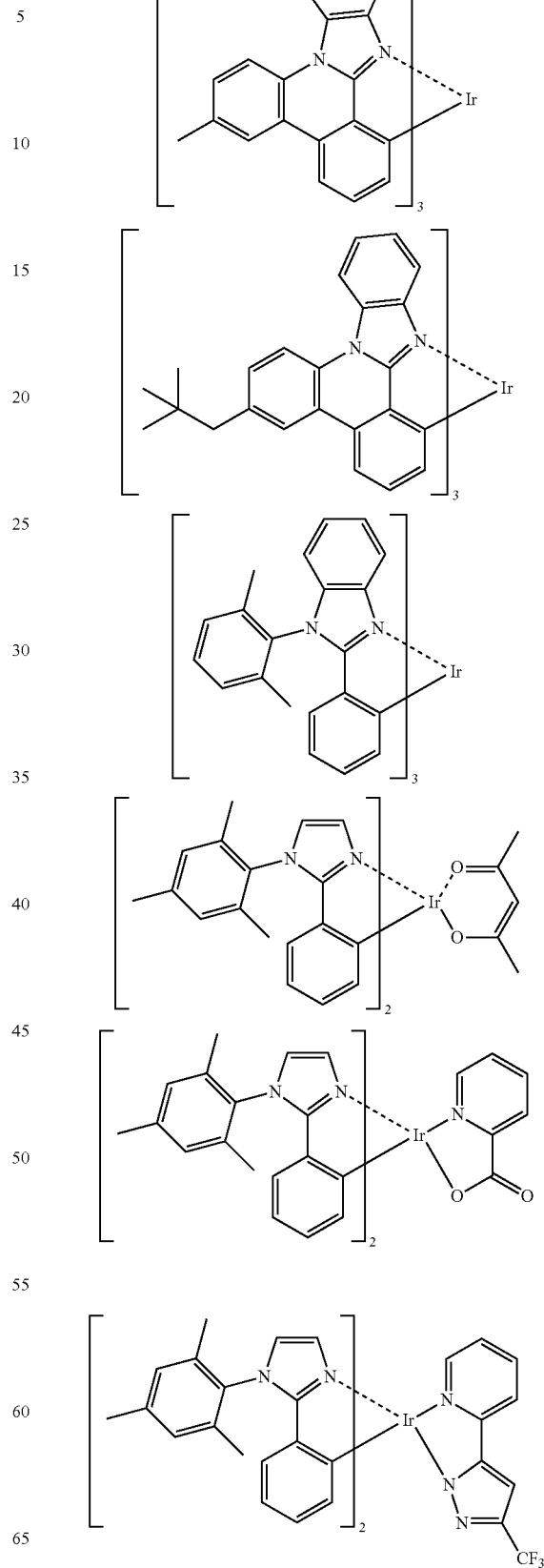

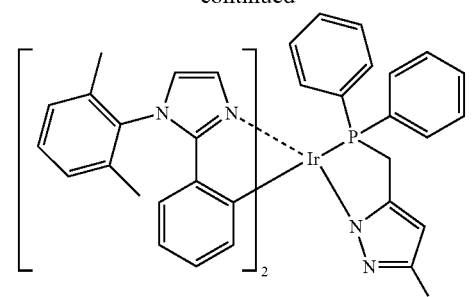
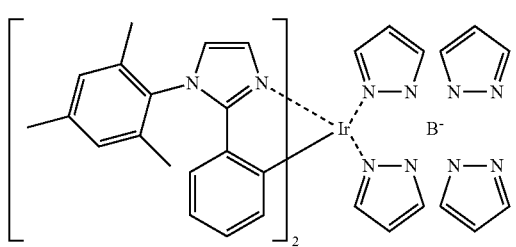
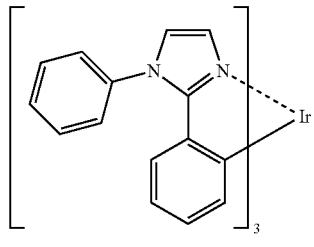
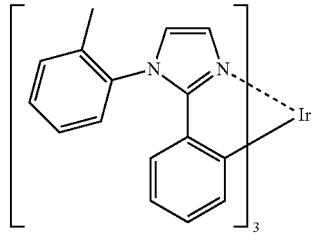
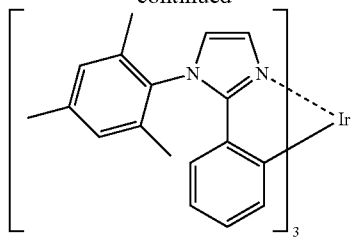
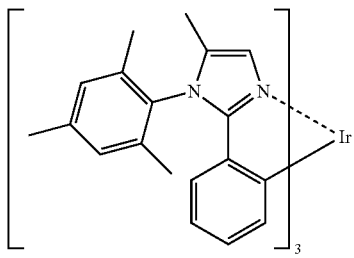
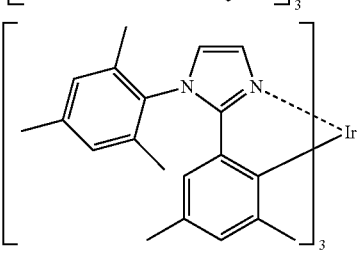
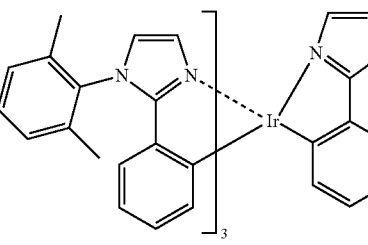
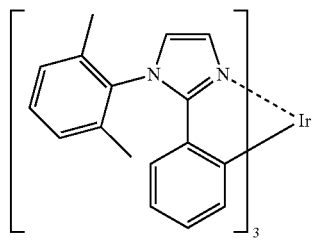
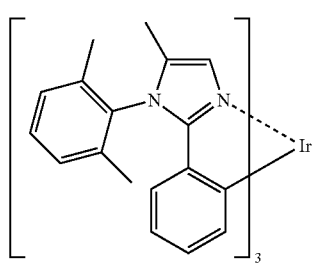
Specific preferred examples of the compound represented by the general formula (E-1) other than those shown above are listed below, but the compound is not limited thereto.
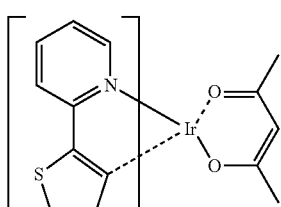
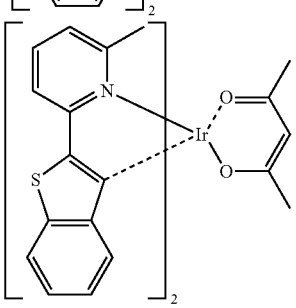

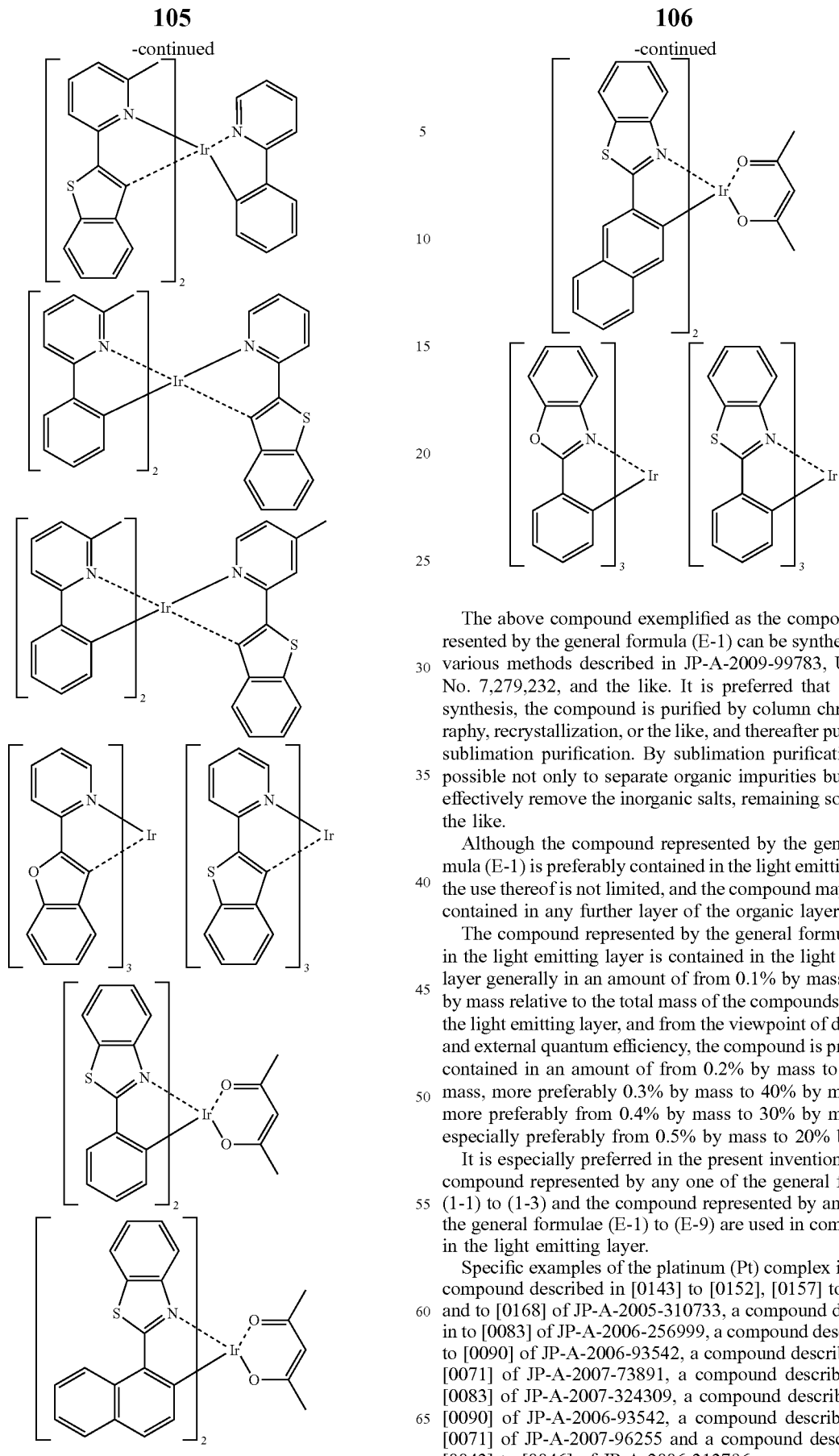

The above compound exemplified as the compound represented by the general formula (E-1) can be synthesized by various methods described in JP-A-2009-99783, U.S. Pat. No. 7,279,232, and the like. It is preferred that after the synthesis, the compound is purified by column chromatography, recrystallization, or the like, and thereafter purified by sublimation purification. By sublimation purification, it is possible not only to separate organic impurities but also to effectively remove the inorganic salts, remaining solvent, or the like.

Although the compound represented by the general formula (E-1) is preferably contained in the light emitting layer, the use thereof is not limited, and the compound may also be contained in any further layer of the organic layers.

The compound represented by the general formula (E-1) in the light emitting layer is contained in the light emitting layer generally in an amount of from 0.1% by mass to 50% by mass relative to the total mass of the compounds forming the light emitting layer, and from the viewpoint of durability and external quantum efficiency, the compound is preferably contained in an amount of from 0.2% by mass to 50% by mass, more preferably 0.3% by mass to 40% by mass, still more preferably from 0.4% by mass to 30% by mass, and especially preferably from 0.5% by mass to 20% by mass.

It is especially preferred in the present invention that the compound represented by any one of the general formulae (1-1) to (1-3) and the compound represented by any one of the general formulae (E-1) to (E-9) are used in combination in the light emitting layer.

Specific examples of the platinum (Pt) complex include a compound described in [0143] to [0152], [0157] to [0158], and to [0168] of JP-A-2005-310733, a compound described in to [0083] of JP-A-2006-256999, a compound described in to [0090] of JP-A-2006-93542, a compound described in to [0071] of JP-A-2007-73891, a compound described in to [0083] of JP-A-2007-324309, a compound described in to [0090] of JP-A-2006-93542, a compound described in to [0071] of JP-A-2007-96255 and a compound described in [0043] to [0046] of JP-A-2006-313796.

The thickness of the light emitting layer is not particularly limited, but it is usually from 2 nm to 500 nm, and above all, from the viewpoint of external quantum efficiency, it is more preferably from 5 nm to 200 nm, and still more preferably from 10 nm to 100 nm.

The light emitting layer in the organic electroluminescent element according to the present invention may be configured only of the light emitting material, or may have a configuration of the layer in which a host material and the light emitting material are mixed. A single, or two or more light emitting materials may be used. The host material is preferably a charge transporting material. A single material or two or more materials may be used as the host material. Examples thereof include a configuration in which an electron transporting host material and a hole transporting host material are mixed. Furthermore, the light emitting layer may contain a material which does not have charge transporting property and does not emit light.

In addition, the light emitting layer may be made of a single layer or multiple layers including two or more layers. The layers may all include the same light emitting material or host material, or also may include different materials for the respective layers. In the case where plural light emitting layers are present, the light emitting layers may emit light in different luminous colors from one another.

(Host Material)

The host material is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably not more than 5%, more preferably not more than 3%, and still more preferably not more than 1%, relative to the total amount of light emission in the whole of the element.

As the host material, the compound represented by any one of the general formula (1-1) to the general formula (1-3) can be used.

Other examples of the host material which can be used in the organic electroluminescent element according to the present invention include the following compounds:

pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, an aromatic tertiary amine compound, a styrylamine compound, a porphyrin-based compound, a fused aromatic hydrocarbon compound (such as fluorene, naphthalene, phenanthrene and triphenylene), a polysilane-based compound, a poly(N-vinylcarbazole), an aniline-based copolymer, a thiophene oligomer, a polythiophene and other conductive high molecular oligomers, organic silane, carbon film, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, a fluorine-substituted aromatic compound, heterocyclic tetracarboxylic anhydride of naphthalene, perylene or the like, phthalocyanine, various metal complexes typified by a metal complex of an 8-quinolinol derivative, metal phthalocyanine and a metal complex having a benzoxazole or benzothiazole as a ligand, derivatives thereof (which may have a substituent or a fused ring), and the like.

Among them, carbazole, dibenzothiophene, dibenzofuran, arylamine, a fused aromatic hydrocarbon compound and a metal complex are especially preferred.

In the light emitting layer in the organic electroluminescent element according to the present invention, the host material which can be used together may be a hole transporting host material or an electron transporting host material.

In the light emitting layer, it is preferred that the triplet minimum excited energy ($T_1$ energy) in the film state of the host material is higher than $T_1$ energy of the phosphorescence emitting material in terms of the color purity, luminous efficiency, and driving durability. The $T_1$ of the host material is preferably higher than the $T_1$ of the phosphorescence emitting material by 0.1 eV or more, more preferably by 0.2 eV or more, and still more preferably by 0.3 eV or more.

Since the light emission is quenched when $T_1$ of the host material in the film state is lower than $T_1$ of the phosphorescence emitting material, the host material is required to have a higher $T_1$ than the phosphorescence emitting material. Even in the case where the host material has a higher $T_1$ than the phosphorescence emitting material, when the difference between both $T_1$s is small, reverse energy transfer from the phosphorescence emitting material to the host material partially occurs to cause a deterioration in efficiency and durability. Accordingly, a host material is demanded that has a sufficiently high $T_1$ and has favorable chemical stability and carrier injecting and transporting properties.

Content of the host compound in the light emitting layer in the organic electroluminescent element according to the present invention is not particularly limited, but is preferably 15% by mass to 95% by mass relative to the total mass of the compounds constituting the light emitting layer, from the viewpoint of the luminous efficiency and the driving voltage. When the light emitting layer contains plural host compounds containing the compound represented by any one of the general formula (1-1) to the general formula (1-3), the compound represented by any one of the general formula (1-1) to the general formula (1-3) preferably accounts for 50% by mass to 99% by mass of the total host compounds.

(Other Layers)

The organic electroluminescent element according to the present invention may include layers other than the light emitting layer.

Examples of the organic layer other than the light emitting layer which may be included in the organic layers include a hole injecting layer, a hole transporting layer, a blocking layer (e.g., a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/blocking layer/electron transporting layer/cathode Anode/hole injecting layer/hole transporting layer/light emitting layer/electron transporting layer/electron injecting layer/cathode Anode/hole injecting layer/hole transporting layer/light emitting layer/blocking layer/electron transporting layer/electron injecting layer/cathode Anode/hole injecting layer/hole transporting layer/blocking layer/light emitting layer/blocking layer/electron transporting layer/electron injecting layer/cathode The organic electroluminescent element according to the present invention preferably includes at least one (A) organic layer which is preferably disposed between the anode and the light emitting layer. Examples of the (A) organic layer which is preferably disposed between the anode and the light emitting layer include an hole injecting layer, a hole transporting layer, and an electron blocking layer from the anode side.

The organic electroluminescent element according to the present invention preferably includes at least one (B) organic layer which is preferably disposed between the cathode and the light emitting layer. Examples of the (B) organic layer which is preferably disposed between the cathode and the light emitting layer include an electron injecting layer, an electron transporting layer, and a hole blocking layer from the cathode side.

Specifically, an example of the preferred embodiments of the organic electroluminescent element according to the present invention is the embodiment shown in FIG. 1, in which a hole injecting layer 4, a hole transporting layer 5, a light emitting layer 6, a hole blocking layer 7, and an electron transporting layer 8 are laminated as the organic layers, in this order from the anode 3 side.

These layers other than the light emitting layer which the organic electroluminescent element according to the present invention may have are hereunder described.

(A) Organic Layer Preferably Disposed Between Anode and Light Emitting Layer:

First, the (A) organic layer preferably disposed between the anode and the light emitting layer is described.

(A-1) Hole Injecting Layer and Hole Transporting Layer:

The hole injecting layer and the hole transporting layer are layers having a function of receiving holes from the anode or the anode side and transporting them to the cathode side.

For the hole injecting layer and the hole transporting layer, the matters described in paragraphs [0165] to [0167] of JP-A-2008-270736 can be applied to the present invention. Among them, materials which are preferably used as a hole injecting layer or a hole transporting layer are described.

The organic electroluminescent element according to the present invention preferably contains the following compound in organic layers between the light emitting layer and the anode, and more preferably in a hole injecting layer.

Specifically, a compound having the following structure is preferred.

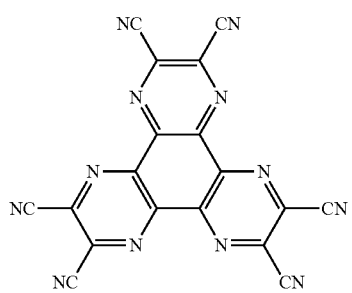

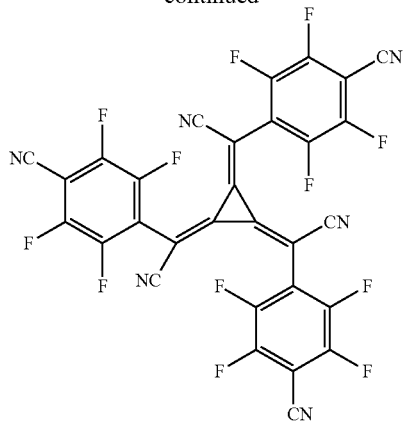

The organic electroluminescent element according to the present invention preferably contains at least one compound represented by any one of the following general formula (HT-1) and the general formula (1-1) to the general formula (1-3) in an organic layer between the light emitting layer and the anode, more preferably in a hole transporting layer or an electron blocking layer.

Examples of the hole transporting material include a triarylamine compound represented by the following general formula (HT-1):

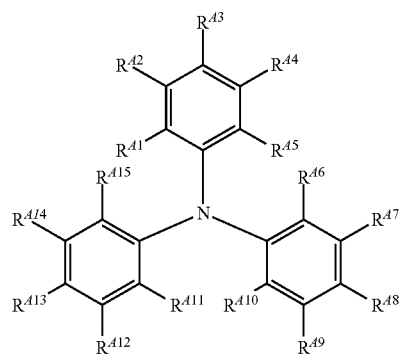

General Formula (HT-1)

[wherein in the general formula (HT-1), $R^{A1}$ to $R^{A15}$ represent a hydrogen atom or a substituent].

Examples of the substituent represented by $R^{A1}$ to $R^{A15}$ include substituents exemplified in the Substituent Group A, and adjacent substituents may be bound together via a single bond or a linking group to form a ring. From the viewpoint of the heat resistance and durability, at least one of $R^{A1}$ to $R^{A5}$ and at least one of $R^{A6}$ to $R^{A10}$ are each an aryl group.

Specific examples of the general formula (HT-1) are shown below, but the present invention is not limited thereto.

111
(HTL-1)
112
(HTL-2)
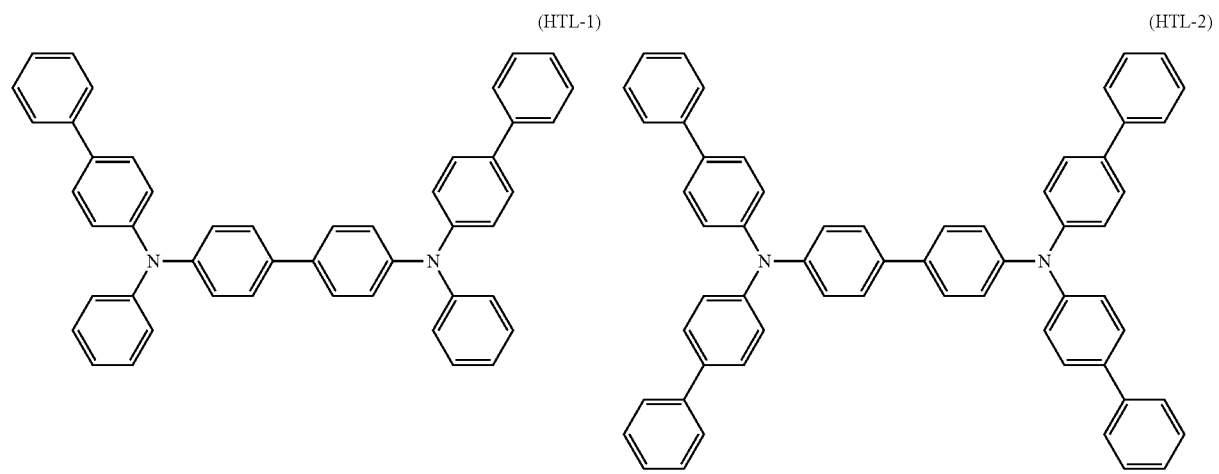
(HTL-3)
(HTL-4)
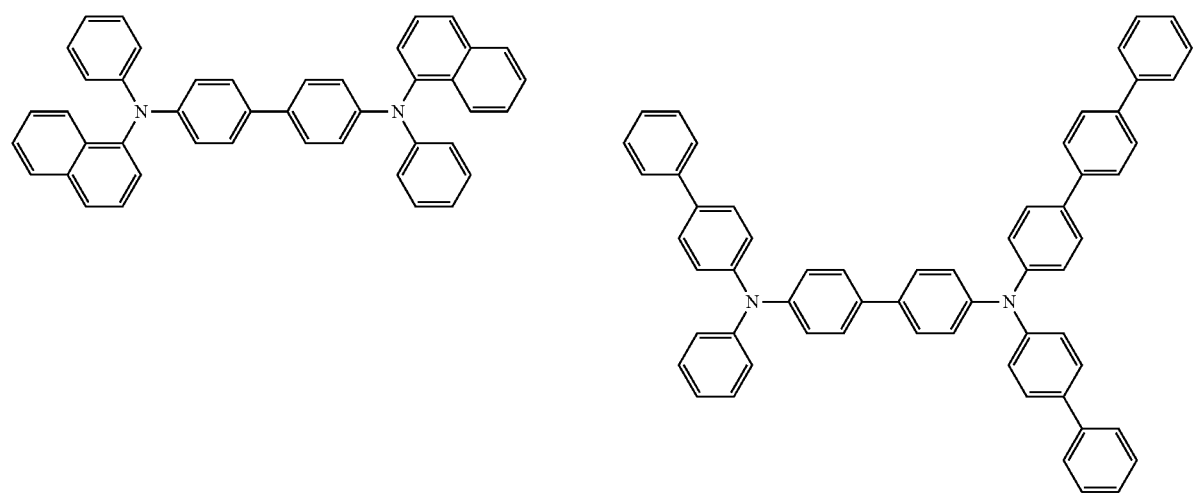
(HTL-5)
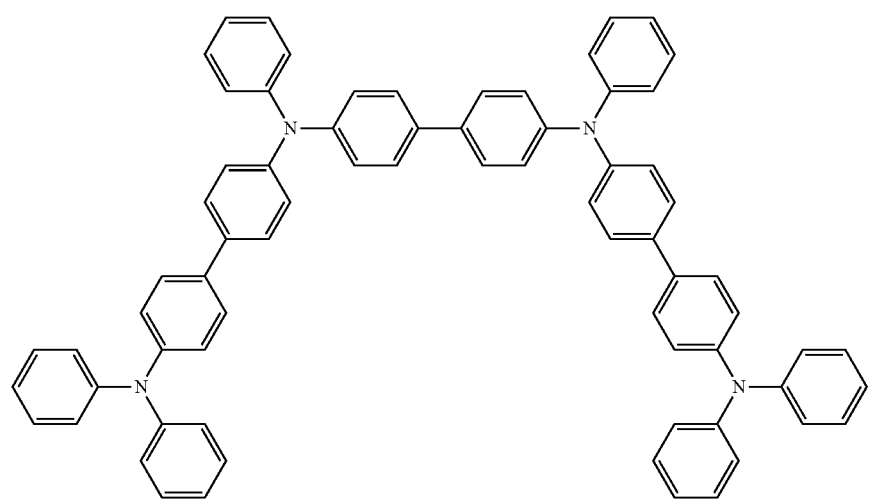

-continued
(HTL-6)
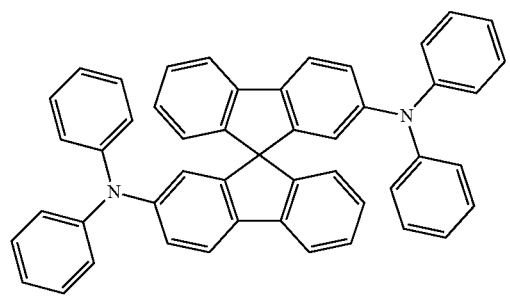
(HTL-7)
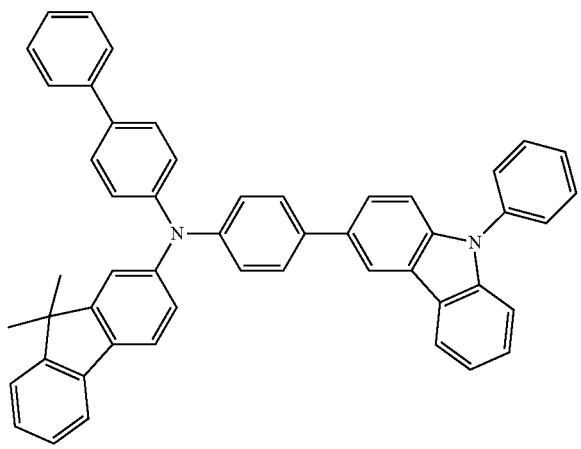
(HTL-8)
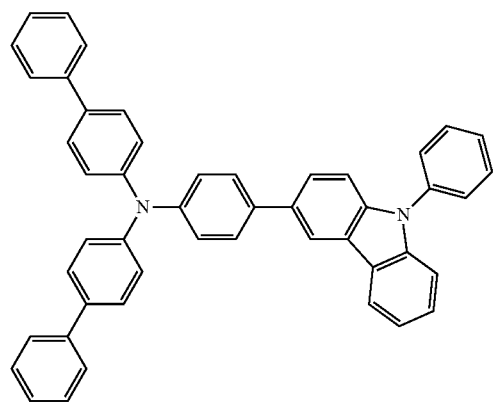
(HTL-9)
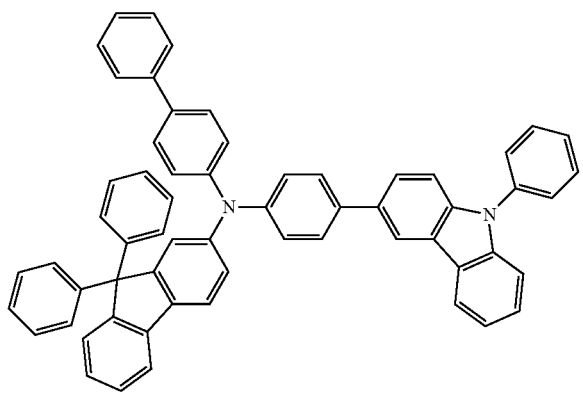
(HTL-10)
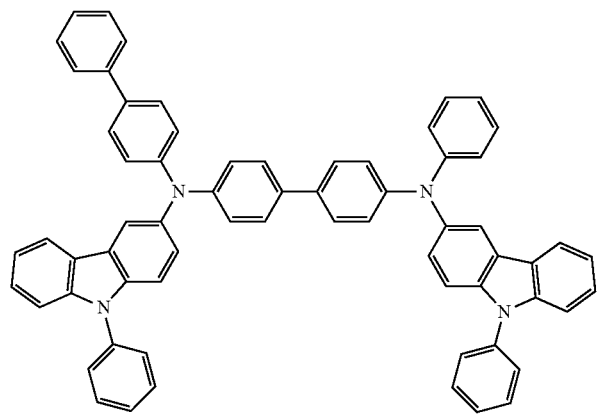
(HTL-11)
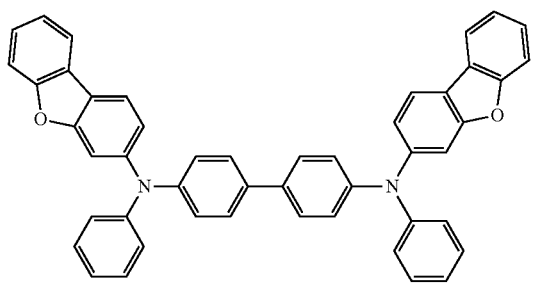
(HTL-12)
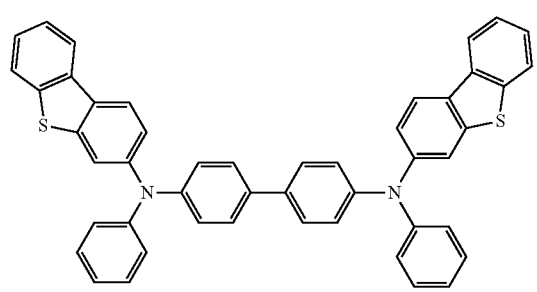
(HTL-13)
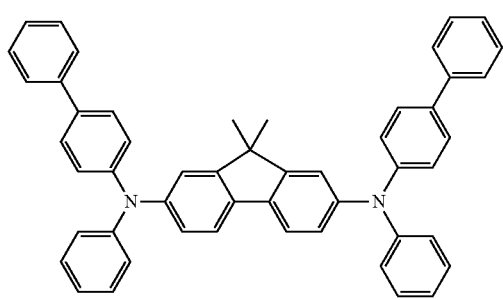

(HTL-14)

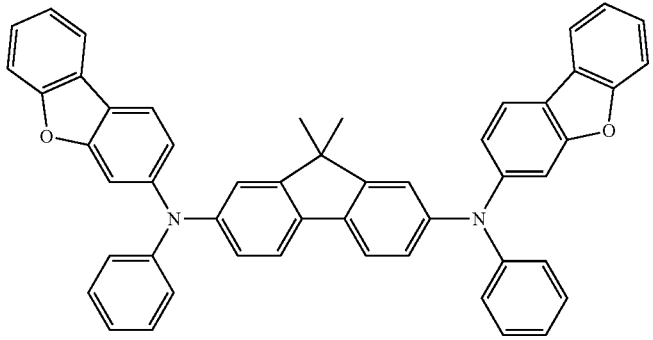

When the compound represented by the general formula (HT-1) is used in a hole transporting layer, the compound represented by the general formula (HT-1) is preferably contained in an amount of 50 to 100% by mass, more preferably 80 to 100% by mass, and especially preferably 95 to 100% by mass.

When the compound represented by the general formula (HT-1) is used in plural organic layers, the compound is preferably contained in an amount within the above range in each layer.

A single compound represented by the general formula (HT-1) may be contained in any organic layer, or plural compounds represented by the general formula (HT-1) may be contained in combination in an arbitrary ratio.

The thickness of the hole transporting layer containing the compound represented by the general formula (HT-1) is preferably 1 nm to 500 nm, more preferably 3 nm to 200 nm, and still more preferably 5 nm to 100 nm. In addition, the hole transporting layer is preferably provided in contact with the light emitting layer.

The hole transporting layer may have either a single layer structure composed of a single material or two or more materials selected from the above-exemplified materials, or a multilayer structure composed of a plurality of layers having the same composition or different compositions.

The compound represented by the general formula (HT-1) preferably has a minimum excited triplet ($T_1$) energy in the film state of 2.52 eV (58 kcal/mol) to 3.47 eV (80 kcal/mol), more preferably of eV (57 kcal/mol) to 3.25 eV (75 kcal/mol), and still more preferably of 2.52 eV (58 kcal/mol) to 3.04 eV (70 kcal/mol).

The hydrogen atoms constituting the general formula (HT-1) may include hydrogen isotopes (deuterium or the like). In this case, all the hydrogen atoms in the compound may be replaced by the hydrogen isotope atoms, or the compound may be a mixture in which a part of the compound contains some hydrogen isotopes.

The compound represented by the general formula (HT-1) can be synthesized by combining various known synthesis methods. Most commonly, for the carbazole compound, a synthetic method may be exemplified in which a fused compound of an arylhydradine and a cyclohexane derivative is subjected to the Aza-Cope rearrangement reaction, and thereafter converted into an aromatic compound by dehydrogenating (written by L. F. Tieze and Th. Eicher, translated by Takano and Ogasawara, Seimitsu Yuuki Gousei, p 339 (Nankodo)). For a coupling reaction of the resulting carbazole compound with a halogenated aryl compound using a palladium catalyst, a method is exemplified which is described in Tetrahedron Letters, vol. 39, p 617 (1998); vol. 39, p 2367 (1998); vol. 40, p 6393 (1999); etc. The reaction temperature and the reaction time are not particularly limited and the conditions described in the above documents may be applied.

The compound represented by the general formula (HT-1) in the present invention is preferably formed into a thin film by a vacuum vapor deposition process, but a wet process such as a solution coating can be suitably used. The molecular weight of the compound is preferably 2000 or less, more preferably 1200 or less, and especially preferably 800 or less, from the viewpoint of applicability to the vapor deposition and solubility. In terms of the applicability to the vapor deposition, too small molecular weight causes decrease of the vapor pressure, thereby inhibiting the conversion from the vapor phase to the solid phase, so that it become difficult to form the organic layer. Accordingly, the molecular weight is preferably 250 or more, and especially preferably 300 or more.

(A-2) Electron Blocking Layer:

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of a single material or two or more materials selected from the above-exemplified materials or a multilayer structure composed of a plurality of layers having the same composition or different compositions.

The material used for the electron blocking layer preferably has a $T_1$ energy higher than that of the phosphorescence emitting material in terms of the color purity, luminous efficiency and driving durability. The $T_1$ in the film state of the material used for the electron blocking layer is preferably higher than the $T_1$ of the phosphorescence emitting material by 0.1 eV or more, more preferably by 0.2 eV or more, and still more preferably by 0.3 eV or more.

(B) Organic Layer Preferably Disposed Between Cathode and Light Emitting Layer:

Next, the (B) organic layer preferably disposed between the cathode and the light emitting layer is described.

(B-1) Electron Injecting Layer and Electron Transporting Layer:

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by any one of the general formula (1-1) to the general formula (1-3) can be used. A preferred embodiment of this case is the same as the above description of the case where the compound represented by any one of the general formula (1-1) to the general formula (1-3) is contained in a layer other than the light emitting layer. These layers also preferably contain, as an other electron transporting material, pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, aromatic ring tetracarboxylic acid anhydrides of naphthalene, perylene and the like, phthalocyanine derivatives, various metal complexes typified by metal complexes of 8-quinolinol derivatives, metal phthalocyanine and metal complexes having benzoxazole or benzothiazole as a ligand thereof, organic silane derivatives typified by silole, and the like.

From the viewpoint of decreasing the driving voltage, the thickness of each of the electron injecting layer and the electron transporting layer is preferably not more than 500 nm.

The thickness of the electron transporting layer is preferably from 1 nm to 500 nm, more preferably from 5 nm to 200 nm, and still more preferably from 10 nm to 100 nm. The thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of a single material or two or more materials selected from the above-exemplified materials or a multilayer structure composed of a plurality of layers having the same composition or different compositions.

The electron injecting layer preferably contains an electron donating dopant. By incorporating the electron donating dopant into the electron injecting layer, for example, there are brought such effects that the electron injecting properties are enhanced; that the driving voltage is lowered; and that the efficiency is enhanced. The electron donating dopant may be any one of organic materials and inorganic materials as long as it is capable of giving electrons to the material to be doped and generating radical anions. Examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably from 0.5% by mass to 30% by mass relative to the total mass of the compounds forming the electron injecting layer.

(B-2) Hole Blocking Layer:

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order to inhibit the energy transfer of excitons generated in the light emitting layer to prevent degradation of luminous efficiency, $T_1$ energy in the film state of the organic compound constituting the hole blocking layer is preferably higher than the $T_1$ energy of the light emitting material.

As an example of the organic compound constituting the hole blocking layer, for example, the compound represented by any one of the general formula (1-1) to the general formula (1-3) can be used.

Examples of the organic compounds constituting the hole blocking layer, other than the compound represented by any one of the general formula (1-1) to the general formula (1-3), include aluminum complexes such as aluminum(III) bis(2-methyl-8-quinolinato) 4-phenylphenolate (abbreviated as "Balq"), triazole derivatives, phenanthroline derivatives such as 2,9-dimethyl-4,7-diphenyl-1,10-phenanthroline (abbreviated as "BCP"), the compound of the present invention, and the like. In the present invention, the function of the hole blocking layer is not limited to the function of actually blocking the holes, and the hole blocking layer may have a function to prevent the excitons in the light emitting layer from diffusing to the electron transporting layer, or a function to block quenching due to energy transfer. The compound of the present invention is preferably applied to the hole blocking layer.

The thickness of the hole blocking layer is preferably from 1 nm to 500 nm, more preferably from 5 nm to 200 nm, and still more preferably from 10 nm to 100 nm.

The hole blocking layer may have either a single layer structure composed of a single material or two or more materials selected from the above-exemplified materials or a multilayer structure composed of a plurality of layers having the same composition or different compositions.

The material which is used in the hole blocking layer preferably has a higher $T_1$ energy than that of the phosphorescence emitting material in view of the color purity, luminous efficiency, and driving durability. The $T_1$ energy in the film state of the material used for the hole blocking layer is preferably higher than the $T_1$ of the phosphorescence emitting material by 0.1 eV or more, more preferably by 0.2 eV or more, and still more preferably by 0.3 eV or more.

(B-3) Material Especially Preferably Used in Organic Layer which is Preferably Disposed Between Cathode and Light Emitting Layer:

In the organic electroluminescent element according to the present invention, examples of the material which is especially preferably used in the materials for the (B) organic layer preferably disposed between the cathode and the light emitting layer include the compound represented by any one of the general formula (1-1) to the general formula (1-3), and a compound represented by the following general formula (O-1).

The compound represented by the general formula (O-1) is hereunder described.

The organic electroluminescent element according to the present invention preferably contains at least one organic layer between the light emitting layer and the cathode, and it is preferred that the organic layer contains at least one compound represented by the following general formula (O-1) from the view point of the element efficiency and driving voltage. The general formula (O-1) is hereunder described.

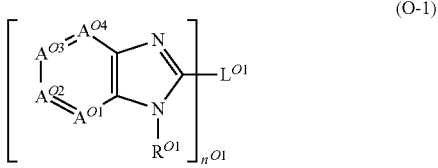

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group or a heteroaryl group, and plural $R^A$s may be the same as or different from one another. $L^{O1}$ represents a divalent to hexavalent linking group composed of an aryl ring or a heteroaryl ring. $n^{O1}$ represents an integer of from 2 to 6.)

$R^{O1}$ represents an alkyl group (preferably having from 1 to 8 carbon atoms), an aryl group (preferably having from 6 to 30 carbon atoms), or a heteroaryl group (preferably having from 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group. Among them, an alkyl group or an aryl group is more preferred, with an aryl group being still more preferred. In the case where the aryl group of $R^{O1}$ has plural substituents, the plural substituents may be bound to each other to form a 5- or 6-membered ring. The aryl group of $R^{O1}$ is preferably a phenyl group which may have a substituent selected from the Substituent Group A, more preferably a phenyl group which may be substituted with an alkyl group or an aryl group, and still more preferably an unsubstituted phenyl group or a 2-phenylphenyl group.

$A^{O1}$ to $A^{O4}$ each independently represent C—$R^A$ or a nitrogen atom. It is preferred that from zero to two of $A^{O1}$ to $A^{O4}$ are nitrogen atoms; and it is more preferred that zero or one of $A^{O1}$ to $A^{O4}$ is a nitrogen atom. It is preferred that all of $A^{O1}$ to $A^{O4}$ are C—Rs$^A$, or $A^{O1}$ is a nitrogen atom, and $A^{O2}$ to $A^{O4}$ are C—Rs$^A$; it is more preferred that $A^{O1}$ is a nitrogen atom, and $A^{O2}$ to $A^{O4}$ are C—Rs$^A$; and it is still more preferred that $A^{O1}$ is a nitrogen atom, $A^{O2}$ to $A^{O4}$ are C—Rs$^A$, and $R^A$s are all hydrogen atoms.

$R^A$ represents a hydrogen atom, an alkyl group (preferably having from 1 to 8 carbon atoms), an aryl group (preferably having from 6 to 30 carbon atoms), or a heteroaryl group (preferably having from 4 to 12 carbon atoms), and may have a substituent selected from the above-described Substituent Group A. In addition, plural $R^A$s may be the same as or different from one another. $R^A$ is preferably a hydrogen atom or an alkyl group, and more preferably a hydrogen atom.

$L^{O1}$ represents a divalent to hexavalent linking group composed of an aryl ring (preferably having from 6 to 30 carbon atoms) or a heteroaryl ring (preferably having from 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in the case where $L^{O1}$ has a substituent, the substituent is preferably an alkyl group, an aryl group, or a cyano group. Specific examples of $L^{O1}$ include the following.

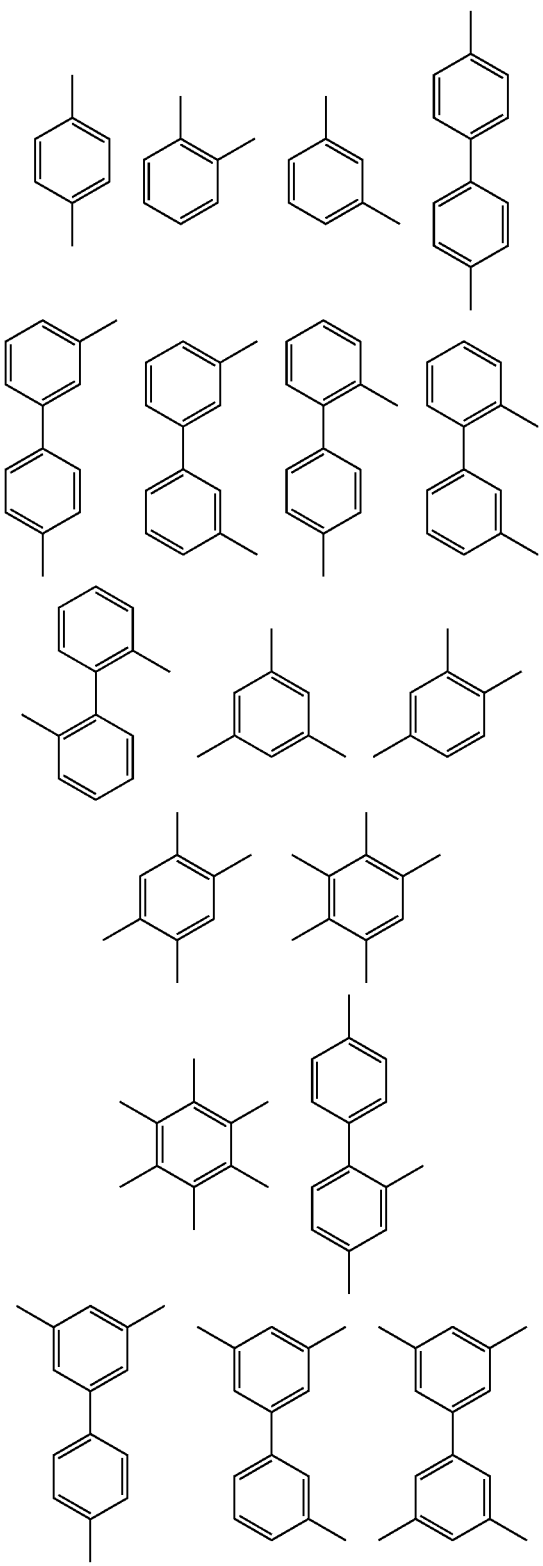

-continued

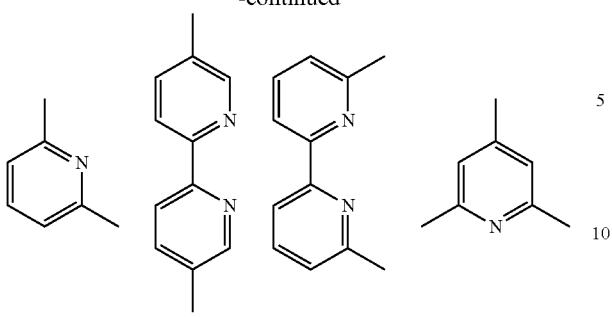

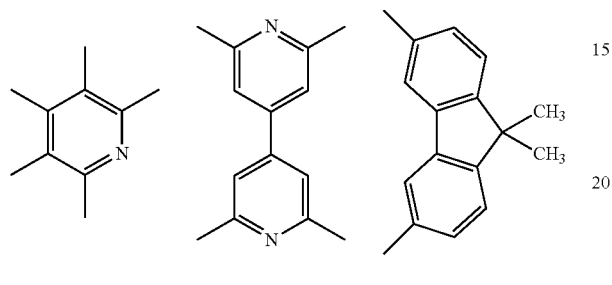

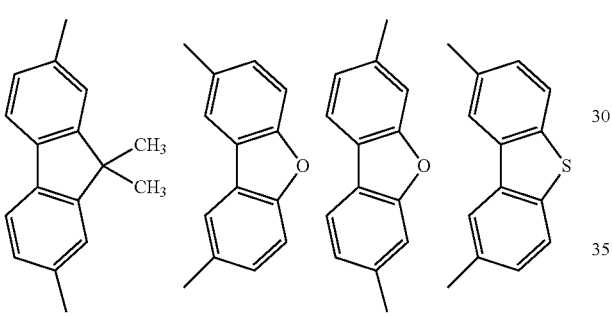

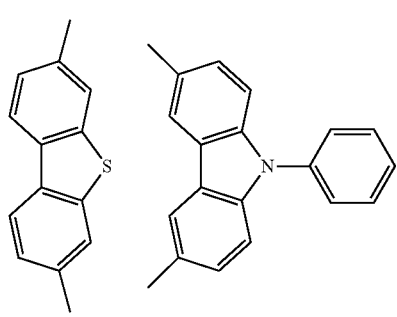

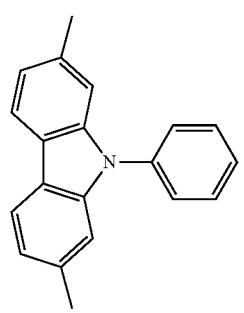

$n^{O1}$ represents an integer of from 2 to 6, preferably an integer of from 2 to 4, and more preferably 2 or 3. $n^{O1}$ is most preferably 3 from the viewpoint of efficiency of the element, and $n^{O1}$ is most preferably 2 from the viewpoint of durability of the element.

The compound represented by the general formula (O-1) is preferably a compound represented by the following general formula (O-2):

(O-2)

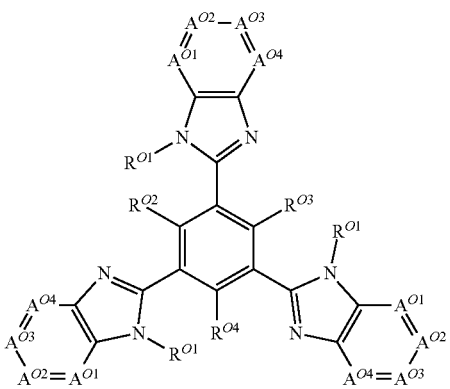

(wherein in the general formula (O-2), $R^{O1}$ represents an alkyl group, an aryl group or a heteroaryl group. $R^{O2}$ to $R^{O4}$ each independently represent a hydrogen atom, an alkyl group, an aryl group or a heteroaryl group. $A^{O1}$ to $A^{O4}$ each independently represent C—$R^{4}$ or a nitrogen atom. $R^{4}$ represents a hydrogen atom, an alkyl group, an aryl group or a heteroaryl group, and the plural $R^{4}$s may be the same as or different from one another).

$R^{O1}$ and $A^{O1}$ to $A^{O4}$ have the same definitions as $R^{O1}$ and $A^{O1}$ to $A^{O4}$ in the general formula (O-1) described above, and the preferred ranges thereof are also the same.

$R^{O2}$ to $R^{O4}$ each independently represent a hydrogen atom, an alkyl group (preferably having 1 to 8 carbon atoms), an aryl group (preferably having 6 to 30 carbon atoms), or a heteroaryl group (preferably having 4 to 12 carbon atoms), and these groups may have a substituent selected from the Substituent Group A described above. $R^{O2}$ to $R^{O4}$ are preferably a hydrogen atom, an alkyl group or an aryl group, more preferably a hydrogen atom or an aryl group, and most preferably a hydrogen atom.

The glass transition temperature (Tg) of the compound represented by the general formula (O-1) is preferably from 100° C. to 300° C., more preferably from 120° C. to 300° C., still more preferably from 120° C. to 300° C., and further still more preferably 140° C. to 300° C., from the viewpoint of stability at the time of storage at a high temperature, or stable operation during driving at a high temperature or against heat generation during driving.

Specific examples of the compound represented by the general formula (O-1) are hereunder described, but the compound used in the present invention is not limited thereto.

123          124
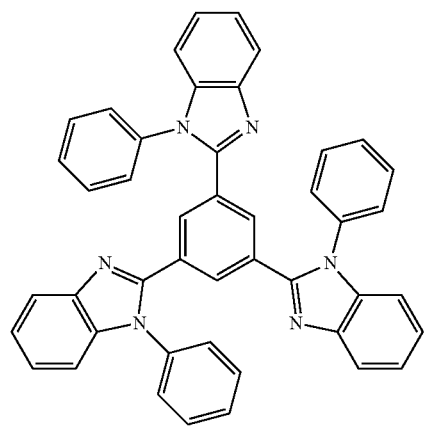
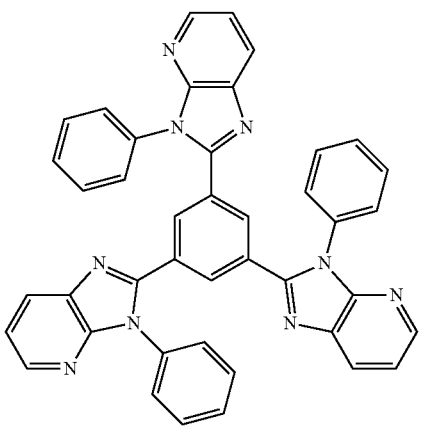
OM-1          OM-2
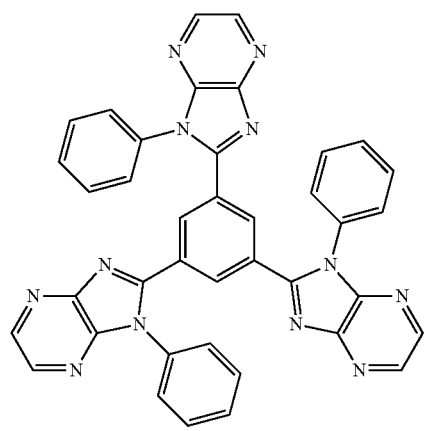
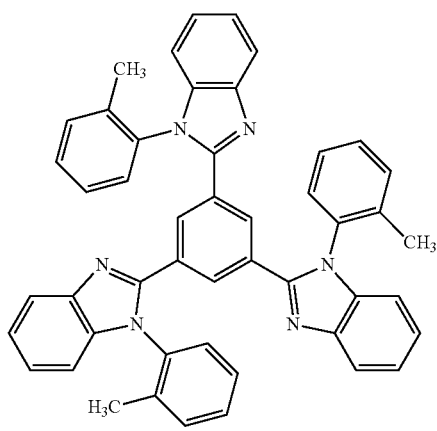
OM-3          OM-4
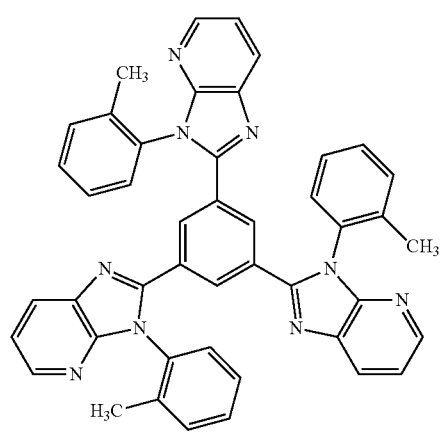
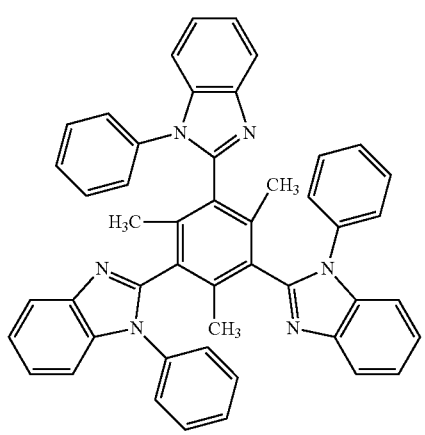
OM-5          OM-6

-continued
OM-7
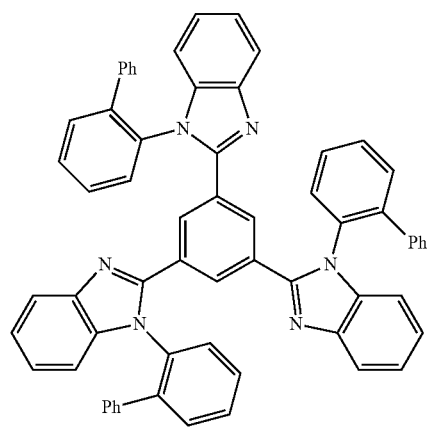
OM-8
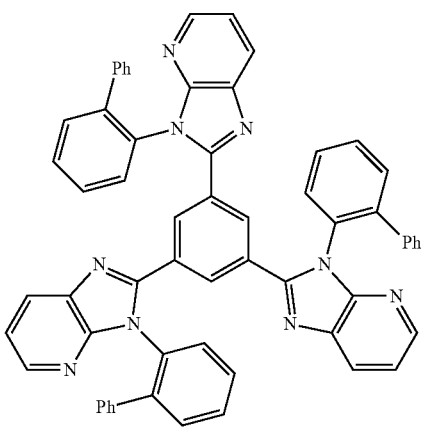
OM-9
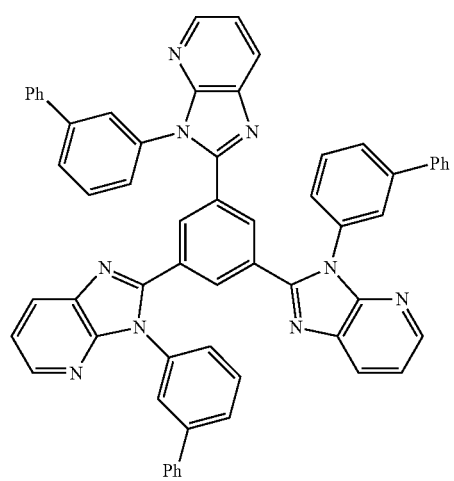
OM-10
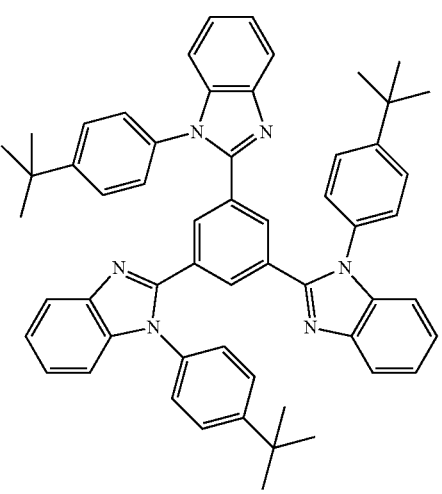
OM-11
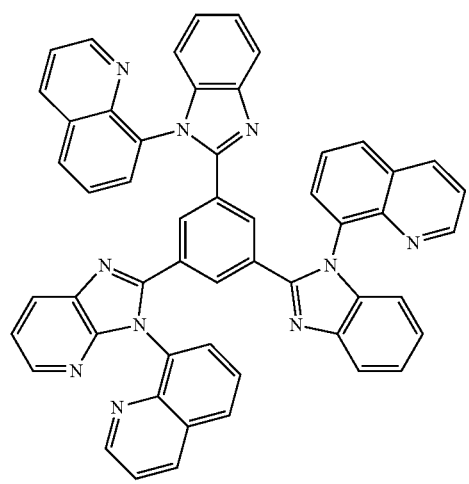
OM-12
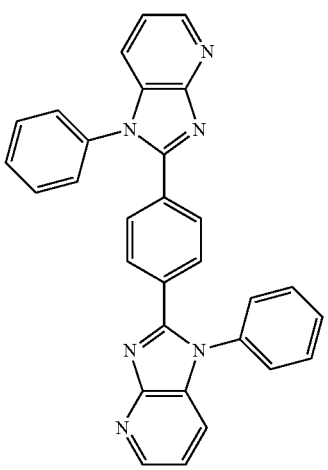

-continued
OM-13
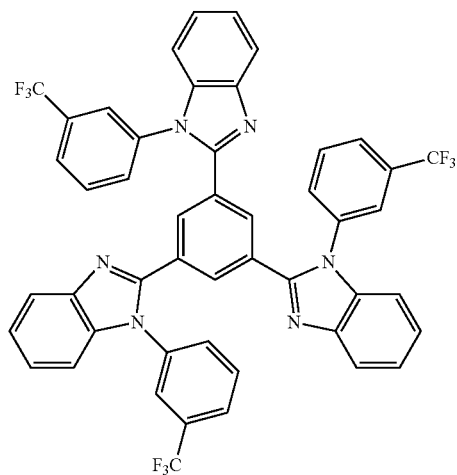
OM-14
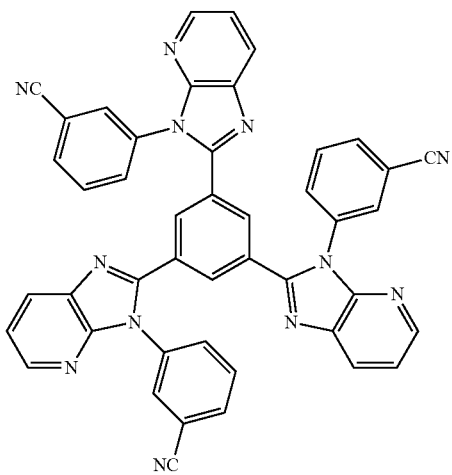
OM-15
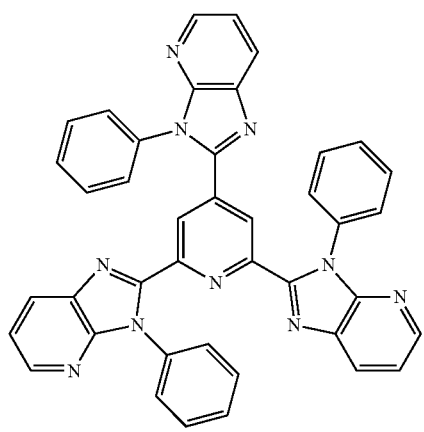
OM-16
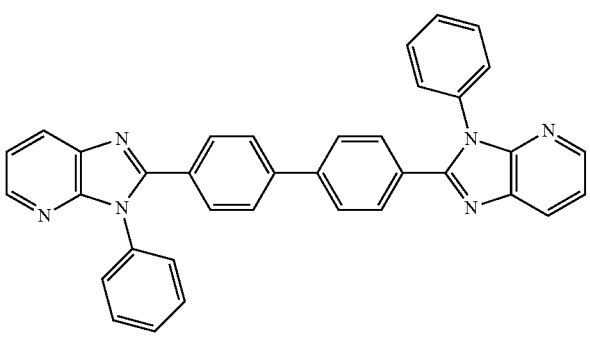
OM-17
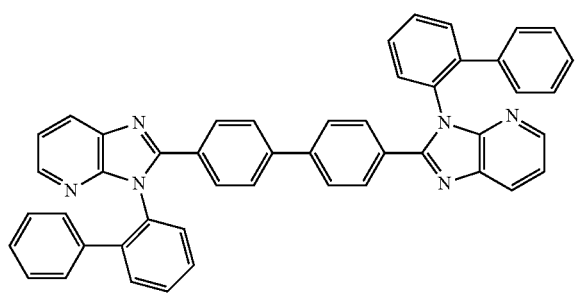
OM-18
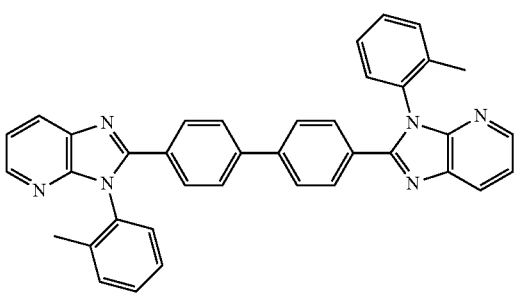
OM-19
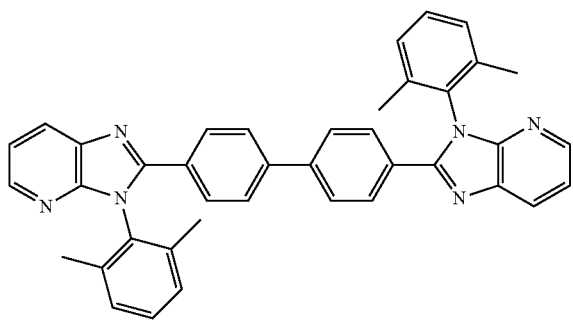
OM-20
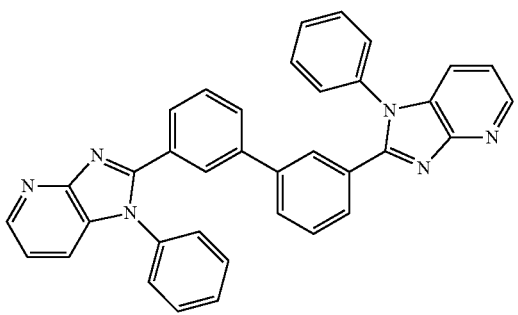

-continued

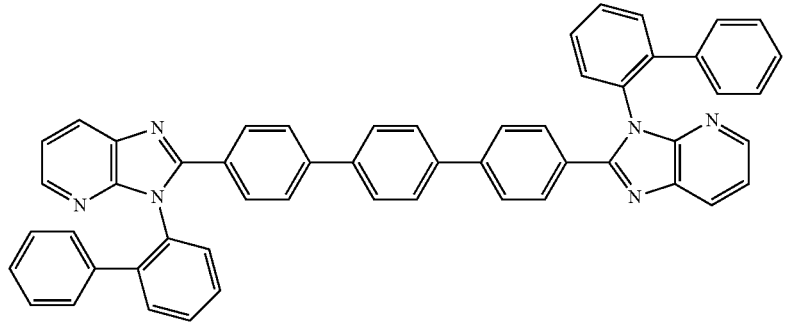

OM-21

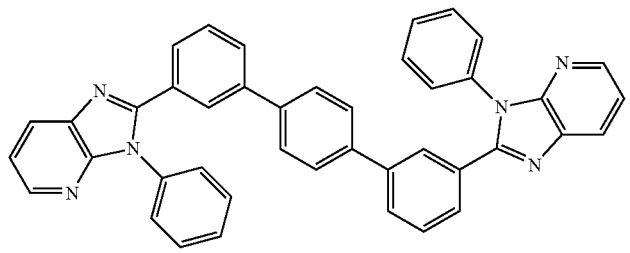

OM-22

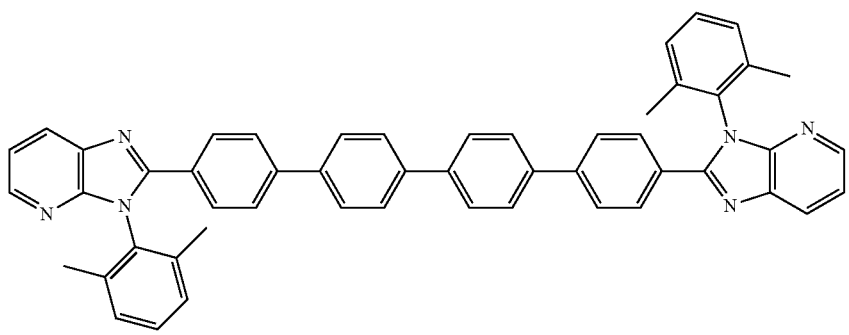

OM-23

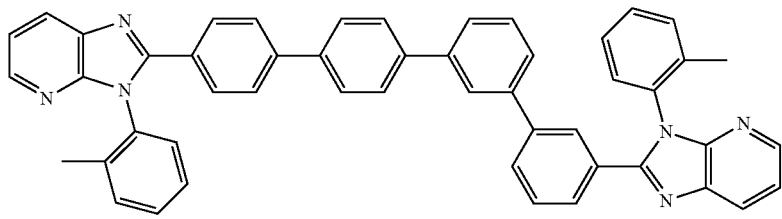

OM-24

The compound represented by the general formula (O-1) can be synthesized by the method described in JP-A-2001-335776. After the synthesis, it is preferred that the product is purified by column chromatography, recrystallization, reprecipitation, or the like, and then purified by sublimation purification. By sublimation purification, it is possible not only to separate organic impurities but also to effectively remove inorganic salts, remaining solvent, moisture, or the like.

In the organic electroluminescent element according to the present invention, the compound represented by the general formula (O-1) is preferably contained in an organic layer between the light emitting layer and the cathode, and more preferably contained in a layer adjacent to the light emitting layer on the cathode side.

The compound represented by the general formula (O-1) is preferably contained in an amount of 70 to 100% by mass, and more preferably 85 to 100% by mass, relative to the total mass of the organic layer to which the compound is to be added.

<Protective Layer>

In the present invention, the entirety of the organic electroluminescent element may be protected by a protective layer.

For the protective layer, the detailed description in paragraphs [0169] to [0170] of JP-A-2008-270736 can be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph [0171] of JP-A-2008-270736 can be applied to the present invention.

<Driving Method>

The organic electroluminescent element according to the present invention can emit light by applying a direct current (it may include an alternate current component, if desired) voltage (usually from 2 volts to 15 volts) or a direct current between the anode and the cathode.

For a driving method of the organic electroluminescent element according to the present invention, driving methods described in the descriptions or the like of JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element according to the present invention is preferably 7% or more, more preferably 10% or more, and still more preferably 12% or more. As for the numerical value of the external quantum efficiency, a maximum value of the external quantum efficiency obtained when the organic electroluminescent element is driven at 20° C., or a value of the external quantum efficiency in the vicinity of from 300 to 400 cd/m² obtained when the element is driven at 20° C. can be employed.

The internal quantum efficiency of the organic electroluminescent element according to the present invention is preferably 30% or more, more preferably 50% or more, and still more preferably 70% or more. The internal quantum efficiency of the element is calculated by dividing the external quantum efficiency by the light extraction efficiency. Though the light extraction efficiency in usual organic EL elements is about 20%, by adjusting the shape of a substrate, the shape of an electrode, the film thickness of an organic layer, the film thickness of an inorganic layer, the refractive index of an organic layer, the refractive index of an inorganic layer, or the like, it is possible to increase the light extraction efficiency to 20% or more.

<Emission Peak Wavelength>

The organic electroluminescent element according to the present invention has no limitation in its emission peak wavelength, and may be used for red light emission, green light emission, or blue light emission among the three primary colors of light. Among them, the organic electroluminescent element according to the present invention preferably has an emission peak wavelength of 500 to 700 nm from the viewpoint of the minimum excision triplet ($T_1$) energy of the compound represented by any one of the general formula (1-1) to the general formula (1-3).

In specific, in the organic electroluminescent element according to the present invention, in the case of using the compound represented by any one of the general formula (1-1) to the general formula (1-3) as a host material of the light emitting layer, a green phosphorescence emitting material is preferably used therewith, and the emission peak wavelength is preferably from 500 to 700 nm, more preferably from 520 to 650 nm, and especially preferably from 520 to 550 nm.

On the other hand, in the organic electroluminescent element according to the present invention, when the compound represented by any one of the general formula (1-1) to the general formula (1-3) is used as a charge transporting material for a hole blocking layer, the emission peak wavelength is preferably 400 to 700 nm, more preferably 450 to 650 nm, and especially preferably 500 to 650 nm.

<Use of Organic Electroluminescent Element According to the Present Invention>

The organic electroluminescent element according to the present invention can be suitably used for display elements, displays, backlights, electrophotography, illumination light sources, recording light sources, exposure light sources, readout light sources, signs, billboards, interior decorations, optical communications, and the like. In particular, it is preferably used for devices to be driven in a region of high-intensity luminescence, such as a light emitting device, an illumination device, and a display device.

[Light Emitting Device]

The light emitting device according to the present invention is characterized by comprising the organic electroluminescent element according to the present invention.

Next, the light emitting device of the present invention is described with reference to FIG. 2.

The light emitting device of the present invention is configured using the organic electroluminescent element described above.

FIG. 2 is a schematic cross sectional view of an example of the light emitting device of the present invention. A light emitting device 20 in FIG. 2 is composed of a substrate (supporting substrate) 2, an organic electroluminescent element 10, a sealing enclosure 16, and the like.

The organic electroluminescent element 10 is configured by sequentially laminating an anode (first electrode) 3, an organic layer 11 and a cathode (second electrode) 9, on the substrate 2. In addition, a protective layer 12 is laminated on the cathode 9, and further on the protective layer 12, the sealing enclosure 16 is provided via an adhesive layer 14. Incidentally, a part of each electrode 3 and 9, partition walls, an insulating layer, and the like are omitted.

As the adhesive layer 14 here, an epoxy resin or an other light curing adhesive or a thermosetting adhesive may be used, and for example, a thermosetting adhesive sheet may be used.

The use of the light emitting device of the present invention is not particularly limited, and the device may be used as a display device for an illumination device, as well as for a display device in a television, a personal computer, a cellular phone, an electronic paper, or the like.

[Illumination Device]

The illumination device according to the present invention is characterized by comprising the organic electroluminescent element according to the present invention.

Next, the illumination device of the present invention is described with reference to FIG. 3.

FIG. 3 is a schematic cross sectional view showing an example of the illumination device of the present invention. An illumination device 40 of the present invention includes the above-mentioned organic EL element 10 and a light scattering member 30, as shown in FIG. 3. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, the light scattering member 30 is a transparent substrate 31 containing fine particles 32 dispersed therein. As the transparent substrate 31, a glass substrate can be suitably exemplified, for example. As the fine particles 32, transparent resin fine particles can be suitably exemplified. Any known glass substrate and any known transparent resin fine particles may be used. When light emitted from the organic electroluminescent element 10 enters a light incidence plane 30A of the scattering member 30, such an illumination device 40 scatters the incident light on the light scattering member 30 to emit the scattered light from the light output plane 30B as the illumination light.

[Display Device]

The display device according to the present invention is characterized by comprising the organic electroluminescent element according to the present invention.

As the display device of the present invention, for example, a display device for a television, a personal computer, a cellular phone, an electronic paper, and the like is exemplified.

EXAMPLE

The present invention is hereunder described in more detail with reference to the following Examples. The materials, use amounts, ratios, treatment details, treatment procedures, and the like shown in the following Examples can be appropriately modified so far as the gist of the present invention is not deviated. Accordingly, it should not be construed that the scope of the present invention is limited to the specific examples shown below.

Example 1

Compounds used in Examples are shown below together with Comparative Compounds also used in the Examples.

Compound (1-1-1)

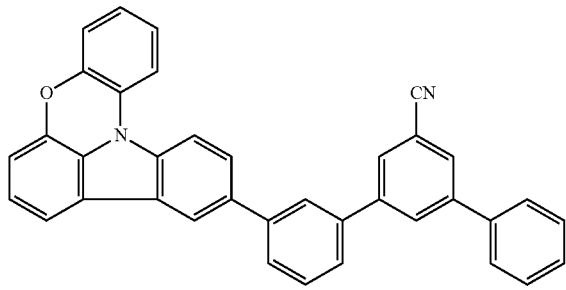

Compound (1-1-2)

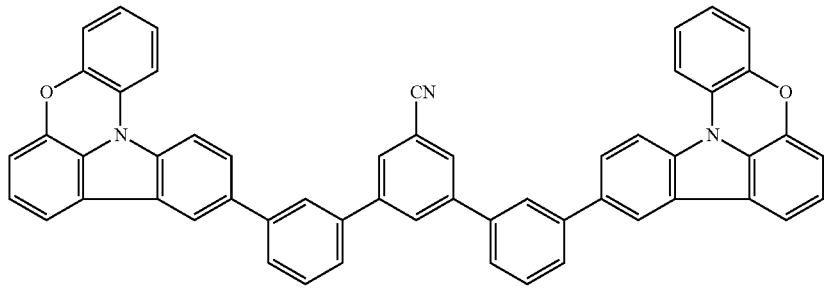

Compound (1-1-3)

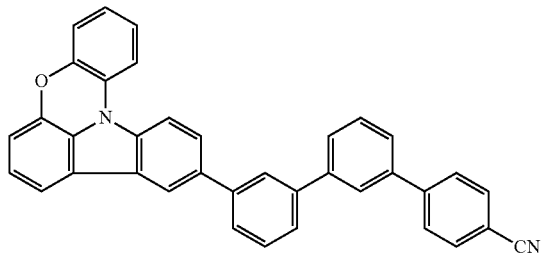

Compound (1-1-4)

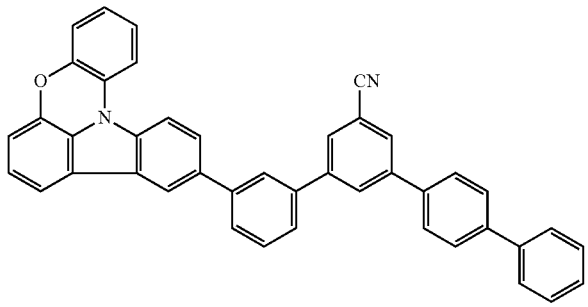

Compound (1-1-5)

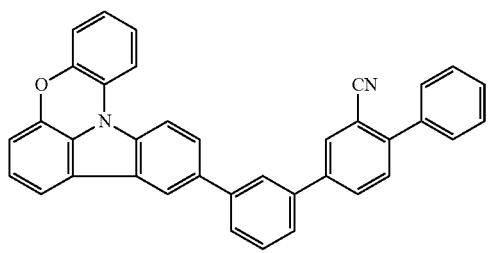

Compound (1-1-6)

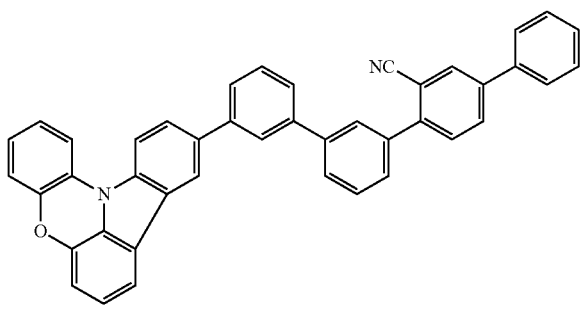

-continued
Compound (1-1-7)
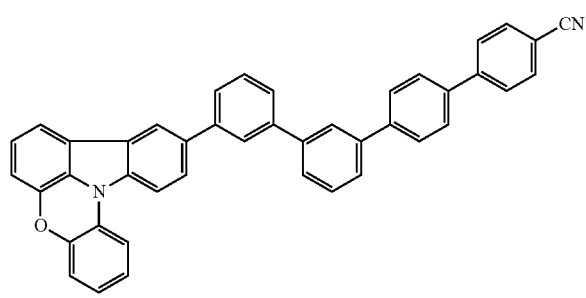
Compound (1-2-1)
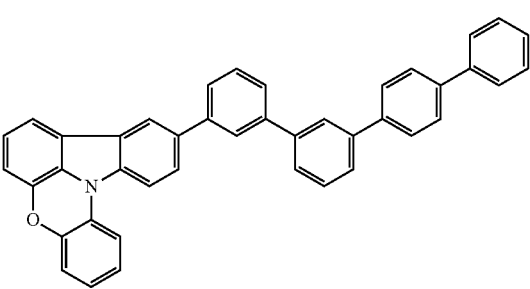
Compound (1-2-4)
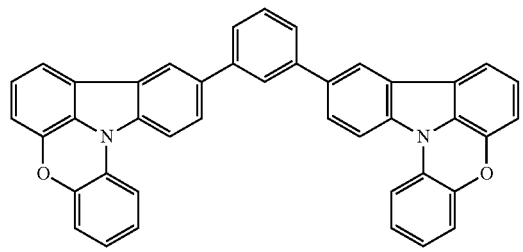
Compound (1-1-10)
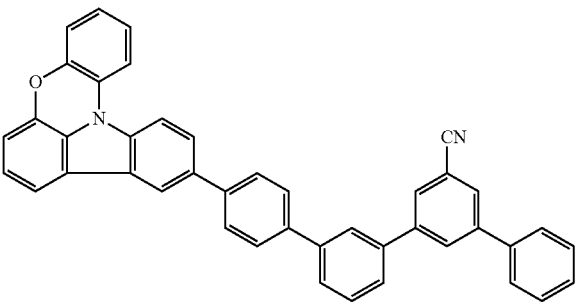
Compound (1-3-1)
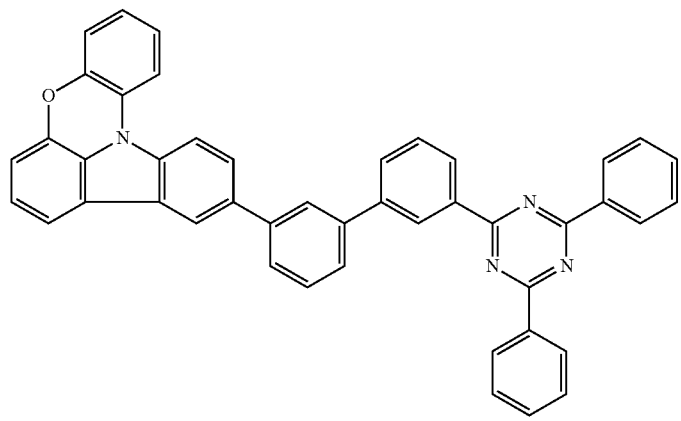
Compound (1-5-2)
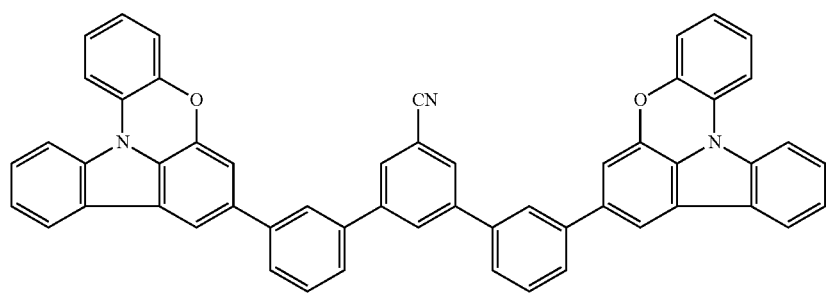
Comparative Compound (1) is Compound 44 in WO 2010/050778. Comparative Compound (2) is Compound H3 in WO 2011/042107. Comparative Compound (3) is Compound 85 in WO 2010/050778. Comparative Compound (4) is Compound 337 in WO 2010/050778. Comparative Compound (5) is Compound 16 in WO 2010/050778.

Comparative Compound (1)

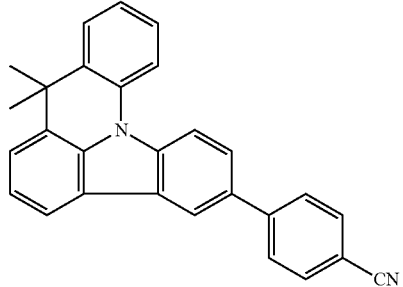

Comparative Compound (2)

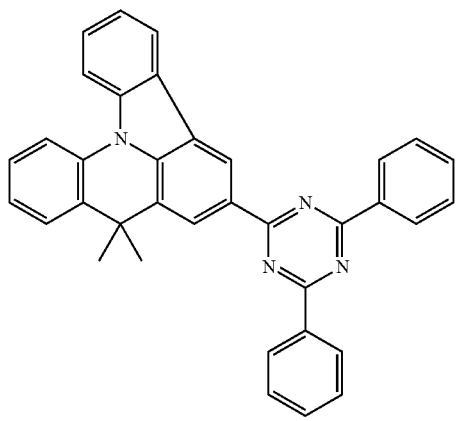

Comparative Compound (3)

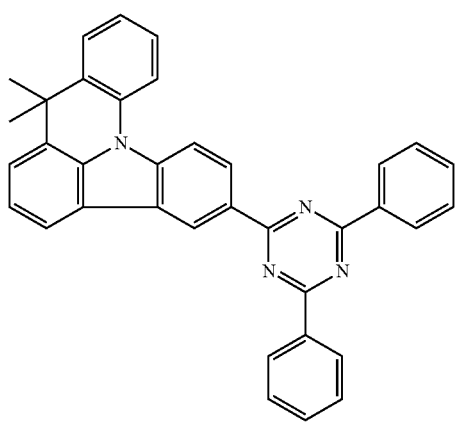

Comparative Compound (4)

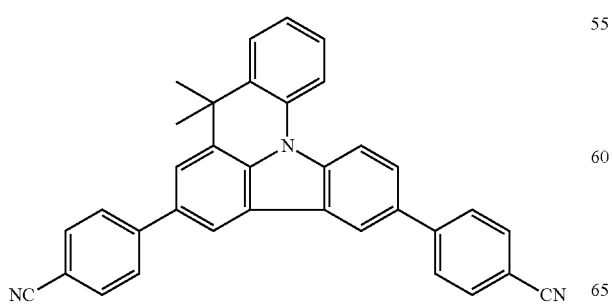

Comparative Compound (5)

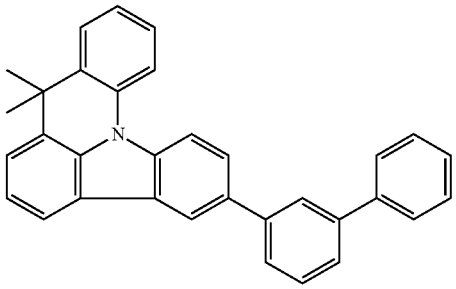

Example 1

<Fabrication and Evaluation of Element>: Use as Host Material of Light Emitting Layer in Green Phosphorescent Element The materials used in fabrication of elements were all subjected to sublimation purification and confirmed to have a purity (the area ratio of absorption intensity at 254 nm) of 99.1% or more by high performance liquid chromatography (Tosoh Corporation, TSK gel ODS-100Z).

A glass substrate (manufactured by Geomatec Co., Ltd., surface resistance: 10Ω/□) of 0.5 mm-thick and 2.5 cm-square having ITO film thereon was put in a cleaning container. After ultrasonic cleaning in 2-propanol, the glass substrate was subjected to a UV-ozone treatment for 30 minutes. The following organic layers were sequentially deposited on the above transparent anode (ITO film) by a vapor deposition method.

First layer: the following Compound (A), film thickness: 10 nm

Second layer: HTL-1, film thickness: 30 nm

Third layer: Compound (1-1-1) and GD-1 (mass ratio: 85:15), film thickness: 40 nm Fourth layer: ETL-1, film thickness: 40 nm Lithium fluoride (1 nm) and metal aluminum (100 nm) were vapor deposited thereon in this order to form a cathode.

This laminate was placed in a glove box purged with nitrogen gas without contact with atmospheric air, and sealed in a glass sealing can using an ultraviolet curing adhesive (XNR5516HV, manufactured by Nagase-Chiba, Ltd), to obtain an organic electroluminescent element of Example 1.

Material of Hole Injecting Layer (First Layer)

Compound (A): HAT-CN

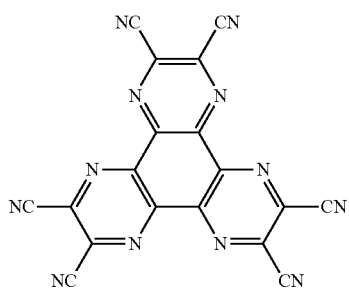 [SMILES: N#Cc1nc2c3nc(C#N)c(C#N)nc3c3nc(C#N)c(C#N)nc3c2nc1C#N]

Hole Transporting Material (Second Layer)

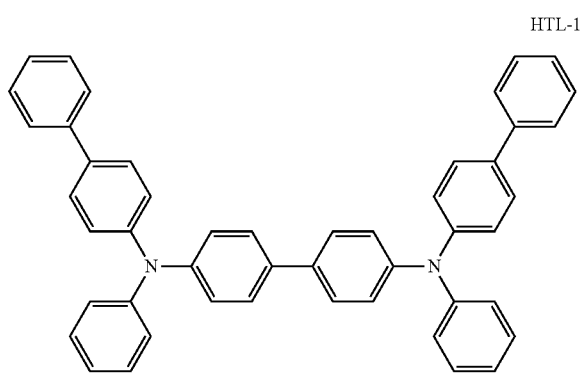 [SMILES: c1ccc(-c2ccc(N(c3ccccc3)c3ccc(-c4ccc(N(c5ccccc5)c5ccc(-c6ccccc6)cc5)cc4)cc3)cc2)cc1]
HTL-1

Material of Light Emitting Layer (Third Layer)
Host material: Compound (1-1-1) of the present invention
Light emitting material: GD-1

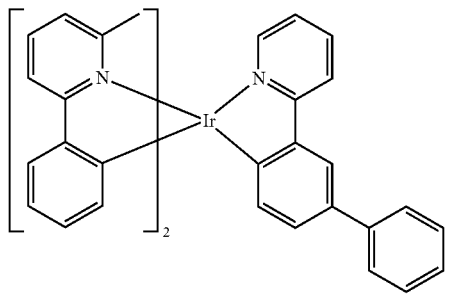

Electron Transporting Material (Fourth Layer)
ETL-1

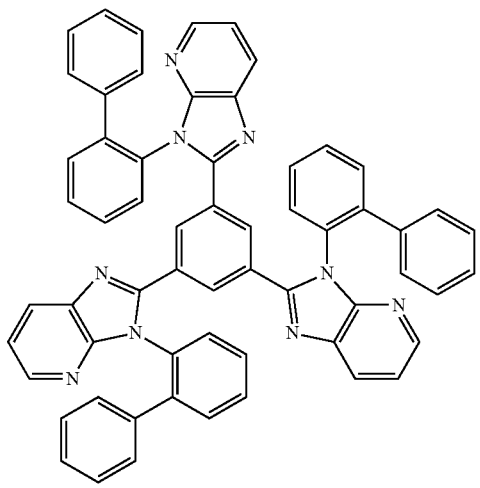 [SMILES: c1ccc(-c2ccccc2-n2c(-c3cc(-c4nc5cccnc5n4-c4ccccc4-c4ccccc4)cc(-c4nc5cccnc5n4-c4ccccc4-c4ccccc4)c3)nc3cccnc32)cc1]

Examples 2-12, Comparative Examples 1-5

Organic electroluminescent elements of Examples 2-12 and Comparative Examples 1-5 were obtained by the same procedure as in Example 1 except that Compound (1-1-1) of the third layer in the preparation of the organic electroluminescent element of Example 1 was replaced by the compound represented by any one of the general formulae (1-1) to (1-3) or Comparative Compound (1) to Comparative Compound (5) shown in Table 1 below.

These elements were evaluated in terms of driving voltage, external quantum efficiency (luminous efficiency), and durability, by the methods described below. The results are shown in Table 1 below.

(Driving Voltage)

A DC voltage was applied to each element to allow the element to emit light so as to attain the luminance of 1000 $cd/m^2$. The voltage applied at this time was used as an index of the evaluation of the driving voltage. The case of the driving voltage being 5 V or lower was rated as "ooo", the case of 5 V or higher and lower than 5.5 V as "oo", the case of 5.5 V or higher and less than 6 V as "o", the case of 6 V or higher and less than 7 V as "Δ", and the case of 7 V or higher was rated as "x". The results are shown in Table 1 below.

(External Quantum Efficiency)

A DC voltage was applied to each element to allow the element to emit light using Source/Measure Unit 2400 manufactured by TOYO Corporation, and the luminance was measured using Luminance Meter BM-8 manufactured by Topcon corporation. The emission spectrum and the emission peak wavelength were measured using Spectrum Analyzer PMA-11 manufactured by Hamamatsu Photonics K. K. The external quantum efficiency around the luminance of 1000 $cd/m^2$ was calculated based on the obtained values using a luminance conversion method.

The case of the external quantum efficiency being 15% or higher was rated as "ooo", the case of 10% or higher and lower than 15% as "o", the case of 8% or higher and lower than 10% as "x", and the case of lower than 8% was rated as "xx". The results are shown in Table 1 below.

(Durability)

A DC voltage was applied to each element to allow the element to emit light continuously so as to attain the luminance of 5000 $cd/m^2$ at room temperature (20° C.), and the time period required for the luminance to go down to 4000 $cd/m^2$ was measured. This time period was used as an index of the durability. The case of 600 hours or more was rated as "ooo", the case of 400 hours or more and less than 600 hours as "oo", the case of 200 hours or more and less than 400 hours as "o", the case of 100 hours or more and less than 200 hours as "Δ", and the case of less than 100 hours was rated as "x". The results are shown in Table 1 below.

TABLE 1

|  | Host material | Driving Voltage | External quantum efficiency | Durability |
|---|---|---|---|---|
| Example 1 | Compound (1-1-1) | ooo | ooo | ooo |
| Example 2 | Compound (1-1-2) | ooo | ooo | ooo |

TABLE 1-continued

|  | Host material | Driving Voltage | External quantum efficiency | Durability |
| --- | --- | --- | --- | --- |
| Example 3 | Compound (1-1-3) | ooo | ooo | oo |
| Example 4 | Compound (1-1-4) | ooo | ooo | ooo |
| Example 5 | Compound (1-1-5) | ooo | ooo | ooo |
| Example 6 | Compound (1-1-6) | ooo | ooo | ooo |
| Example 7 | Compound (1-1-7) | ooo | ooo | oo |
| Example 8 | Compound (1-2-1) | ooo | ooo | oo |
| Example 9 | Compound (1-2-4) | ooo | ooo | oo |
| Example 10 | Compound (1-1-10) | ooo | ooo | ooo |
| Example 11 | Compound (1-3-1) | ooo | ooo | o |
| Example 12 | Compound (1-5-2) | ooo | ooo | ooo |
| Comparative Example 1 | Comparative Compound (1) | o | xx | x |
| Comparative Example 2 | Comparative Compound (2) | o | xx | x |
| Comparative Example 3 | Comparative Compound (3) | o | xx | x |
| Comparative Example 4 | Comparative Compound (4) | o | xx | x |
| Comparative Example 5 | Comparative Compound (5) | o | o | x |

From Table 1 above, it was found that by using the compound according to the present invention as a host material (charge transporting material) of the light emitting layer in a green phosphorescence emitting element, it became possible to obtain an organic electroluminescent element which was driven with low driving voltage, and superior in luminous efficiency and durability.

Incidentally, the organic electroluminescent elements fabricated in Examples 1-12 each have an emission peak wavelength of 510 to 530 nm.

On the other hand, it was found that when Comparative Compounds 1-4 were used as a host material of the light emitting layer in a green phosphorescence emitting element, the elements were inferior in external quantum efficiency and durability. It was found that when Comparative Compound 5 was used as a host material of the light emitting layer in a green phosphorescence emitting element, the element was inferior in durability.

Examples 13-22

The compound according to the present invention was used as a hole transporting material to fabricate an organic electroluminescent element in the same manner.

Organic electroluminescent elements of Examples 13 to 22 and Comparative Examples 6 to 7 were obtained by the same procedure as in Example 4, except that Compound (HTL-1) in the second layer was replaced by a compound represented by any one of the general formulae (1-1) to (1-3) or Comparative Compound (HTL-2) in Table 2 below, or the light emitting material (GD-1) in the third layer was replaced by (GD-2) or (GD-3), in the preparation of the organic electroluminescent element of Example 4.

These elements were evaluated in terms of driving voltage, external quantum efficiency (luminous efficiency), and durability, by the methods described above. The results are shown in Table 2 below.

TABLE 2

|  | Hole transporting material of second layer | Light emitting material of third layer | Driving voltage | External quantum efficiency | Durability |
| --- | --- | --- | --- | --- | --- |
| Example 13 | Compound (1-2-1) | GD-1 | ooo | ooo | ooo |
| Example 14 | Compound (1-2-4) | GD-1 | ooo | ooo | ooo |
| Example 15 | Compound (1-2-5) | GD-1 | ooo | ooo | ooo |
| Example 16 | Compound (1-2-15) | GD-1 | ooo | ooo | ooo |
| Example 17 | Compound (1-2-18) | GD-1 | ooo | ooo | ooo |
| Example 18 | Compound (1-2-29) | GD-1 | ooo | ooo | ooo |
| Example 19 | Compound (1-2-30) | GD-1 | ooo | ooo | ooo |
| Example 20 | Compound (1-2-1) | GD-3 | ooo | ooo | ooo |
| Example 21 | Compound (1-2-30) | GD-2 | ooo | ooo | ooo |
| Example 22 | Compound (1-2-30) | GD-3 | ooo | ooo | ooo |
| Comparative Example 6 | Compound (HTL-2) | GD-2 | o | x | o |
| Comparative Example 7 | Compound (HTL-2) | GD-3 | o | x | o |

HTL-2

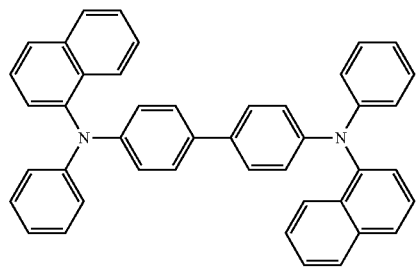 [SMILES: c1ccc(N(c2ccc(-c3ccc(N(c4ccccc4)c4cccc5ccccc45)cc3)cc2)c2cccc3ccccc23)cc1]

TABLE 2-continued

| | Hole transporting material of second layer | Light emitting material of third layer | Driving voltage | External quantum efficiency | Durability |
|---|---|---|---|---|---|

GD-2

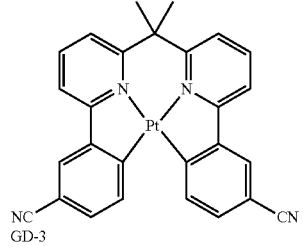

GD-3

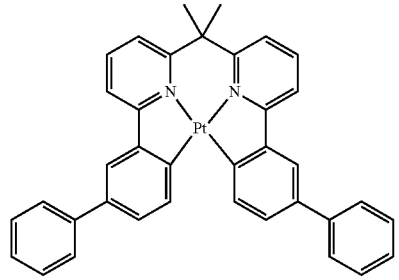

INDUSTRIAL APPLICABILITY

In the case of a light emitting device, a display device, and an illumination device, it is required to allow each pixel site to instantaneously emit light in a high luminance through a high current density. The light emitting element according to the present invention is designed to achieve a high luminous efficiency in such a case, thereby being able to be used advantageously.

In addition, the element of the present invention is excellent in durability, being suitable for a light emitting device, a display device and an illumination device.

DESCRIPTION OF REFERENCE NUMERALS AND SIGNS

2 Substrate
3 Anode
4 Hole injecting layer
5 Hole transporting layer
6 Light emitting layer
7 Hole blocking layer
8 Electron transporting layer
9 Cathode
10 Organic electroluminescent element (Organic EL element)
11 Organic layer
12 Protective layer
14 Adhesive layer
16 Sealing enclosure
20 Light emitting device
30 Light scattering member
30A Light incidence plane
30B Light output plane
31 Transparent substrate
32 Fine particle
40 Illumination device

What is claimed:

1. A charge transporting material comprising a compound represented by any one of the following general formula (1-1) to general formula (1-3):

General Formula (1-1)

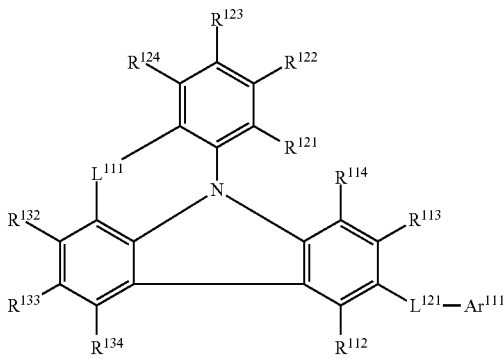

General Formula (1-2)

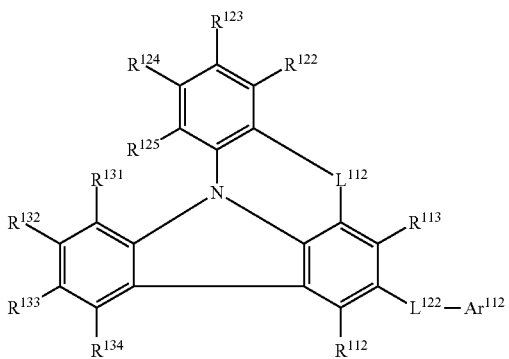

General Formula (1-3)

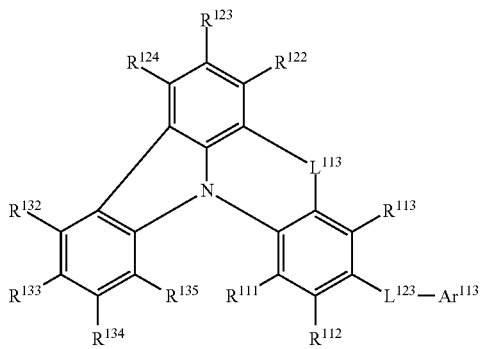

wherein, in the general formulae (1-1) to (1-3), $R^{112}$, $R^{113}$, $R^{122}$ to $R^{124}$, and $R^{132}$ to $R^{134}$ each independently represent a hydrogen atom or a substituent, and may be bound together to form a ring;

$R^{111}$, $R^{114}$, $R^{121}$, $R^{125}$, $R^{131}$, and $R^{135}$ are each hydrogen;

$L^{111}$ to $L^{113}$ each independently represents O or S;

$L^{121}$ to $L^{123}$ each independently represent a single bond or an arylene group; and $Ar^{111}$ to $Ar^{113}$ each independently represent a substituent represented by one of General Formula (2-1) to General Formula (2-10)

General Formula (2-1)

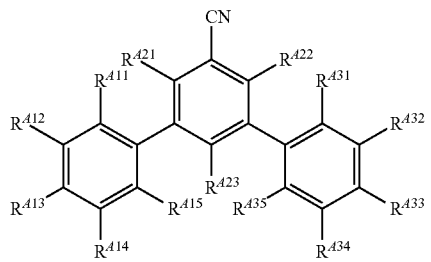

General Formula (2-2)

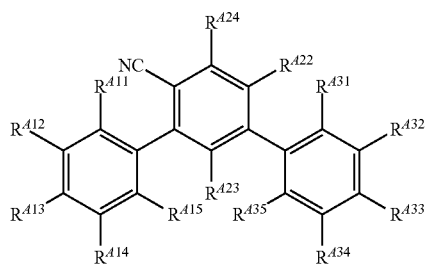

General Formula (2-3)

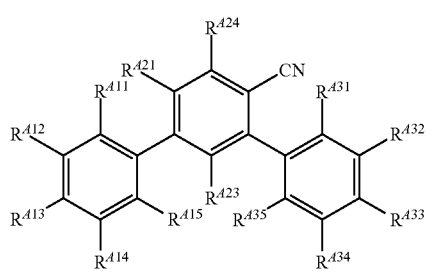

General Formula (2-4)

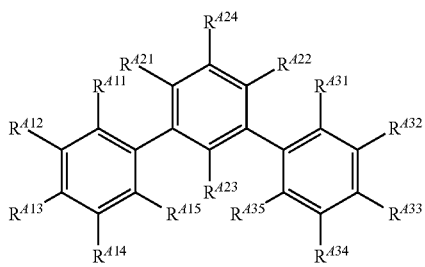

General Formula (2-5)

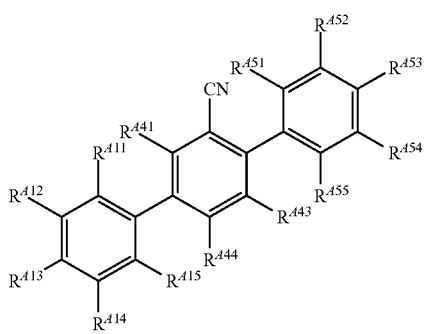

General Formula (2-6)

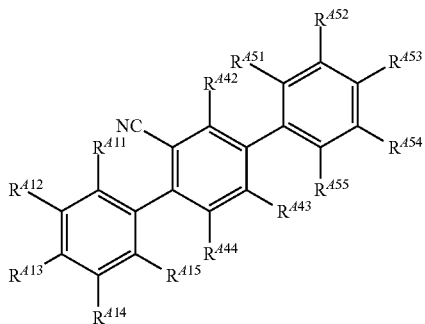

General Formula (2-7)

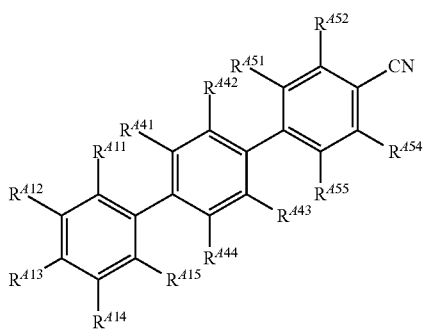

General Formula (2-8)

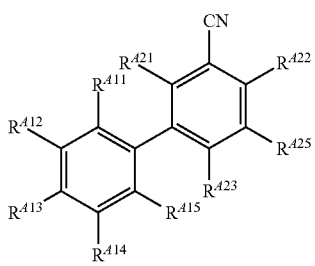

General Formula (2-9)

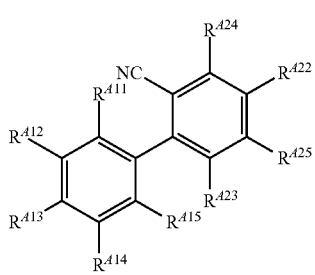

General Formula (2-10)

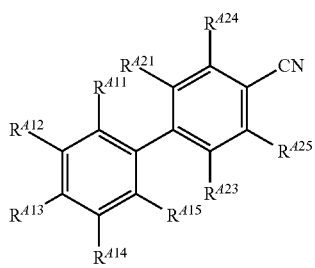

wherein, in the general formula (2-1) to the general formula (2-10), one of $R^{A11}$ to $R^{A15}$ represents a binding position to $L^{121}$ to $L^{123}$ in the general formulae (1-1) to (1-3) and the others of $R^{A11}$ to $R^{A15}$ each independently represent a hydrogen atom, an alkyl, an aryl, a cyano, an indolophenoxazine or an indolophenothiazine;

$R^{A21}$ to $R^{A25}$, $R^{A31}$ to $R^{A35}$, $R^{A41}$ to $R^{A44}$ and $R^{A51}$ to $R^{A55}$ each independently represent a hydrogen atom, an alkyl, an aryl, a cyano, an indolophenoxazine or an indolophenothiazine;

wherein in the compound, none or only one of $R^{A11}$ to $R^{A15}$, $R^{A11}$ to $R^{A25}$, $R^{A31}$ to $R^{A35}$, $R^{A41}$ to $R^{A44}$ and $R^{A51}$ to $R^{A55}$ represents an indolophenoxazine or an indolophenothiazine, and wherein the indolophenoxazine or an indolophenothiazine is an indolophenoxazin-3-yl, an indolophenoxazin-7-yl, an indolophenoxazin-10-yl, an indolophenothiazin-3-yl, an indolophenothiazin-7-yl, or an indolophenothiazin-10-yl.

2. The charge transporting material according to claim 1, which comprises a compound represented by the general formula (1-1) or the general formula (1-2).

3. The charge transporting material according to claim 1, wherein at least one of $L^{121}$ to $L^{123}$ and $Ar^{111}$ to $Ar^{113}$ in the general formulae (1-1) to (1-3) contains an m-phenylene group.

4. An organic electroluminescent element comprising a substrate; a pair of electrodes including an anode and a cathode, disposed on the substrate; and an organic layer disposed between the electrodes, wherein the organic layer contains the charge transporting material of claim 1.

5. The organic electroluminescent element according to claim 4, wherein the organic layer includes a light emitting layer containing a phosphorescence emitting material.

6. The organic electroluminescent element according to claim 5, wherein the light emitting layer contains the compound represented by any one of the general formula (1-1) to the general formula (1-3).

7. The organic electroluminescent element according to claim 5, wherein an Ir complex represented by the following general formula (E-1) is used in the light emitting layer as the phosphorescence emitting material:

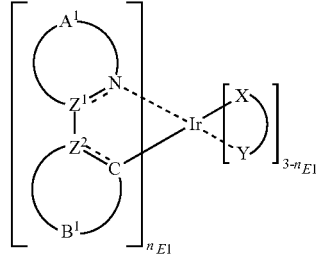

(E-1)

wherein, in the general formula (E-1), $Z^1$ and $Z^2$ each represent a carbon atom or a nitrogen atom; $A^1$ represents an atomic group which together with $Z^1$ and a nitrogen atom forms a 5- or 6-membered hetero ring; $B^1$ represents an atomic group which together with $Z^2$ and a carbon atom forms a 5- or 6-membered ring; (X—Y) represents a mono-anionic bidentate ligand; and $n_{E1}$ represents an integer of 1 to 3.

8. The organic electroluminescent element according to claim 7, wherein the Ir complex represented by the general formula (E-1) is represented by the following general formula (E-2):

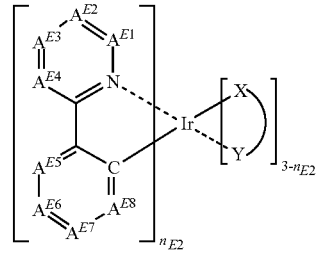

(E-2)

wherein, in the general formula (E-2), $A^{E1}$ to $A^{E8}$ each independently represent a nitrogen atom or C—$R^E$; $R^E$ represents a hydrogen atom or a substituent; (X—Y) represents a mono-anionic bidentate ligand; and $n_{E2}$ represents an integer of 1 to 3.

9. A light emitting device comprising the organic electroluminescent element of claim 4.

10. A display device comprising the organic electroluminescent element of claim 4.

11. An illumination device comprising the organic electroluminescent element of claim 4.

12. The charge transporting material according to claim 1, wherein in the general formulae (1-1) to (1-3), $R^{112}$, $R^{113}$, $R^{122}$ to $R^{124}$, and $R^{132}$ to $R^{134}$ each independently represent a hydrogen atom, an alkyl, an aryl, a cyano, or may be bound together to form a ring.

13. The charge transporting material according to claim 1, wherein when one of $R^{A11}$ to $R^{A15}$, $R^{A21}$ to $R^{A25}$, $R^{A31}$ to $R^{A35}$, $R^{A41}$ to $R^{A44}$, and $R^{A51}$ to $R^{A55}$ represents an indolophenoxazine or indolophenothiazine, the indolophenoxazine or indolophenothiazine is unsubstituted.

* * * * *